United States Patent
Finley et al.

(10) Patent No.: US 9,849,135 B2
(45) Date of Patent: Dec. 26, 2017

(54) USP14 INHIBITORS FOR TREATING OR PREVENTING VIRAL INFECTIONS

(71) Applicants: President and Fellows of Harvard College, Cambridge, MA (US); Health Research, Inc., Menands, NY (US)

(72) Inventors: Daniel J. Finley, Jamaica Plain, MA (US); Dilip Nag, Delmar, NY (US); Laura D. Kramer, Albany, NY (US)

(73) Assignees: President and Fellows of Harvard College, Cambridge, MA (US); Health Research, Inc., Menands, NY (US)

( * ) Notice: Subject to any disclaimer, the term of this patent is extended or adjusted under 35 U.S.C. 154(b) by 0 days.

(21) Appl. No.: 14/761,089

(22) PCT Filed: Jan. 25, 2013

(86) PCT No.: PCT/US2013/023147
§ 371 (c)(1),
(2) Date: Jul. 15, 2015

(87) PCT Pub. No.: WO2014/116228
PCT Pub. Date: Jul. 31, 2014

(65) Prior Publication Data
US 2015/0335652 A1    Nov. 26, 2015

(51) Int. Cl.
*A61K 31/5377* (2006.01)
*A61K 31/4025* (2006.01)
*A61K 31/402* (2006.01)
*A61K 31/454* (2006.01)
*A61K 31/496* (2006.01)
*A61K 31/4545* (2006.01)
*A61K 31/506* (2006.01)
*A61K 31/40* (2006.01)
*A61K 31/4178* (2006.01)
*A61K 31/4192* (2006.01)
*A61K 31/437* (2006.01)
*A61K 31/4985* (2006.01)

(52) U.S. Cl.
CPC .......... *A61K 31/5377* (2013.01); *A61K 31/40* (2013.01); *A61K 31/402* (2013.01); *A61K 31/4025* (2013.01); *A61K 31/4178* (2013.01); *A61K 31/4192* (2013.01); *A61K 31/437* (2013.01); *A61K 31/454* (2013.01); *A61K 31/4545* (2013.01); *A61K 31/496* (2013.01); *A61K 31/4985* (2013.01); *A61K 31/506* (2013.01)

(58) Field of Classification Search
None
See application file for complete search history.

(56) References Cited

U.S. PATENT DOCUMENTS

| | | | |
|---|---|---|---|
| 4,148,895 | A | 4/1979 | Lattrell et al. |
| 4,290,940 | A | 9/1981 | Wirth et al. |
| 5,561,149 | A | 10/1996 | Azria et al. |
| 5,852,046 | A | 12/1998 | Lang et al. |
| 5,859,035 | A | 1/1999 | Anthony et al. |
| 6,063,782 | A | 5/2000 | Kimura et al. |
| 6,201,129 | B1 | 3/2001 | Miller et al. |
| 6,310,217 | B1 | 10/2001 | Lehr |
| 6,469,171 | B1 | 10/2002 | Banwell et al. |
| 6,500,853 | B1 | 12/2002 | Seehra et al. |
| 6,589,954 | B1 | 7/2003 | Mavunkel et al. |
| 6,627,645 | B2 | 9/2003 | Andersson et al. |
| 6,828,344 | B1 | 12/2004 | Seehra et al. |
| 6,867,209 | B1 | 3/2005 | Mavunkel et al. |
| 7,238,713 | B2 | 7/2007 | Anderson et al. |
| 7,417,063 | B2 | 8/2008 | Smallheer et al. |
| 7,425,642 | B2 | 9/2008 | Watanabe et al. |
| 7,482,354 | B2 | 1/2009 | Traquandi et al. |
| 7,528,165 | B2 | 5/2009 | Hsieh et al. |

(Continued)

FOREIGN PATENT DOCUMENTS

| | | |
|---|---|---|
| CN | 101016294 A | 8/2007 |
| DE | 4325204 A1 | 2/1995 |

(Continued)

OTHER PUBLICATIONS

Lee et al. "Enhancement of Proteasome Activity by a Small-Molecule Inhibitor of USP14". Nature. Sep. 2010; 467:179-184.*

(Continued)

*Primary Examiner* — Jeffrey S Lundgren
*Assistant Examiner* — Michael Schmitt
(74) *Attorney, Agent, or Firm* — Foley Hoag LLP

(57) ABSTRACT

Disclosed herein are methods of treating or preventing a viral infection resulting from infection by a flavivirus, comprising administering to a subject a small molecule inhibitor of USP14, represented by Formula (I) or a pharmaceutically acceptable salt, solvate, hydrate, prodrug, chemically-protected form, enantiomer or stereoisomer thereof, and pharmaceutical compositions comprising an effective amount of a compound of Formula (I) for use in the method.

(I)

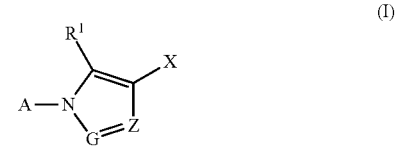

22 Claims, 2 Drawing Sheets

(56) References Cited

U.S. PATENT DOCUMENTS

| | | | |
|---|---|---|---|
| 7,576,206 | B2 | 8/2009 | Bernardini et al. |
| 7,632,955 | B2 | 12/2009 | Hsieh et al. |
| 7,767,817 | B2 | 8/2010 | Wang et al. |
| 7,781,479 | B2 | 8/2010 | Takahashi et al. |
| 8,097,644 | B2 | 1/2012 | Beard et al. |
| 8,197,819 | B2 | 6/2012 | Srivastava et al. |
| 8,293,781 | B2 | 10/2012 | Tomoo et al. |
| 2002/0037887 | A1 | 3/2002 | Pintor et al. |
| 2004/0122096 | A1 | 6/2004 | Lang et al. |
| 2005/0075348 | A1 | 4/2005 | Harriman et al. |
| 2005/0113357 | A1 | 5/2005 | Anderson et al. |
| 2006/0135540 | A1 | 6/2006 | Lin et al. |
| 2007/0185184 | A1 | 8/2007 | Hanson et al. |
| 2007/0203121 | A1 | 8/2007 | Merce Vidal et al. |
| 2008/0171772 | A1 | 7/2008 | Beard et al. |
| 2008/0188453 | A1 | 8/2008 | Adams et al. |
| 2009/0047246 | A1 | 2/2009 | Beigelman et al. |
| 2009/0118503 | A1 | 5/2009 | Sprott et al. |
| 2009/0143371 | A1 | 6/2009 | Buettelmann et al. |
| 2009/0163545 | A1 | 6/2009 | Goldfarb |
| 2009/0215750 | A1 | 8/2009 | Bamberg et al. |
| 2009/0227538 | A1 | 9/2009 | Fruchtel et al. |
| 2009/0264384 | A1 | 10/2009 | Didsbury et al. |
| 2009/0264457 | A1 | 10/2009 | Codony-Soler et al. |
| 2009/0318446 | A1 | 12/2009 | Fischer et al. |
| 2010/0074955 | A1 | 3/2010 | Buschmann et al. |
| 2010/0087415 | A1 | 4/2010 | Whitten et al. |
| 2010/0087446 | A1 | 4/2010 | Chakravarty et al. |
| 2010/0099726 | A1 | 4/2010 | Cantley et al. |
| 2010/0197708 | A1 | 8/2010 | Talley et al. |
| 2010/0204282 | A1 | 8/2010 | Hutchinson et al. |
| 2010/0249069 | A1 | 9/2010 | Donello et al. |
| 2010/0331297 | A1 | 12/2010 | Bulawa et al. |
| 2011/0009453 | A1 | 1/2011 | Donello et al. |
| 2011/0098483 | A1 | 4/2011 | Petasis et al. |
| 2011/0144090 | A1 | 6/2011 | Elder et al. |
| 2011/0319403 | A1 | 12/2011 | Zhou et al. |
| 2012/0006417 | A1 | 1/2012 | Folk |
| 2012/0022057 | A1 | 1/2012 | Zhou et al. |
| 2012/0064175 | A1 | 3/2012 | Vukovic et al. |
| 2012/0071448 | A1 | 3/2012 | Donello et al. |
| 2012/0245186 | A1 | 9/2012 | Blackman et al. |
| 2012/0316193 | A1 | 12/2012 | Foley et al. |
| 2013/0029948 | A1 | 1/2013 | Roppe et al. |
| 2013/0045992 | A1 | 2/2013 | Finley et al. |
| 2013/0150385 | A1 | 6/2013 | Blackman et al. |
| 2013/0156755 | A1 | 6/2013 | Blackman et al. |
| 2013/0171105 | A1 | 7/2013 | Blackman et al. |

FOREIGN PATENT DOCUMENTS

| | | |
|---|---|---|
| EP | 0 562 832 | 9/1993 |
| EP | 0 639 573 | 7/1994 |
| EP | 1837329 A1 | 9/2007 |
| EP | 2020230 A1 | 2/2009 |
| EP | 2141163 A1 | 1/2010 |
| JP | 07-133274 | 5/1995 |
| JP | 2000063354 A | 2/2000 |
| JP | 2001151771 A | 6/2001 |
| JP | 2009179589 A | 8/2009 |
| WO | WO-95/13266 A1 | 5/1995 |
| WO | WO-97/36881 | 10/1997 |
| WO | WO-97/46226 A2 | 12/1997 |
| WO | WO-98/27089 A1 | 6/1998 |
| WO | WO-99/43672 A1 | 9/1999 |
| WO | WO-2001/44182 A2 | 6/2001 |
| WO | WO-2003/041644 A2 | 5/2003 |
| WO | WO-2004/020409 A1 | 3/2004 |
| WO | WO-2004/104007 | 12/2004 |
| WO | WO-2005/021558 | 3/2005 |
| WO | WO-2005/025515 | 3/2005 |
| WO | WO-2005/066126 A1 | 7/2005 |
| WO | WO-2006/087355 | 8/2006 |
| WO | WO-2006/125324 A1 | 11/2006 |
| WO | WO-2007/095561 | 8/2007 |
| WO | WO-2008/024978 A2 | 2/2008 |
| WO | WO-2008/100867 A2 | 8/2008 |
| WO | WO-2008/109702 A1 | 9/2008 |
| WO | WO-2008/147536 | 12/2008 |
| WO | WO-2009/013010 A2 | 1/2009 |
| WO | WO-2009/062118 | 5/2009 |
| WO | WO-2009/071577 | 6/2009 |
| WO | WO-2009/073620 | 6/2009 |
| WO | WO-2009/097141 | 8/2009 |
| WO | WO-2009/108551 | 9/2009 |
| WO | WO-2009/117676 | 9/2009 |
| WO | WO-2009/118292 | 10/2009 |
| WO | WO-2009/127686 | 10/2009 |
| WO | WO-2009/130481 A1 | 10/2009 |
| WO | WO-2009/136175 | 11/2009 |
| WO | WO-2009/158011 | 12/2009 |
| WO | WO-2009/158371 | 12/2009 |
| WO | WO-2010/015816 A2 | 2/2010 |
| WO | WO-2010/019391 A1 | 2/2010 |
| WO | WO-2010/067123 A1 | 6/2010 |
| WO | WO-2011/038579 A1 | 4/2011 |
| WO | WO-2011/094545 A2 | 8/2011 |
| WO | WO 2011094545 A2 * 8/2011 ......... C07D 207/333 |  |
| WO | WO-2011/127333 A2 | 10/2011 |
| WO | WO-2012/012712 | 1/2012 |
| WO | WO-2012/078757 A2 | 6/2012 |
| WO | WO-2012/096919 A1 | 7/2012 |
| WO | WO-2012/106343 A2 | 8/2012 |
| WO | WO-2012/116061 A1 | 8/2012 |
| WO | WO-2012/116247 A1 | 8/2012 |
| WO | WO-2012/141796 A2 | 10/2012 |
| WO | WO-2012/162293 A1 | 11/2012 |
| WO | WO-2012/162372 A1 | 11/2012 |
| WO | WO-2012/162584 A1 | 11/2012 |
| WO | WO-2013/006864 A2 | 1/2013 |
| WO | WO-2013/014104 A1 | 1/2013 |
| WO | WO-2013/067162 A1 | 5/2013 |
| WO | WO-2013/067165 A1 | 5/2013 |
| WO | WO-2013/074594 A1 | 5/2013 |

OTHER PUBLICATIONS

Chen et al. Antiviral Chemistry & Chemotherapy 2009 (19) 151-156.*
Wang et al. Journal of Virology 2011 (85) 3758-3766.*
Perry et al. PLoS Pathogens 2012 (8) e1002783.*
Nag et al. Virus Research 2012 (165) 103-106.*
Lee et al., "Enhancement of Proteasome Activity by a Small-Moleculue Inhibitor of Usp14," Nature, 467(7312):179-184 (2010).
Nag et al., "A small-molecule inhibitor of deubiquitinating enzyme USP14 Inhibits Dengue virus replication," Virus Research, 165:103-106 (2012).
International Search Report dated Apr. 10, 2013, from PCT/US13/23147.
Abdel-Motaleb et al., "Studies with Azoles and Benzoazoles: A Novel Simple Approach for Synthesis of 3-Functionally Substituted 3-Acylindoles," J. Heterocyclic. Chem., 44(1):109-114 (2007).
Aparoy et al., "Pharmacophore modeling and virtual screening for designing potential 5-Lipoxygenase inhibitors," Bioorganic & Medicinal Chemistry Letters, 20(3):1013-1018 (2010).
CAS RN 133674-62-1, STN Entry Date May 10, 1991.
CAS RN 169501-21-7 STN Entry Date Nov. 1, 1995.
CAS RN 57248-18-7 STN Entry Date Nov. 16, 1984.
CAS RN 784194-52-1 STN Entry Date Nov. 19, 2004.
Database Registry Chemical Abstracts, Ethanone, 1-[1-(2-fluorophenyl)-2, 5-dimethyl-1H-pyrrol-3-yl]-2-(4-methyl-1-piperidinyl)-, Database Accession No. 380907-35-7, CAS Registry No. 380907-35-7 (Jan. 8, 2002).
Database Registry Chemical Abstracts, Ethanone, 1-[1-(4-fluorophenyl)-2, 5-dimethyl-1H-pyrrol-3-yl]-2-(1-piperidinyl)-, Database Accession No. 670268-20-9, CAS Registry No. 670268-20-9 (Apr. 2, 2004).
Database Registry Chemical Abstracts, Ethanone, 1-[1-(4-fluorophenyl)-2, 5-dimethyl-1H-pyrrol-3-yl]-2-(1-pyrrolidinyl)-, Database Accession No. 314245-33-5, CAS Registry No. 314245-33-5 (Jan. 17, 2001).

(56) References Cited

OTHER PUBLICATIONS

Database Registry Chemical Abstracts, Ethanone, 1-[1-(4-fluorophenyl)-2, 5-dimethyl-1H-pyrrol-3-yl]-2-(4-methyl-1-piperidinyl)-, Database Accession No. 325742-01-6, CAS Registry No. 325742-01-6 (Mar. 5, 2001).
Database Registry Chemical Abstracts, Ethanone, 1-[2, 5-dimethyl-1-(4-methylphenyl)-1H-pyrrol-3-yl]-2-(1-piperidinyl)-, Database Accession No. 301683-66-9, CAS Registry No. 301683-66-9 (Nov. 8, 2000).
Database Registry Chemical Abstracts, Ethanone, 2-(2, 6-dimethyl-4-morpholinyl)-1-(2, 5-dimethyl-1-phenyl-1H-pyrrol-3-yl)-, Database Accession No. 314261-13-7, CAS Registry No. 314261-13-7 (Jan. 17, 2001).
De Freitas et al., "Development of CoMFA and CoMSIA models of affinity and selectivity for indole ligands of cannabinoid CB1 and CB2 receptors," European Journal of Medicinal Chemistry, 44:2482-2496 (2009).
Dörwald, F.Z., "Side Reactions in Organic Synthesis," 2005, Wiley: VCH, Weinheim p. IX of Preface p. 1-15.
Examiner's Notification of Defects from related application HMV-194.65, dated Dec. 22, 2015.
Gadaginamath et al., "Synthesis and Antimicrobial Activity of 4-Iso-Gramines, 4-Aryl-Thiomethyl and 3-Aminoacetyl Derivatives of 2-Methylindoles," Revue Roumaine de Chimie, 40(30):265-273 (1995).
Gadaginamath et al., "Synthesis and Antimicrobial Activity of Novel 3-Thiazolyl/Imidazo (2,1-b)-1,3,4-Thiadiazolyl/Anilinoacetyl/Phenoxyacetyl Indole Derivatives," Indian Journal of Heterocyclic Chemistry, 9(1):33-38 (1999).
Gitto et al., "Development of 3-substituted-1H-indole derivatives as NR2B/NMDA receptor antagonists", Bioorganic & Medicinal Chemistry, 17(4): 1640-1647 (2009).
International Search Report dated Oct. 24, 2011, from PCT/US2011/022929.
Iwaki et al., "Water-Soluble Melatonins: Syntheses of Melatonins Carrying a Glycosyl Group at the 1-Position," Heterocyles, 60(6):1411-1418 (2003).
Kang et al., "Cell Cycle Arrest and Cytochrome c-mediated Apoptotic Induction in A549 Human Lung Cancer Cells by MCS-C2, an Analog of Sangivamycin," Journal of Microbiology and Biotechnology, 20(2):428-432 (2010).
Liu et al., "Discovery of a Peroxisome Proliferator Activated Receptor γ (PPARγ) Modulator with Balanced PPARα Activity for the Treatment of Type 2 Diabetes and Dyslipidemia," J. Med. Chem., 52(14): 4443-4453 (2009).
Marchand et al., "Synthesis and structure-activity relationships of N-aryl(indol-3-yl)glyoxamides as antitumor agents", Bioorganic & Medicinal Chemistry, 17(18): 6715-6727 (2009).
Notification receipt from foreign associate, from related application HMV-194.65, dated Dec. 24, 2015.
Office Action dated Dec. 31, 2014, from U.S. Appl. No. 13/468,757.
Office Action dated Jul. 14, 2014, from U.S. Appl. No. 13/468,757.
Preobrazhenskaya et al., "Synthesis and Study of the Pharmacological Activity of 1-(Indolyl-3')-2-Alkylaminoethanols", Pharmaceutical Chemistry Journal, pp. 532-536 (1970). Retrieved from the Internet: URL:http://rd.springer.com/content/pdf/10.1007/BF00763238.pdf [retrieved on Oct. 7, 2014].
Rao et al., "An efficient, mild, and selective Ullmann-type N-arylation of indoles catalyzed by copper(I) complex", Tetrahedron, 65(23): 4619-4624 (2009).
Registry (STN) CAS Registration No. 314261-13-7.
Registry (STN) CAS Registration No. 325742-01-6.
Registry (STN) CAS Registration No. 380907-35-7.
Registry (STN) CAS Registration No. 670268-20-9.
Stearns et al., "Synthesis and biological evaluation of 6-aryl-6H-pyrrolo[3,4-d]pyridazine derivatives: high-affinity ligands to the α2δ subunit of voltage gated calcium channels," Bioorganic & Medicinal Chemistry Letters, 14(5):1295-1298 (2004).
Supplementary European Search Report from EP 11 73 7731 dated Jul. 3, 2014.
Van Zandt et al., "Discovery of 3-[(4,5, 7-Trifluorobenzothiazol-2-yl)methyl]indole-N-acetic Acid (Lidorestat) and Congeners as Highly Potent and Selective Inhibitors of Aldose Reductase for Treatment of Chronic Diabetic Complications," J. Med. Chem., 48:3141-3152 (2005).
Venkatesh, S. et al, "Role of the Development Scientist in Compound Lead Selection and Optimization," Journal of Pharmaceutical Sciences, vol. 89, 145-154 (2000).
Vidovic et al., "A Combined Ligand- and Structure-Based Virtual Screening Protocol Identifies Submicromolar PPARγ Partial Agonists," Chem Med Chem, 6(1): 94-103 (2011).
West, Solid-State Chemistry and Its Applications, John Wiley & Sons (1984).
Wolff, Burger's Medicinal Chemistry and Drug Discovery, vol. 1, Principles and Practice, John Wiley & Sons, New York (1997).

* cited by examiner

IU1

USP14 INHIBITORS FOR TREATING OR PREVENTING VIRAL INFECTIONS

RELATED APPLICATIONS

This application is the National Stage application of PCT/US13/023147, filed Jan. 25, 2013, which is hereby incorporated in its entirety by this reference.

BACKGROUND

The flavivirus family includes several clinically important animal viruses, including Dengue, West Nile, Japanese encephalitis, yellow fever, and tick-borne encephalitis viruses. Dengue is one of the most serious infectious diseases globally. There are about 100 million cases every year, with over 500,000 cases of potentially fatal Dengue hemorrhagic fever. Dengue virus (DENV) puts nearly 2.5 billion people at risk of infection in tropical and subtropical countries. Similarly, West Nile virus (WNV) has caused thousands of human infections in North America, besides infecting people on other continents. WNV infection can lead to serious illnesses in humans, resulting in encephalitis and death. Neither a prophylactic vaccine nor antiviral therapies are available for both WNV and DENV. The development of either a vaccine or an antiviral drug requires detailed knowledge of the viral life cycle.

The flaviviruses have a small positive sense RNA genome that is translated into a polyprotein, which is co- and post-translationally cleaved by both viral and host proteases into three structural (C, E, and M) and seven non-structural (NS) proteins (NS1, NS2A, NS2B, NS3, NS4A, NS4B, and NS5). The non-structural proteins aid in viral genome replication. Since viruses encode a limited number of proteins, it is likely that viral proteins recruit or interact with several host proteins to make the cellular environment conducive to viral replication by inhibiting or interfering with the function of cellular factors that would otherwise obstruct virus infection and production. Several investigators have successfully utilized high-throughput screening methods (e.g., a genome-scale RNAi screen) to identify the mammalian or insect host genes that either facilitate or interfere with viral replication. These proteins are involved in various host cell processes, including intracellular protein trafficking, signal transduction, ion and molecular transport, and nucleic acid, protein, and lipid metabolism. Recent protein—protein interaction studies between viral proteins and host factors indicated that each viral protein interacts with several host proteins, suggesting that each viral protein performs multiple functions by interacting or recruiting different host factors.

The RNAi- screening studies and several proteomic studies have identified a role of the ubiquitin- proteasome system (UPS) for WNV and DENV replication Inhibition of the UPS by RNAi or by a chemical inhibitor significantly reduces the viral yield. However, the targets of the UPS are currently unknown and require further investigation. The UPS is a major extralysosomal protein- degradation pathway that degrades misfolded or unnecessary proteins from the cytosol and the nucleus, and also provides for signal-dependent or temporally specific degradation of numerous regulatory proteins. It plays a key role in maintaining cellular protein homeostasis. Consequently, it is involved in several cellular processes, including the stress response, cell-cycle regulation, DNA repair, antigen presentation, apoptosis, signal transduction, and transcriptional regulation. Proteins destined for degradation by the UPS are tagged with ubiquitin in a cascade of reactions, involving ubiquitin activation by a ubiquitin-activating enzyme (E1), followed by transfer of the activated ubiquitin to a ubiquitin-conjugating enzyme (E2). Finally, the ubiquitin-protein ligase (E3) transfers the ubiquitin to the target protein to an internal lysine residue on the substrate. After the initial ubiquitination event on a given substrate, additional ubiquitin groups are often added, and in many cases the additional ubiquitin groups are attached to a previously conjugated ubiquitin rather than directly to the substrate. This type of ubiquitin conjugation leads to the formation of "ubiquitin chains" on substrates. Once the target protein is tagged with ubiquitin, it is then degraded by the 26S proteasome protein complex with the release of ubiquitin for recycling. The efficiency of targeting a substrate for degradation is thought to depend on the number of bound ubiquitin groups, or the length of the bound ubiquitin chains, with chains of four or more ubiquitin groups allowing for rapid substrate turnover.

Ubiquitination is a reversible process; the ubiquitin chain can be made shorter or removed by a set of enzymes known as deubiquitinating enzymes (DUBs). Modification of the ubiquitin chain length regulates substrate degradation rates by altering substrate affinity for the proteasome. Ubiquitin-specific proteases (USPs) and ubiquitin C-terminal hydrolases (UCHs) are the best-characterized DUBs. Several DUBs have been implicated in disease mechanisms, including neurological disorders, infectious diseases, and cancer. Consequently, DUBs are plausible targets for drug discovery, and several small-molecule inhibitors targeting DUBs have been identified. Recently, a small molecule inhibitor of a mammalian proteasome—associated DUB, USP14, was identified. The compound 1-[1-(4-fluorophenyl)-2,5-dimethylpyrrol-3-yl]-2pyrrolidin-1-ylethanone (also called IU1) is specific for USP14, and it enhances proteolysis in mammalian cells.

Members of multiple families of both RNA and DNA viruses reprogram the UPS for various purposes, including immune evasion, viral entry and release, transcriptional regulation, and apoptosis. For example, human cytomegalovirus, herpesviruses, and Epstein Barr virus escape host immune responses by altering the processing of MHC molecules by the proteasome. Retroviruses require proteasome activity for processing of the Gag protein for efficient release of viral progeny. Transcriptional activation of herpesvirus VP16 also requires proteasome activity. Human papilloma virus E6 protein interacts with ubiquitin ligase E6-associated protein and target p53 for degradation, preventing apoptosis. The UPS facilitates entry of influenza virus into host cells. Inhibition of proteasome activity markedly reduces coxsackievirus (CVB3) RNA and protein levels.

In general, inhibiting USP14 is not toxic to cells, nor are USP14-null murine embryonic fibroblasts compromised in viability. There exists a need for antiviral therapies that are not detrimental to host cell viability.

SUMMARY

In certain embodiments, the invention relates to a method of treating or preventing a viral infection in a subject comprising administering to the subject an effective amount of a compound, or a pharmaceutically acceptable salt, solvate, hydrate, prodrug, chemically-protected form, enantiomer or stereoisomer thereof, wherein the compound is represented by Formula I

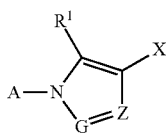

wherein, independently for each occurrence,

A is aryl, heteroaryl, carbocyclyl, heterocyclyl, or biaryl;
$R^1$ is hydrogen, alkyl, haloalkyl, fluoroalkyl, lower alkoxy, halo or trifluoromethyl;
G is —N= or —C($R^2$)=;
Z is =C($R^8$)—, =C($R^2$)— or =N—;
$R^2$ is hydrogen, alkyl, haloalkyl, fluoroalkyl, lower alkoxy, halo or trifluoromethyl; or, when G is —C($R^2$)= and Z is =C($R^2$)—, the two $R^2$ taken together are

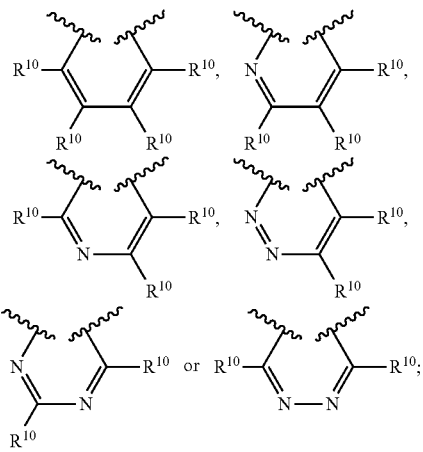

X is

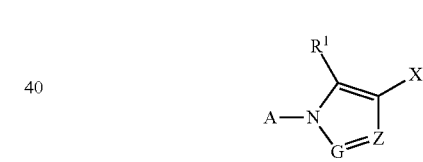

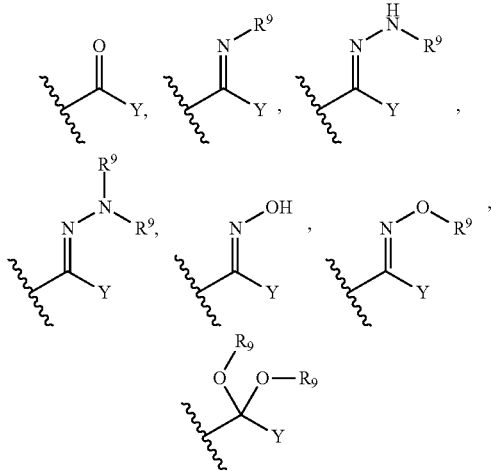

or heteroaryl;

Y is —$CH_2NR^3R^4$, —$CH_2$(N-heterocyclyl), —$CH_2NH(CH_2)_nNH(alkyl)$, —$CH_2NH(CH_2)_nN(alkyl)_2$, —$CH_2NH(CH_2)_n$(N-heterocyclyl), —$CH_2N(alkyl)(CH_2)_nNH(alkyl)$, —$CH_2N(alkyl)(CH_2)_nN(alkyl)_2$, —$CH_2N(alkyl)(CH_2)_n$(N-heterocyclyl), —$CH_2NH(CH_2)_nO(alkyl)$, —$CH_2N(alkyl)(CH_2)_nO(alkyl)$, —$NR^3R^4$, —$NR^5NR^6R^7$, —$NR^5$(N-heterocyclyl), or —N-heterocyclyl;

n is 1, 2, 3 or 4;
$R^3$ is hydrogen, alkyl, substituted alkyl, alkoxyalkyl, haloalkyl, fluoroalkyl, aryl, aralkyl, heteroaryl, or heteroaralkyl;
$R^4$ is hydrogen, alkyl, substituted alkyl, alkoxyalkyl, haloalkyl, fluoroalkyl, aryl, aralkyl, heteroaryl, or heteroaralkyl;
$R^5$ is hydrogen, alkyl, substituted alkyl, alkoxyalkyl, haloalkyl, fluoroalkyl, aryl, aralkyl, heteroaryl, or heteroaralkyl;
$R^6$ is hydrogen, alkyl, substituted alkyl, alkoxyalkyl, haloalkyl, fluoroalkyl, aryl, aralkyl, heteroaryl, or heteroaralkyl;
$R^7$ is hydrogen, alkyl, substituted alkyl, alkoxyalkyl, haloalkyl, fluoroalkyl, aryl, aralkyl, heteroaryl, or heteroaralkyl;
$R^8$ is hydrogen, alkyl, substituted alkyl, alkoxyalkyl, haloalkyl, fluoroalkyl, aryl, aralkyl, heteroaryl, or heteroaralkyl;
$R^9$ is alkyl; or two $R^9$ taken together with the nitrogen to which they are bound are an N-heterocyclyl group; and
$R^{10}$ is hydrogen, alkyl, haloalkyl, fluoroalkyl, alkoxy, alkoxyalkyl, halo, trifluoromethyl, sulfoxymethyl, sulfonamido, amino, amido, N-heterocyclyl, aminoalkyl, amidoalkyl, or N-heterocyclylalkyl.

In certain embodiments, the invention relates to any one of the aforementioned methods, wherein the viral infection is a result of enveloped virus.

In certain embodiments, the invention relates to a method of inhibiting replication of a virus in a host cell comprising contacting the host cell with an effective amount of a compound, or a pharmaceutically acceptable salt, solvate, hydrate, prodrug, chemically-protected form, enantiomer or stereoisomer thereof, wherein the compound is represented by Formula I

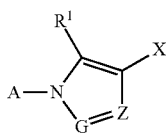

wherein, independently for each occurrence,

A is aryl, heteroaryl, carbocyclyl, heterocyclyl, or biaryl;
$R^1$ is hydrogen, alkyl, haloalkyl, fluoroalkyl, lower alkoxy, halo or trifluoromethyl;
G is —N= or —C($R^2$)=;
Z is =C($R^8$)—, =C($R^2$)— or =N—;
$R^2$ is hydrogen, alkyl, haloalkyl, fluoroalkyl, lower alkoxy, halo or trifluoromethyl; or, when G is —C($R^2$)=and Z is =C($R^2$)—, the two $R^2$ taken together are

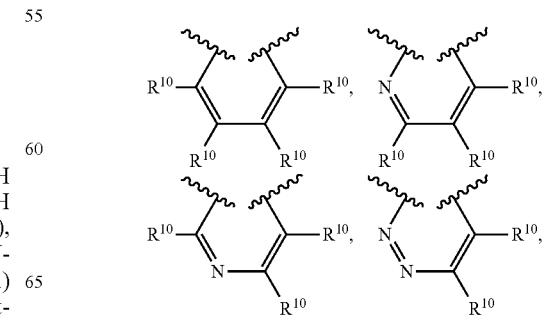

-continued

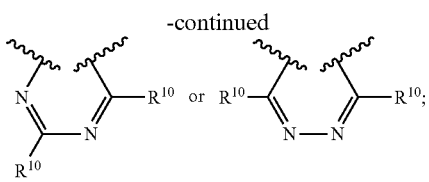

X is

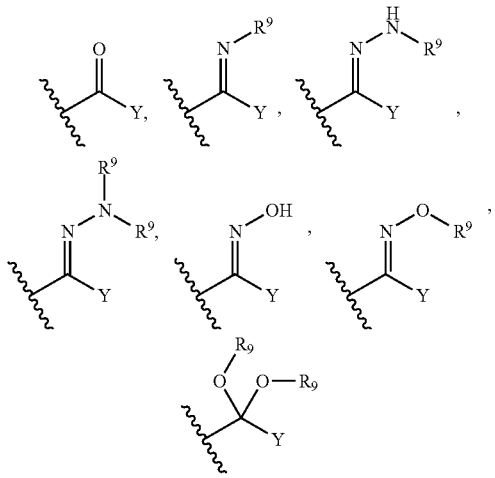

or heteroaryl;

Y is —CH$_2$NR$^3$R$^4$, —CH$_2$(N-heterocyclyl), —CH$_2$NH(CH$_2$)$_n$NH(alkyl), —CH$_2$NH(CH$_2$)$_n$N(alkyl)$_2$, —CH$_2$NH(CH$_2$)$_n$(N-heterocyclyl), —CH$_2$N(alkyl)(CH$_2$)$_n$NH(alkyl), —CH$_2$N(alkyl)(CH$_2$)N(alkyl)$_2$, —CH$_2$N(alkyl)(CH$_2$)$_n$(N-heterocyclyl), —CH$_2$NH(CH$_2$)$_n$O(alkyl), —CH$_2$N(alkyl)(CH$_2$)$_n$O(alkyl), —NR$^3$R$^4$, —NR$^5$NR$^6$R$^7$, —NR$^5$(N-heterocyclyl), or -N-heterocyclyl;

n is 1, 2, 3 or 4;

R$^3$ is hydrogen, alkyl, substituted alkyl, alkoxyalkyl, haloalkyl, fluoroalkyl, aryl, aralkyl, heteroaryl, or heteroaralkyl;

R$^4$ is hydrogen, alkyl, substituted alkyl, alkoxyalkyl, haloalkyl, fluoroalkyl, aryl, aralkyl, heteroaryl, or heteroaralkyl;

R$^5$ is hydrogen, alkyl, substituted alkyl, alkoxyalkyl, haloalkyl, fluoroalkyl, aryl, aralkyl, heteroaryl, or heteroaralkyl;

R$^6$ is hydrogen, alkyl, substituted alkyl, alkoxyalkyl, haloalkyl, fluoroalkyl, aryl, aralkyl, heteroaryl, or heteroaralkyl;

R$^7$ is hydrogen, alkyl, substituted alkyl, alkoxyalkyl, haloalkyl, fluoroalkyl, aryl, aralkyl, heteroaryl, or heteroaralkyl;

R$^8$ is hydrogen, alkyl, substituted alkyl, alkoxyalkyl, haloalkyl, fluoroalkyl, aryl, aralkyl, heteroaryl, or heteroaralkyl;

R$^9$ is alkyl; or two R$^9$ taken together with the nitrogen to which they are bound are an N-heterocyclyl group; and R$^{10}$ is hydrogen, alkyl, haloalkyl, fluoroalkyl, alkoxy, alkoxyalkyl, halo, trifluoromethyl, sulfoxymethyl, sulfonamido, amino, amido, N-heterocyclyl, aminoalkyl, amidoalkyl, or N-heterocyclylalkyl.

In certain embodiments, the invention relates to any one of the aforementioned methods, wherein the virus in an enveloped virus.

In certain embodiments, the invention relates to any one of the aforementioned methods, wherein the virus is of family Flaviviridae.

In certain embodiments, the invention relates to a pharmaceutical composition for use in treating or preventing viral infections in vitro or in vivo, wherein the composition comprises a pharmaceutically acceptable carrier and a compound; and the compound is represented by Formula I

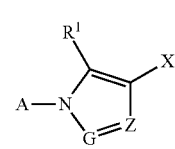

I wherein, independently for each occurrence,

A is aryl, heteroaryl, carbocyclyl, heterocyclyl, or biaryl;

R$^1$ is hydrogen, alkyl, haloalkyl, fluoroalkyl, lower alkoxy, halo or trifluoromethyl;

G is —N= or —C(R$^2$)=;

Z is =C(R$^8$)—, =C(R$^2$)— or =N—;

R$^2$ is hydrogen, alkyl, haloalkyl, fluoroalkyl, lower alkoxy, halo or trifluoromethyl; or, when G is —C(R$^2$)= and Z is =C(R$^2$)—, the two R$^2$ taken together are

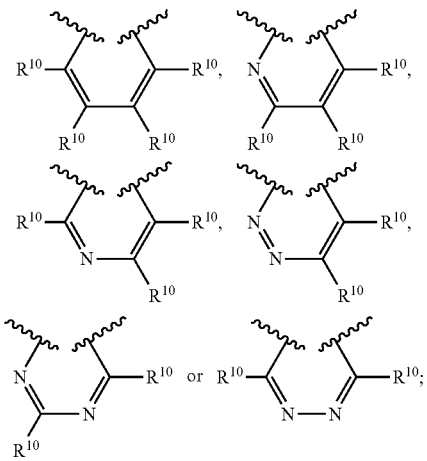

X is

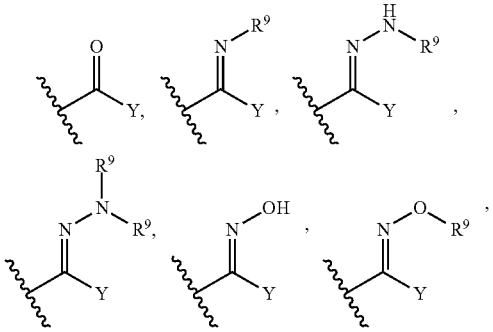

-continued

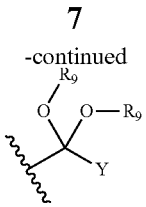

or heteroaryl;

Y is —CH$_2$NR$^3$R$^4$, —CH$_2$(N-heterocyclyl), —CH$_2$NH(CH$_2$)$_n$NH(alkyl), —CH$_2$NH(CH$_2$)$_n$N(alkyl)$_2$, —CH$_2$NH(CH$_2$)$_n$(N-heterocyclyl), —CH$_2$N(alkyl)(CH$_2$)$_n$NH(alkyl), —CH$_2$N(alkyl)(CH$_2$)$_2$N(alkyl)$_2$, —CH$_2$N(alkyl)(CH$_2$)$_n$(N-heterocyclyl), —CH$_2$NH(CH$_2$)$_n$O(alkyl), —CH$_2$N(alkyl)(CH$_2$)$_n$O(alkyl), —NR$^3$R$^4$, —NR$^5$NR$^6$R$^7$, —NR$^5$(N-heterocyclyl), or —N-heterocyclyl;

n is 1, 2, 3 or 4;

R$^3$ is hydrogen, alkyl, substituted alkyl, alkoxyalkyl, haloalkyl, fluoroalkyl, aryl, aralkyl, heteroaryl, or heteroaralkyl;

R$^4$ is hydrogen, alkyl, substituted alkyl, alkoxyalkyl, haloalkyl, fluoroalkyl, aryl, aralkyl, heteroaryl, or heteroaralkyl;

R$^5$ is hydrogen, alkyl, substituted alkyl, alkoxyalkyl, haloalkyl, fluoroalkyl, aryl, aralkyl, heteroaryl, or heteroaralkyl;

R$^6$ is hydrogen, alkyl, substituted alkyl, alkoxyalkyl, haloalkyl, fluoroalkyl, aryl, aralkyl, heteroaryl, or heteroaralkyl;

R$^7$ is hydrogen, alkyl, substituted alkyl, alkoxyalkyl, haloalkyl, fluoroalkyl, aryl, aralkyl, heteroaryl, or heteroaralkyl;

R$^8$ is hydrogen, alkyl, substituted alkyl, alkoxyalkyl, haloalkyl, fluoroalkyl, aryl, aralkyl, heteroaryl, or heteroaralkyl;

R$^9$ is alkyl; or two R$^9$ taken together with the nitrogen to which they are bound are an N-heterocyclyl group; and R$^{10}$ is hydrogen, alkyl, haloalkyl, fluoroalkyl, alkoxy, alkoxyalkyl, halo, trifluoromethyl, sulfoxymethyl, sulfonamido, amino, amido, N-heterocyclyl, aminoalkyl, amidoalkyl, or N-heterocyclylalkyl.

DETAILED DESCRIPTION

Overview

Figure 1:
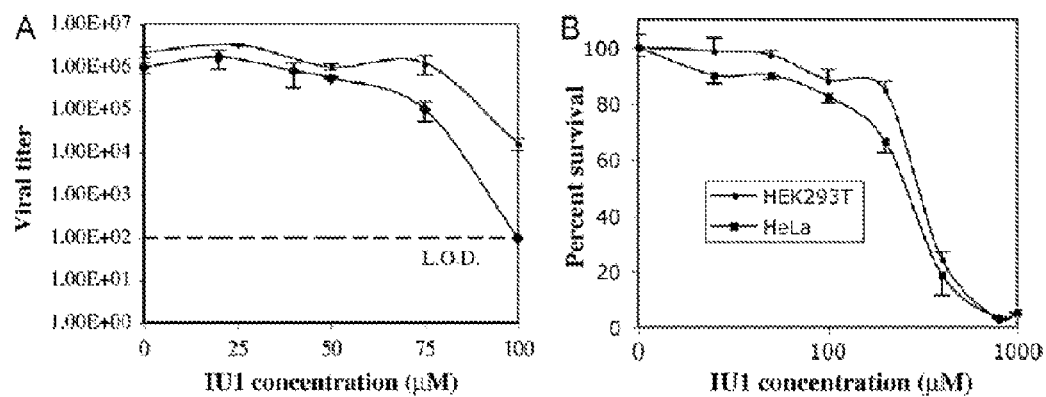
FIG. 1 depicts the effects of IU1 on DENV2 replication. (A) DENV2 titer in the presence of various concentrations of IU1. (♦) Cells preincubated with IU1; (●) IU1 added immediately following infection. The dotted line represents the limit of detection (L.O.D.) of the plaque assay. (B) MTT-based cytotoxicity assay. Mean of three replicates are presented. Error bars represent standard deviations.

In certain embodiment, the invention relates to the effect of small molecules on viral replication. The ubiquitin-proteasome system (UPS) is a key player in maintaining cellular protein homeostasis and is associated with various human diseases, including neurodegenerative disorders, cancer, and infectious diseases. Viruses from several families reprogram the UPS to make the cellular environment conducive to viral replication, and inhibition of the UPS interferes with viral propagation. In certain embodiments, the invention relates to a method of inhibiting replication of a flavivirus comprising contacting a cell with an effective amount of a compound that enhances protein degradation. In certain embodiments, the invention relates to a method of inhibiting replication of a flavivirus comprising contacting a cell with an effective amount of a small-molecule inhibitor of the proteasome-associated deubiquitinating enzyme USP14. IU1, or 1-(1-(4-fluorophenyl)-2,5-dimethyl-1H-pyrrol-3-yl)-2-(pyrrolidin-1-yl)ethanone, has been shown to enhance proteasome activity, an effect that may underlie its influence on flavivirus propagation. These results open new targets for therapeutic intervention against viruses from multiple families.

In certain embodiments, the invention relates to the finding that components of the UPS can be targeted for antiviral drug development. Since viruses from multiple families utilize the UPS, in certain embodiments, the invention relates to a broad-spectrum antiviral resulting from this approach.

Definitions

In order for the invention to be more readily understood, certain terms and phrases are defined below and throughout the specification.

The articles "a" and "an" are used herein to refer to one or to more than one (i.e., to at least one) of the grammatical object of the article. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The definition of each expression, e.g., alkyl, m, n, and the like, when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., a compound which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein below. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The term "lower" when appended to any of the groups listed below indicates that the group contains less than seven carbons (i.e. six carbons or less). For example "lower alkyl" refers to an alkyl group containing 1-6 carbons, and "lower alkenyl" refers to an alkenyl group containing 2-6 carbons.

The term "saturated," as used herein, pertains to compounds and/or groups which do not have any carbon-carbon double bonds or carbon-carbon triple bonds.

The term "unsaturated," as used herein, pertains to compounds and/or groups which have at least one carbon-carbon double bond or carbon-carbon triple bond.

The term "aliphatic," as used herein, pertains to compounds and/or groups which are linear or branched, but not cyclic (also known as "acyclic" or "open-chain" groups).

The term "cyclic," as used herein, pertains to compounds and/or groups which have one ring, or two or more rings (e.g., spiro, fused, bridged).

The term "aromatic" refers to a planar or polycyclic structure characterized by a cyclically conjugated molecular moiety containing 4n+2 electrons, wherein n is the absolute value of an integer. Aromatic molecules containing fused, or joined, rings also are referred to as bicyclic aromatic rings. For example, bicyclic aromatic rings containing heteroatoms in a hydrocarbon ring structure are referred to as bicyclic heteroaryl rings.

The term "hydrocarbon" as used herein refers to an organic compound consisting entirely of hydrogen and carbon.

For purposes of this invention, the chemical elements are identified in accordance with the Periodic Table of the Elements, CAS version, Handbook of Chemistry and Physics, 67th Ed., 1986-87, inside cover.

The term "heteroatom" as used herein is art-recognized and refers to an atom of any element other than carbon or hydrogen. Illustrative heteroatoms include boron, nitrogen, oxygen, phosphorus, sulfur and selenium.

The term "alkyl" means an aliphatic or cyclic hydrocarbon radical containing from 1 to 12 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 2-methylcyclopentyl, and 1-cyclohexylethyl.

The term "substituted alkyl" means an aliphatic or cyclic hydrocarbon radical containing from 1 to 12 carbon atoms, substituted with 1, 2, 3, 4, or 5 substituents independently selected from the group consisting of alkyl, alkenyl, alkynyl, halo, haloalkyl, fluoroalkyl, hydroxy, alkoxy, alkenyloxy, alkynyloxy, carbocyclyloxy, heterocyclyloxy, haloalkoxy, fluoroalkyloxy, sulfhydryl, alkylthio, haloalkylthio, fluoroalkylthio, alkenylthio, alkynylthio, sulfonic acid, alkylsulfonyl, haloalkylsulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfonyl, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, haloalkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, haloalkylsulfinyloxy, fluoroalkylsulfinyloxy, alkenylsulfinyloxy, alkynylsulfinyloxy, alkoxysulfinyloxy, haloalkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl and silyloxy.

The term "alkylene" is art-recognized, and as used herein pertains to a bidentate moiety obtained by removing two hydrogen atoms of an alkyl group, as defined above.

The term "alkenyl" as used herein means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkynyl" as used herein means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "carbocyclyl" as used herein means monocyclic or multicyclic (e.g., bicyclic, tricyclic, etc.) hydrocarbons containing from 3 to 12 carbon atoms that is completely saturated or has one or more unsaturated bonds, and for the avoidance of doubt, the degree of unsaturation does not result in an aromatic ring system (e.g. phenyl). Examples of carbocyclyl groups include 1-cyclopropyl, 1-cyclobutyl, 2-cyclopentyl, 1-cyclopentenyl, 3-cyclohexyl, 1-cyclohexenyl and 2-cyclopentenylmethyl.

The term "heterocyclyl", as used herein include non-aromatic, ring systems, including, but not limited to, monocyclic, bicyclic (e.g. fused and spirocyclic) and tricyclic rings, which can be completely saturated or which can contain one or more units of unsaturation, for the avoidance of doubt, the degree of unsaturation does not result in an aromatic ring system, and have 3 to 12 atoms including at least one heteroatom, such as nitrogen, oxygen, or sulfur. For purposes of exemplification, which should not be construed as limiting the scope of this invention, the following are examples of heterocyclic rings: azepines, azetidinyl, morpholinyl, oxopiperidinyl, oxopyrrolidinyl, piperazinyl, piperidinyl, pyrrolidinyl, quinicludinyl, thiomorpholinyl, tetrahydropyranyl and tetrahydrofuranyl. The heterocyclyl groups of the invention are substituted with 0, 1, 2, 3, 4 or 5 substituents independently selected from the group consisting of alkyl, alkenyl, alkynyl, halo, haloalkyl, fluoroalkyl, hydroxy, alkoxy, alkenyloxy, alkynyloxy, carbocyclyloxy, heterocyclyloxy, haloalkoxy, fluoroalkyloxy, sulfhydryl, alkylthio, haloalkylthio, fluoroalkylthio, alkenylthio, alkynylthio, sulfonic acid, alkylsulfonyl, haloalkylsulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfonyl, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfinyl, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, haloalkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, haloalkylsulfinyloxy, fluoroalkylsulfinyloxy, alkenylsulfinyloxy, alkynylsulfinyloxy, alkoxysulfinyloxy, haloalkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substituents bound to the heterocyclyl group through an alkylene moiety (e.g. methylene).

The term "N-heterocyclyl" as used herein is a subset of heterocyclyl, as defined herein, which have at least one nitrogen atom through which the N-heterocyclyl moiety is bound to the parent moiety. Representative examples include pyrrolidin-1-yl, piperidin-1-yl, piperazin-1-yl, hexahydropyrimidin-1-yl, morpholin-1-yl, 1,3-oxazinan-3-yl and 6- azaspiro[2.5]oct-6-yl. As with the heterocyclyl groups, the N-heterocyclyl groups of the invention are substituted with 0, 1, 2, 3, 4 or 5 substituents independently selected from the group consisting of alkyl, alkenyl, alkynyl, halo, haloalkyl, fluoroalkyl, hydroxy, alkoxy, alkenyloxy, alkynyloxy, carbocyclyloxy, heterocyclyloxy, haloalkoxy, fluoroalkyloxy, sulfhydryl, alkylthio, haloalkylthio, fluoroalkylthio, alkyenylthio, alkynylthio, sulfonic acid, alkylsulfonyl, haloalkylsulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfonyl, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfinyl, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, halo alkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, haloalkylsulfinyloxy, fluoroalkylsulfinyloxy, alkenylsulfinyloxy, alkynylsulfinyloxy, alkoxysulfinyloxy, haloalkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substituents bound to the N-heterocyclyl group through an alkylene moiety (e.g. methylene).

The term "aryl," as used herein means a phenyl group, naphthyl or anthracenyl group. The aryl groups of the invention can be optionally substituted with 1, 2, 3, 4 or 5 substituents independently selected from the group consisting of alkyl, alkenyl, alkynyl, halo, haloalkyl, fluoroalkyl, hydroxy, alkoxy, alkenyloxy, alkynyloxy, carbocyclyloxy, heterocyclyloxy, haloalkoxy, fluoroalkyloxy, sulfhydryl, alkylthio, haloalkylthio, fluoroalkylthio, alkenylthio, alkynylthio, sulfonic acid, alkylsulfonyl, haloalkylsulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfonyl, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfinyl, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, haloalkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, haloalkylsulfinyloxy, fluoroalkylsulfinyloxy, alkenylsulfinyloxy, alkynylsulfinyloxy, alkoxysulfinyloxy, haloalkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substituents bound to the heterocyclyl group through an alkylene moiety (e.g. methylene).

The term "arylene," is art-recognized, and as used herein pertains to a bidentate moiety obtained by removing two hydrogen atoms of an aryl ring, as defined above.

The term "arylalkyl" or "aralkyl" as used herein means an aryl group, as defined herein, appended to the parent molecular moiety through an alkyl group, as defined herein. Representative examples of aralkyl include, but are not limited to, benzyl, 2-phenylethyl, 3-phenylpropyl, and 2-naphth-2-ylethyl.

The term "biaryl," as used herein means an aryl-substituted aryl, an aryl-substituted heteroaryl, a heteroaryl-substituted aryl or a heteroaryl-substituted heteroaryl, wherein aryl and heteroaryl are as defined herein. Representative examples include 4-(phenyl)phenyl and 4-(4-fluorophenyl)pyridinyl.

The term "heteroaryl" as used herein include aromatic ring systems, including, but not limited to, monocyclic, bicyclic and tricyclic rings, and have 3 to 12 atoms including at least one heteroatom, such as nitrogen, oxygen, or sulfur. For purposes of exemplification, which should not be construed as limiting the scope of this invention: azaindolyl, benzo(b)thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl. The heteroaryl groups of the invention are substituted with 0, 1, 2, 3, 4 or 5 substituents independently selected from the group consisting of alkyl, alkenyl, alkynyl, halo, haloalkyl, fluoroalkyl, hydroxy, alkoxy, alkenyloxy, alkynyloxy, carbocyclyloxy, heterocyclyloxy, haloalkoxy, fluoroalkyloxy, sulfhydryl, alkylthio, haloalkylthio, fluoroalkylthio, alkenylthio, alkynylthio, sulfonic acid, alkylsulfonyl, haloalkylsulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfonyl, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfinyl, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, haloalkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, haloalkylsulfinyloxy, fluoroalkylsulfinyloxy, alkenylsulfinyloxy, alkynylsulfinyloxy, alkoxysulfinyloxy, haloalkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substituents bound to the heteroaryl group through an alkylene moiety (e.g. methylene).

The term "heteroarylene," is art-recognized, and as used herein pertains to a bidentate moiety obtained by removing two hydrogen atoms of a heteroaryl ring, as defined above.

The term "heteroarylalkyl" or "heteroaralkyl" as used herein means a heteroaryl, as defined herein, appended to the parent molecular moiety through an alkyl group, as defined herein. Representative examples of heteroarylalkyl include, but are not limited to, pyridine-3-ylmethyl and 2-(thien-2-yl)ethyl.

The term "halo" or "halogen" means —Cl, —Br, —I or —F.

The term "haloalkyl" means an alkyl group, as defined herein, wherein at least one hydrogen is replaced with a halogen, as defined herein. Representative examples of haloalkyl include, but are not limited to, chloromethyl, 2-fluoroethyl, trifluoromethyl, pentafluoroethyl, and 2-chloro-3-fluoropentyl.

The term "fluoroalkyl" means an alkyl group, as defined herein, wherein all the hydrogens are replaced with fluorines.

The term "hydroxy" as used herein means an —OH group.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy. The terms "alkenyloxy", "alkynyloxy", "carbocyclyloxy", and "heterocyclyloxy" are likewise defined.

The term "haloalkoxy" as used herein means an alkoxy group, as defined herein, wherein at least one hydrogen is replaced with a halogen, as defined herein. Representative examples of haloalkoxy include, but are not limited to, chloromethoxy, 2-fluoroethoxy, trifluoromethoxy, and pentafluoroethoxy. The term "fluoroalkyloxy" is likewise defined.

The term "aryloxy" as used herein means an aryl group, as defined herein, appended to the parent molecular moiety through an oxygen. The term "heteroaryloxy" as used herein means a heteroaryl group, as defined herein, appended to the parent molecular moiety through an oxygen. The terms "heteroaryloxy" is likewise defined.

The term "arylalkoxy" or "arylalkyloxy" as used herein means an arylalkyl group, as defined herein, appended to the parent molecular moiety through an oxygen. The term "heteroarylalkoxy" is likewise defined. Representative examples of aryloxy and heteroarylalkoxy include, but are not limited to, 2-chlorophenylmethoxy, 3-trifluoromethylphenylethoxy, and 2,3-dimethylpyridinylmethoxy.

The term "sulfhydryl" or "thio" as used herein means a —SH group.

The term "alkylthio" as used herein means an alkyl group, as defined herein, appended to the parent molecular moiety through a sulfur. Representative examples of alkylthio include, but are not limited, methylthio, ethylthio, tert-butylthio, and hexylthio. The terms "haloalkylthio", "fluoroalkylthio", "alkenylthio", "alkynylthio", "carbocyclylthio", and "heterocyclylthio" are likewise defined.

The term "arylthio" as used herein means an aryl group, as defined herein, appended to the parent molecular moiety through an sulfur. The term "heteroarylthio" is likewise defined.

The term "arylalkylthio" or "aralkylthio" as used herein means an arylalkyl group, as defined herein, appended to the parent molecular moiety through an sulfur. The term "heteroarylalkylthio" is likewise defined.

The term "sulfonyl" as used herein refers to —S(=O)$_2$— group.

The term "sulfonic acid" as used herein refers to —S(=O)$_2$OH.

The term "alkylsulfonyl" as used herein means an alkyl group, as defined herein, appended to the parent molecular moiety through a sulfonyl group, as defined herein. Representative examples of alkylsulfonyl include, but are not limited to, methylsulfonyl and ethylsulfonyl. The terms "haloalkylsulfonyl", "fluoroalkylsulfonyl", "alkenylsulfonyl", "alkynylsulfonyl", "carbocyclylsulfonyl", "heterocyclylsulfonyl", "arylsulfonyl", "aralkylsulfonyl", "heteroarylsulfonyl" and "heteroaralkylsulfonyl" are likewise defined.

The term "alkoxysulfonyl" as used herein means an alkoxy group, as defined herein, appended to the parent molecular moiety through a sulfonyl group, as defined herein. Representative examples of alkoxysulfonyl include, but are not limited to, methoxysulfonyl, ethoxysulfonyl and propoxysulfonyl. The terms "haloalkoxysulfonyl", "fluoroalkoxysulfonyl", "alkenyloxysulfonyl", "alkynyloxysulfonyl", "carbocyclyloxysulfonyl", "heterocyclyloxysulfonyl", "aryloxysulfonyl", "aralkyloxysulfonyl", "heteroaryloxysulfonyl" and "heteroaralkyloxysulfonyl" are likewise defined.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The term "aminosulfonyl" as used herein means an amino group, as defined herein, appended to the parent molecular moiety through a sulfonyl group.

The term "sulfinyl" as used herein refers to —S(=O)— group. Sulfinyl groups are as defined above for sulfonyl groups. The term "sulfinic acid" as used herein refers to —S(=O)OH.

The term "oxy" refers to a —O— group.

The term "carbonyl" as used herein means a —C(=O)— group.

The term "thiocarbonyl" as used herein means a —C(=S)— group.

The term "formyl" as used herein means a —C(=O)H group.

The term "alkylcarbonyl" as used herein means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl. The terms "haloalkylcarbonyl", "fluoroalkylcarbonyl", "alkenylcarbonyl", "alkynylcarbonyl", "carbocyclylcarbonyl", "heterocyclylcarbonyl", "arylcarbonyl", "aralkylcarbonyl", "heteroarylcarbonyl", and "heteroaralkylcarbonyl" are likewise defined.

The term "carboxy" as used herein means a —CO$_2$H group.

The term "alkoxycarbonyl" as used herein means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl. The terms "haloalkoxycarbonyl", "fluoroalkoxycarbonyl", "alkenyloxycarbonyl", "alkynyloxycarbonyl", "carbocyclyloxycarbonyl", "heterocyclyloxycarbonyl", "aryloxycarbonyl", "aralkyloxycarbonyl", "heteroaryloxycarbonyl", and "heteroaralkyloxycarbonyl" are likewise defined.

The term "alkylcarbonyloxy" as used herein means an alkylcarbonyl group, as defined herein, appended to the parent molecular moiety through an oxygen atom. Representative examples of alkylcarbonyloxy include, but are not limited to, acetyloxy, ethylcarbonyloxy, and tert—butylcarbonyloxy. The terms "haloalkylcarbonyloxy", "fluoroalkylcarbonyloxy", "alkenylcarbonyloxy", "alkynylcarbonyloxy", "carbocyclylcarbonyloxy", "heterocyclylcarbonyloxy", "arylcarbonyloxy", "aralkylcarbonyloxy", "heteroarylcarbonyloxy", and "heteroaralkylcarbonyloxy" are likewise defined.

The term "alkylsulfonyloxy" as used herein means an alkylsulfonyl group, as defined herein, appended to the parent molecular moiety through an oxygen atom. The terms "haloalkylsulfonyloxy", "fluoroalkylsulfonyloxy", "alkenylsulfonyloxy", "alkynylsulfonyloxy", "carbocyclylsulfonyloxy", "heterocyclylsulfonyloxy", "arylsulfonyloxy", "aralkylsulfonyloxy", "heteroarylsulfonyloxy", "heteroaralkylsulfonyloxy", "haloalkoxysulfonyloxy", "fluoroalkoxysulfonyloxy", "alkenyloxysulfonyloxy", "alkynyloxysulfonyloxy", "carbocyclyloxysulfonyloxy", "heterocyclyloxysulfonyloxy", "aryloxysulfonyloxy", "aralkyloxysulfonyloxy", "heteroaryloxysulfonyloxy" and "heteroaralkyloxysulfonyloxy"

The term "amino" as used herein refers to —NH$_2$ and substituted derivatives thereof wherein one or both of the hydrogens are independently replaced with substituents selected from the group consisting of alkyl, haloalkyl, fluoroalkyl, alkenyl, alkynyl, carbocyclyl, heterocyclyl, aryl, aralkyl, heteroaryl, heteroaralkyl, alkylcarbonyl, haloalkylcarbonyl, fluoroalkylcarbonyl, alkenylcarbonyl, alkynylcarbonyl, carbocyclylcarbonyl, heterocyclylcarbonyl, arylcarbonyl, aralkylcarbonyl, heteroarylcarnbonyl, heteroaralkylcarbonyl and the sufonyl and sulfinyl groups defined above; or when both hydrogens together are replaced with an alkylene group (to form a ring which contains the nitrogen). Representative examples include, but are not limited to methylamino, acetylamino, and dimethylamino.

The term "amido" as used herein means an amino group, as defined herein, appended to the parent molecular moiety through a carbonyl.

The term "cyano" as used herein means a —C≡N group.

The term "nitro" as used herein means a —NO$_2$ group.

The term "azido" as used herein means a —N$_3$ group.

The term "phosphinyl" as used herein includes —PH$_3$ and substituted derivatives thereof wherein one, two or three of the hydrogens are independently replaced with substituents selected from the group consisting of alkyl, haloalkyl, fluoroalkyl, alkenyl, alkynyl, carbocyclyl, heterocyclyl, aryl, aralkyl, heteroaryl, heteroaralkyl, alkoxy, haloalkoxy, fluoroalkyloxy, alkenyloxy, alkynyloxy, carbocyclyloxy, heterocyclyloxy, aryloxy, aralkyloxy, heteroaryloxy, heteroaralkyloxy, and amino.

The term "phosphoryl" as used herein refers to —P(=O)OH$_2$ and substituted derivatives thereof wherein one or both of the hydroxyls are independently replaced with substituents selected from the group consisting of alkyl, haloalkyl, fluoroalkyl, alkenyl, alkynyl, carbocyclyl, heterocyclyl, aryl, aralkyl, heteroaryl, heteroaralkyl, alkoxy, haloalkoxy, fluoroalkyloxy, alkenyloxy, alkynyloxy, carbocyclyloxy, heterocyclyloxy, aryloxy, aralkyloxy, heteroaryloxy, heteroaralkyloxy, and amino.

The term "silyl" as used herein includes H$_3$Si— and substituted derivatives thereof wherein one, two or three of the hydrogens are independently replaced with substituents selected from alkyl, haloalkyl, fluoroalkyl, alkenyl, alkynyl, carbocyclyl, heterocyclyl, aryl, aralkyl, heteroaryl, and heteroaralkyl. Representative examples include trimethylsilyl (TMS), tert-butyldiphenylsilyl (TBDPS), tert-butyldimethylsilyl (TBS/TBDMS), triisopropylsilyl (TIPS), and [2-(trimethylsilyl)ethoxy]methyl (SEM).

The term "silyloxy" as used herein means a silyl group, as defined herein, is appended to the parent molecule through an oxygen atom.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled Standard List of Abbreviations.

As used herein, the term "administering" means providing a pharmaceutical agent or composition to a subject, and includes, but is not limited to, administering by a medical professional and self-administering.

As used herein, the phrase "pharmaceutically acceptable" refers to those agents, compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the phrase "pharmaceutically-acceptable carrier" means a pharmaceutically-acceptable material, composition or vehicle, such as a liquid or solid filler, diluent, excipient, or solvent encapsulating material, involved in carrying or transporting an agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As used herein, the phrase "pharmaceutically-acceptable salts" refers to the relatively non-toxic, inorganic and organic salts of compounds.

The term "viral infection" as used herein refers to infection by a viral pathogen wherein there is clinical evidence of the infection based on symptoms or based on the demonstration of the presence of the viral pathogen in a biological sample from the individual. As used herein an "individual" refers to an animal, preferably a mammal, including both non-human mammals and humans, and more preferably, refers to a human.

"Treatment of a viral infection" as used herein encompasses alleviating, reducing the frequency of, or eliminating one or more symptoms of the infection and/or a reducing the viral load.

As used herein, the term "subject" means a human or non-human animal selected for treatment or therapy.

As used herein, the phrase "subject suspected of having" means a subject exhibiting one or more clinical indicators of a disease or condition.

As used herein, the phrase "subject in need thereof" means a subject identified as in need of a therapy or treatment of the invention.

As used herein, the phrase "therapeutic effect" refers to a local or systemic effect in animals, particularly mammals, and more particularly humans, caused by an agent. The phrases "therapeutically-effective amount" and "effective amount" mean the amount of an agent that produces some therapeutically useful effect on the symptoms of the viral infection and/or a reduction in viral load. A therapeutically effective amount includes an amount of an agent that produces some desired local or systemic effect at a reasonable benefit/risk ratio applicable to any treatment. For example, certain agents used in the methods of the invention may be administered in a sufficient amount to produce a reasonable benefit/risk ratio applicable to such treatment.

As used herein, the term "treating" a disease in a subject or "treating" a subject having or suspected of having a disease refers to subjecting the subject to a pharmaceutical treatment, e.g., the administration of an agent, such that at least one symptom of the disease is decreased or prevented from worsening.

As used herein, the phrase "inhibiting replication" means to reduce replication of a virus in a host cell by about 20%, about 30%, about 40%, about 50%, about 60%, about 70%, about 80%, about 90%, or about 95%, in comparison to an untreated cell. In certain embodiments, "inhibiting replication" means to reduce replication of a virus in a host cell by at least about 50%, in comparison to an untreated cell.

Therapeutic Methods of the Invention

In certain embodiments, the invention relates to a method of treating or preventing a viral infection in a subject comprising administering to the subject, (e.g., a subject in need thereof), an effective amount of a compound, or a pharmaceutically acceptable salt, solvate, hydrate, prodrug, chemically-protected form, enantiomer or stereoisomer thereof, wherein the compound is represented by Formula I

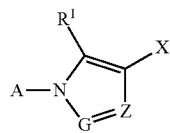

wherein, independently for each occurrence,

A is aryl, heteroaryl, carbocyclyl, heterocyclyl, or biaryl;

$R^1$ is hydrogen, alkyl, haloalkyl, fluoroalkyl, lower alkoxy, halo or trifluoromethyl;

G is —N═ or —C($R^2$)═;

Z is ═C($R^8$)—, ═C($R^2$)— or ═N—;

$R^2$ is hydrogen, alkyl, haloalkyl, fluoroalkyl, lower alkoxy, halo or trifluoromethyl; or, when G is —C($R^2$)═ and Z is ═C($R^2$)—, the two $R^2$ taken together are

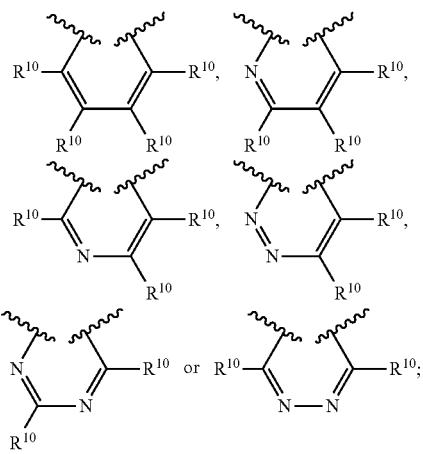

X is

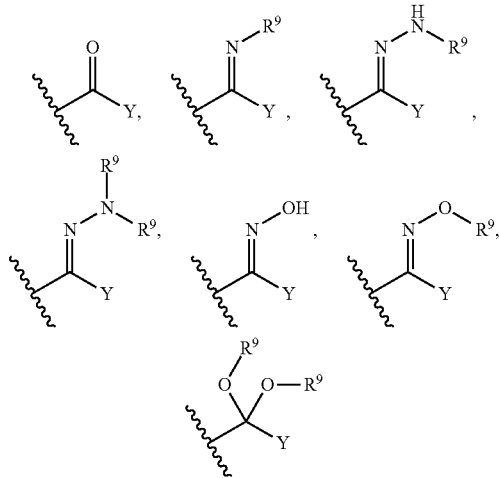

or heteroaryl;

Y is —$CH_2NR^3R^4$, —$CH_2$(N-heterocyclyl), —$CH_2NH(CH_2)_nNH$(alkyl), —$CH_2NH(CH_2)_nN$(alkyl)$_2$, —$CH_2NH(CH_2)_n$(N-heterocyclyl), —$CH_2N$(alkyl)$(CH_2)_n NH$(alkyl), —$CH_2N$(alkyl)$(CH_2)_2N$(alkyl)$_2$, —$CH_2N$(alkyl)$(CH_2)_n$(N-heterocyclyl), —$CH_2NH(CH_2)_nO$(alkyl), —$CH_2N$(alkyl)$(CH_2)_nO$(alkyl), —$NR^3R^4$, —$NR^5NR^6R^7$, —$NR^5$(N-heterocyclyl), or —N-heterocyclyl;

n is 1, 2, 3 or 4;

$R^3$ is hydrogen, alkyl, substituted alkyl, alkoxyalkyl, haloalkyl, fluoroalkyl, aryl, aralkyl, heteroaryl, or heteroaralkyl;

$R^4$ is hydrogen, alkyl, substituted alkyl, alkoxyalkyl, haloalkyl, fluoroalkyl, aryl, aralkyl, heteroaryl, or heteroaralkyl;

$R^5$ is hydrogen, alkyl, substituted alkyl, alkoxyalkyl, haloalkyl, fluoroalkyl, aryl, aralkyl, heteroaryl, or heteroaralkyl;

$R^6$ is hydrogen, alkyl, substituted alkyl, alkoxyalkyl, haloalkyl, fluoroalkyl, aryl, aralkyl, heteroaryl, or heteroaralkyl;

$R^7$ is hydrogen, alkyl, substituted alkyl, alkoxyalkyl, haloalkyl, fluoroalkyl, aryl, aralkyl, heteroaryl, or heteroaralkyl;

$R^8$ is hydrogen, alkyl, substituted alkyl, alkoxyalkyl, haloalkyl, fluoroalkyl, aryl, aralkyl, heteroaryl, or heteroaralkyl;

$R^9$ is alkyl; or two $R^9$ taken together with the nitrogen to which they are bound are an N-heterocyclyl group; and $R^{10}$ is hydrogen, alkyl, haloalkyl, fluoroalkyl, alkoxy, alkoxyalkyl, halo, trifluoromethyl, sulfoxymethyl, sulfonamido, amino, amido, N-heterocyclyl, aminoalkyl, amidoalkyl, or N-heterocyclylalkyl.

In certain embodiments, the invention relates to any of the aforementioned methods, wherein the compound is administered to the subject before exposure to a virus; and the virus causes the viral infection.

In certain embodiments, the invention relates to any of the aforementioned methods, wherein the compound is administered to the subject after exposure to a virus; and the virus causes the viral infection.

In certain embodiments, the invention relates to a method of inhibiting replication of a virus in a host cell comprising contacting the host cell with an effective amount of a compound, or a pharmaceutically acceptable salt, solvate, hydrate, prodrug, chemically-protected form, enantiomer or stereoisomer thereof, wherein the compound is represented by Formula I

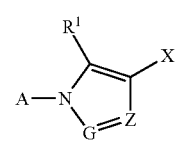

wherein, independently for each occurrence,

A is aryl, heteroaryl, carbocyclyl, heterocyclyl, or biaryl;

$R^1$ is hydrogen, alkyl, haloalkyl, fluoroalkyl, lower alkoxy, halo or trifluoromethyl;

G is —N═ or —C($R^2$)═;

Z is ═C($R^8$)—, ═C($R^2$)— or ═N—;

$R^2$ is hydrogen, alkyl, haloalkyl, fluoroalkyl, lower alkoxy, halo or trifluoromethyl; or, when G is —C($R^2$)═ and Z is ═C($R^2$)—, the two $R^2$ taken together are

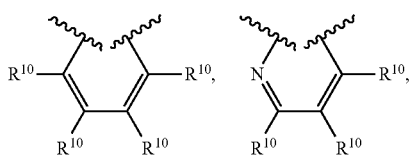

-continued

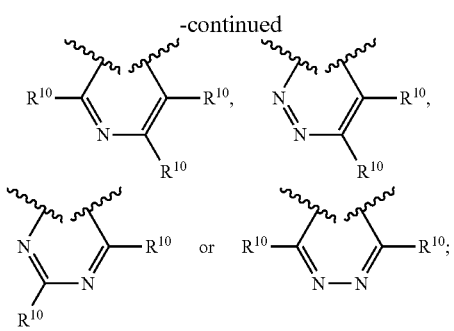

X is

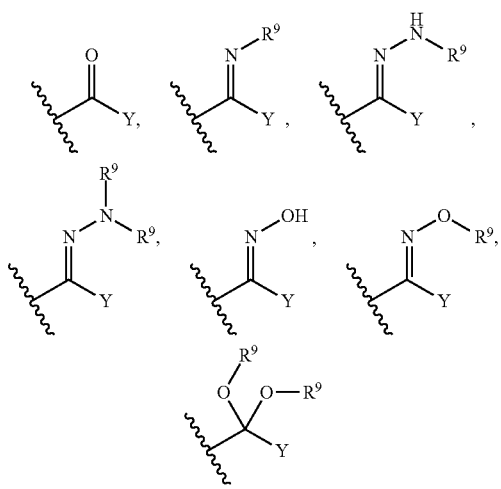

or heteroaryl;

Y is —CH$_2$NR$^3$R$^4$, —CH$_2$(N-heterocyclyl), —CH$_2$NH(CH$_2$)$_n$NH(alkyl), —CH$_2$NH(CH$_2$)$_n$N(alkyl)$_2$, —CH$_2$NH(CH$_2$)$_n$(N-heterocyclyl), —CH$_2$N(alkyl)(CH$_2$)$_n$NH(alkyl), —CH$_2$N(alkyl)(CH$_2$)$_2$N(alkyl)$_2$, —CH$_2$N(alkyl)(CH$_2$)$_n$(N-heterocyclyl), —CH$_2$NH(CH$_2$)$_n$O(alkyl), —CH$_2$N(alkyl)(CH$_2$)$_n$O(alkyl), —NR$^3$R$^4$, —NR$^5$NR$^6$R$^7$, —NR$^5$(N-heterocyclyl), or —N-heterocyclyl;

n is 1, 2, 3 or 4;

R$^3$ is hydrogen, alkyl, substituted alkyl, alkoxyalkyl, haloalkyl, fluoroalkyl, aryl, aralkyl, heteroaryl, or heteroaralkyl;

R$^4$ is hydrogen, alkyl, substituted alkyl, alkoxyalkyl, haloalkyl, fluoroalkyl, aryl, aralkyl, heteroaryl, or heteroaralkyl;

R$^5$ is hydrogen, alkyl, substituted alkyl, alkoxyalkyl, haloalkyl, fluoroalkyl, aryl, aralkyl, heteroaryl, or heteroaralkyl;

R$^6$ is hydrogen, alkyl, substituted alkyl, alkoxyalkyl, haloalkyl, fluoroalkyl, aryl, aralkyl, heteroaryl, or heteroaralkyl;

R$^7$ is hydrogen, alkyl, substituted alkyl, alkoxyalkyl, haloalkyl, fluoroalkyl, aryl, aralkyl, heteroaryl, or heteroaralkyl;

R$^8$ is hydrogen, alkyl, substituted alkyl, alkoxyalkyl, haloalkyl, fluoroalkyl, aryl, aralkyl, heteroaryl, or heteroaralkyl;

R$^9$ is alkyl; or two R$^9$ taken together with the nitrogen to which they are bound are an N-heterocyclyl group; and R$^{10}$ is hydrogen, alkyl, haloalkyl, fluoroalkyl, alkoxy, alkoxyalkyl, halo, trifluoromethyl, sulfoxymethyl, sulfonamido, amino, amido, N-heterocyclyl, aminoalkyl, amidoalkyl, or N-heterocyclylalkyl.

In certain embodiments, the invention relates to any of the aforementioned methods, wherein the host cell is contacted with the compound before exposure to the virus.

In certain embodiments, the invention relates to any of the aforementioned methods, wherein the host cell is contacted with the compound after exposure to the virus.

In certain embodiments, the invention relates to any of the aforementioned methods, wherein G is —N=.

In certain embodiments, the invention relates to any of the aforementioned methods, wherein G is —C(R$^2$)=.

In certain embodiments, the invention relates to any of the aforementioned methods, wherein the compound is represented by Formula II:

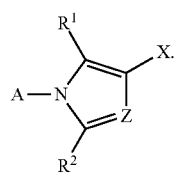

II

In certain embodiments, the invention relates to any of the aforementioned methods, wherein the compound is

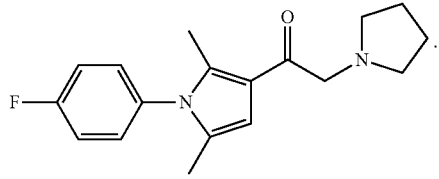 [SMILES: Cc1cc(C(=O)CN2CCCC2)c(C)n1-c1ccc(F)cc1]

In certain embodiments, the invention relates to any of the aforementioned methods, wherein the compound is described in PCT published patent application number WO11/094545, which is incorporated herein by reference in its entirety.

In certain embodiments, the invention relates to any one of the aforementioned methods, wherein the viral infection is a result of a virus of family Flaviviridae.

In certain embodiments, the invention relates to any one of the aforementioned methods, wherein the viral infection is a result of a virus of genus *Flavivirus, Pestivirus*, or *Hepacivirus*. In certain embodiments, the invention relates to any one of the aforementioned methods, wherein the viral infection is a result of a virus of genus *Flavivirus*.

In certain embodiments, the invention relates to any one of the aforementioned methods, wherein the viral infection is selected from the group consisting of: Dengue fever, Japanese encephalitis, Kyasanur Forest disease, Murray Valley encephalitis, St. Louis encephalitis, Tick-borne encephalitis, West Nile encephalitis, Yellow fever, and Hepatitis C.

In certain embodiments, the invention relates to any one of the aforementioned methods, wherein the virus is of family Flaviviridae.

In certain embodiments, the invention relates to any one of the aforementioned methods, wherein the virus is of genus *Flavivirus, Pestivirus*, or *Hepacivirus*. In certain embodiments, the invention relates to any one of the aforementioned methods, wherein the virus is of genus *Flavivirus*.

The methods of the invention are useful for treating a subject in need thereof. A subject in need thereof is a subject having or at risk of having an enveloped virus infection. In its broadest sense, the terms "treatment" or "to treat" refer to both therapeutic and prophylactic treatments. If the subject in need of treatment is experiencing a condition (i.e., has or is having a particular condition), then "treating the condition" refers to ameliorating, reducing or eliminating one or more symptoms arising from the condition. If the subject in need of treatment is one who is at risk of having a condition, then treating the subject refers to reducing the risk of the subject having the condition or, in other words, decreasing the likelihood that the subject will develop an infectious disease to the virus, as well as to a treatment after the subject has been infected in order to fight the infectious disease, e.g., reduce or eliminate it altogether or prevent it from becoming worse.

Thus the invention encompasses the use of the compounds described herein alone or in combination with other therapeutics for the treatment of a subject having or at risk of having a viral infection, e.g., an enveloped viral infection. A "subject having an enveloped viral infection" is a subject that has had contact with a virus. Thus the virus has invaded the body of the subject. The word "invade" as used herein refers to contact by the virus with an external surface of the subject, e.g., skin or mucosal membranes and/or refers to the penetration of the external surface of the subject by the virus. A subject at risk of having an enveloped virus infection is one that has been exposed to or may become exposed to an enveloped virus or a geographical area in which an enveloped viral infection has been reported. Further risks include close contact with a human or non-human primate or their tissues infected with the virus. Such persons include laboratory or quarantine facility workers who handle non-human primates that have been associated with the disease. In addition, hospital staff and family members who care for patients with the disease are at risk if they do not use proper barrier nursing techniques.

As used herein, a subject includes humans and non-human animals such as non-human primates, dogs, cats, sheep, goats, cows, pigs, horses and rodents.

In certain embodiments, the methods of the invention are useful for treating infection with enveloped viruses. Viruses are small infectious agents which contain a nucleic acid core and a protein coat, but are not independently living organisms. A virus cannot multiply in the absence of a living cell within which it can replicate. Viruses enter specific living cells either by transfer across a membrane or direct injection and multiply, causing disease. The multiplied virus can then be released and infect additional cells. Some viruses are DNA-containing viruses and others are RNA-containing viruses. The genomic size, composition and organization of viruses show tremendous diversity.

As used herein, an "enveloped" virus is an animal virus which possesses a membrane or 'envelope', which is a lipid bilayer containing viral proteins. The envelope proteins of a virus play a pivotal role in its lifecycle. They participate in the assembly of the infectious particle and also play a crucial role in virus entry by binding to a receptor present on the host cell and inducing fusion between the viral envelope and a membrane of the host cell. Enveloped viruses can be either spherical or filamentous (rod-shaped) and include but are not limited to filoviruses, such as Ebola virus or Marburg virus, Lassa virus, Arboroviruses such as Togaviruses, flaviviruses (such as hepatitis-C virus), bunyaviruses, and Arenaviruses, Orthomyxoviridae, Paramyxoviridae, poxvirus, herpesvirus, hepadnavirus, Rhabdovirus, Bornavirus, and Arterivirus.

*Flaviviridae* is a member of the family of (+)-sense RNA enveloped viruses. *Flaviviridae* includes *Flavivirus, Pestivirus*, and *Hepacivirus*. The *Flavivirus* genus includes yellow fever virus, dengue fever virus, West Nile virus, and Japanese encaphilitis (JE) virus. Major diseases caused by viruses in the Flaviviridae family include: Dengue fever, Japanese encephalitis, Kyasanur Forest disease, Murray Valley encephalitis, St. Louis encephalitis, Tick-borne encephalitis, West Nile encephalitis, Yellow fever, and Hepatitis C. The *Pestivirus* genus includes the three serotypes of bovine viral diarrhea, but no known human pathogens. Genus *Hepacivirus* consists of hepatitis C virus and hepatitis C-like viruses.

A yellow fever virus infection is characterized by an incubation period of 3 to 6 days, during which 5% to 50% of infected people develop disease. Yellow fever begins with a nonspecific 1-to 3day febrile illness, followed by a brief remission, and then by a life-threatening toxic syndrome accompanied by epistaxis, other hemorrhagic phenomena, jaundice, and disseminated intravascular coagulation. Mortality rates for yellow fever are approximately 20%.

There are four serotypes of dengue fever virus, all transmitted by mosquitos. Dengue fever virus infection may be asymptomatic or may result in dengue fever. This is generally a self-limiting febrile illness which occurs after a 4-8 day incubation period. It has symptoms such as fever, aches and arthralgia (pain in the joints) which can progress to arthritis (inflammation of the joints), myositis (inflammation of muscle tissue) and a discrete macular or maculopapular rash. In this situation clinical differentiation from other viral illnesses may not be possible, recovery is rapid, and need for supportive treatment is minimal. Dengue haemorrhagic fever (DHF) is a potentially deadly complication. Dengue hemorrhagic fever commences with high fever and many of the symptoms of dengue fever, but with extreme lethargy and drowsiness. The patient has increased vascular permeability and abnormal homeostasis that can lead to hypovolemia and hypotension, and in severe cases, result in hypovolemic shock often complicated by severe internal bleeding.

The Japanese encephalitis antigenic complex includes Alfuy, Japanese encephalitis, Kokobera, Koutango, Kunjin, Murray Valley encephalitis, St. Louis encephalitis, Stratford, Usutu, and West Nile viruses. These viruses are transmissible by mosquitoes and many of them can cause febrile, sometimes fatal, illnesses in humans. West Nile virus is the most widespread of the flaviviruses, with geographic distribution including Africa and Eurasia. West Nile virus RNA has been detected in overwintering mosquitoes in New York City & the geographic range of the virus is increasing in the USA.

The genus *Pestivirus* has been divided into bovine viral diarrhea virus (BVDV), classical swine fever virus (CSFV), and border disease virus (BDV). Infection with BVDV results in a variety of diseases ranging from subclinical to highly fatal. Many BVDV viruses cause only clinically mild disease in nonpregnant adult cattle. Prenatal infection can cause congenital malformations and/or fetal death.

The *Hepacivirus* genus includes the hepatitis C virus (HCV). The majority of cases of HCV infection give rise to an acute illness, where up to 85% of infections may develop into chronic hepatitis. Almost all patients develop a vigorous antibody and cell-mediated immune response which fails to clear the infection but may contribute towards liver damage.

In some embodiments, the desired dose of the active agent will depend on absorption, inactivation, and excretion rates of the drug as well as the delivery rate of the compound. It is to be noted that dosage values may also vary with the severity of the condition to be alleviated. It is to be further understood that for any particular subject, specific dosage regimens should be adjusted over time according to the individual need and the professional judgment of the person administering or supervising the administration of the compositions. Typically, dosing will be determined using techniques known to one skilled in the art.

The dosage of the active agent may be determined by reference to the plasma concentrations of the agent. For example, the maximum plasma concentration (Cmax) and the area under the plasma concentration-time curve from time 0 to infinity (AUC (0-4)) may be used. Dosages for the invention include those that produce the above values for Cmax and AUC (0-4) and other dosages resulting in larger or smaller values for those parameters.

Actual dosage levels of the active agents may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular agent employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could prescribe and/or administer doses of the agents of the invention employed in the pharmaceutical composition at levels lower than that required in order to achieve the desired therapeutic effect and gradually increase the dosage until the desired effect is achieved.

In general, a suitable daily dose of an agent of the invention will be that amount of the agent (e.g., the compound) which is the lowest dose effective to produce a therapeutic effect. Such an effective dose will generally depend upon the factors described above.

If desired, the effective daily dose of the agent may be administered as two, three, four, five, six or more sub-doses administered separately at appropriate intervals throughout the day, optionally, in unit dosage forms.

The precise time of administration and amount of any particular agent that will yield the most effective treatment in a given patient will depend upon the activity, pharmacokinetics, and bioavailability of a particular agent, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

While the subject is being treated, the health of the subject may be monitored by measuring one or more of the relevant indices at predetermined times during a 24-hour period. All aspects of the treatment, including supplements, amounts, times of administration and formulation, may be optimized according to the results of such monitoring. The patient may be periodically reevaluated to determine the extent of improvement by measuring the same parameters, the first such reevaluation typically occurring at the end of four weeks from the onset of therapy, and subsequent reevaluations occurring every four to eight weeks during therapy and then every three months thereafter. Therapy may continue for several months or even years, with a minimum of one month being a typical length of therapy for humans. Adjustments, for example, to the amount(s) of agent administered and to the time of administration may be made based on these reevaluations.

Treatment may be initiated with smaller dosages which are less than the optimum dose of the compound. Thereafter, the dosage may be increased by small increments until the optimum therapeutic effect is attained. In addition, the combined use an agent that modulates an autotrophy-associated gene product and a second agent, e.g. another agent useful for the treatment of the autophagy-related disease, may reduce the required dosage for any individual agent because the onset and duration of effect of the different compounds and/or agents may be complimentary.

In certain embodiments, the invention relates to any of the aforementioned methods, wherein A is aryl or heteroaryl.

In certain embodiments, the invention relates to any of the aforementioned methods, wherein A is phenyl, pyridin-2-yl, pyridin-3-yl or pyrimidin-2-yl, optionally substituted with 1, 2, 3, 4 or 5 substituents independently selected from the group consisting of alkyl, alkenyl, alkynyl, halo, haloalkyl, fluoroalkyl, hydroxy, alkoxy, alkyenyloxy, alkynyloxy, carbocyclyloxy, heterocyclyloxy, haloalkoxy, fluoroalkyloxy, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, sulfoxymethyl, sulfonamido, amino, amido, azido, aminosulfonyl, aminosulfinyl, cyano, nitro, phosphinyl, phosphoryl, silyl, silyloxy, and any of said substiuents bound to the phenyl, pyridin-2yl, pyridin-3-yl or pyrimidin-2-yl through a methylene or ethylene moiety.

In certain embodiments, the invention relates to any of the aforementioned methods, wherein A is phenyl, optionally substituted with 1, 2, 3, 4 or 5 substituents independently selected from the group consisting of alkyl, halo, haloalkyl, fluoroalkyl, hydroxy, alkoxy, haloalkoxy, fluoroalkyloxy, amino, azido, cyano, and nitro.

In certain embodiments, the invention relates to any of the aforementioned methods, wherein A is

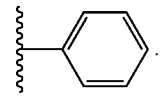

In certain embodiments, the invention relates to any of the aforementioned methods, wherein A is phenyl substituted in the two position (ortho substituted) with a substituent selected from the group consisting of alkyl, halo, haloalkyl, fluoroalkyl, hydroxy, alkoxy, haloalkoxy, fluoroalkyloxy, amino, azido, cyano, and nitro.

In certain embodiments, the invention relates to any of the aforementioned methods, wherein A is

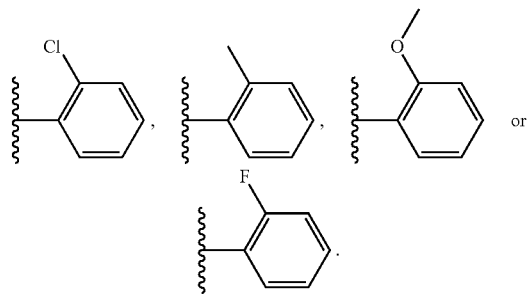

In certain embodiments, the invention relates to any of the aforementioned methods, wherein A is phenyl substituted in the three position (meta substituted) with a substitutent selected from the group consisting of alkyl, halo, haloalkyl, fluoroalkyl, hydroxy, alkoxy, haloalkoxy, fluoroalkyloxy, amino, azido cyano, and nitro.

In certain embodiments, the invention relates to any of the aforementioned methods, wherein A is

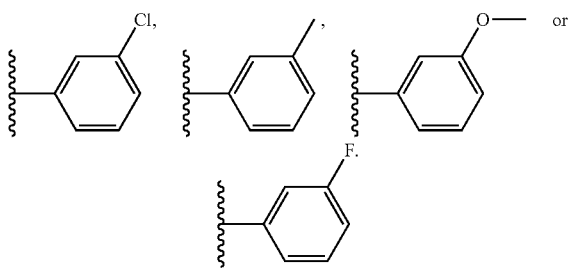

In certain embodiments, the invention relates to any of the aforementioned methods, wherein A is phenyl substituted in the four position (para substituted) with a substitutent selected from the group consisting of alkyl, halo, haloalkyl, fluoroalkyl, hydroxy, alkoxy, haloalkoxy, fluoroalkyloxy, amino, azido, cyano, and nitro.

In certain embodiments, the invention relates to any of the aforementioned methods, wherein A is

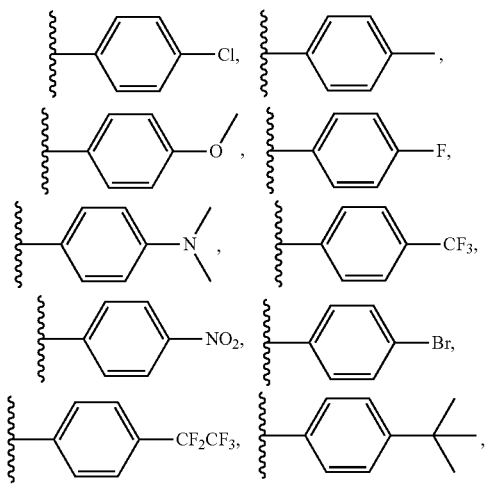

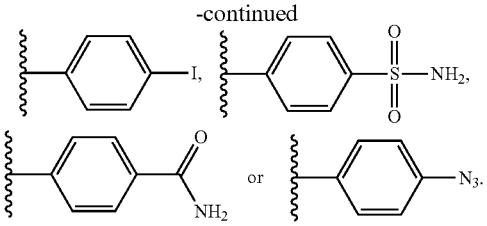

In certain embodiments, the invention relates to any of the aforementioned methods, wherein A is phenyl substituted in the two and four positions with substitutents independently selected from the group consisting of alkyl, halo, haloalkyl, fluoroalkyl, hydroxy, alkoxy, haloalkoxy, fluoroalkyloxy, amino, azido, cyano, and nitro.

In certain embodiments, the invention relates to any of the aforementioned methods, wherein A is

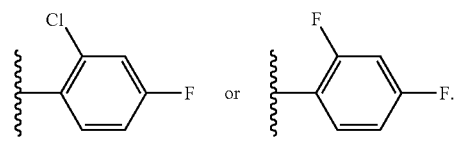 [SMILES: *c1ccc(F)cc1Cl ; *c1ccc(F)cc1F]

In certain embodiments, the invention relates to any of the aforementioned methods, wherein A is pyridin-2-yl, optionally substituted in the four position with a substituent selected from the group consisting of alkyl, halo, haloalkyl, fluoroalkyl, hydroxy, alkoxy, haloalkoxy, fluoroalkyloxy, amino, azido, cyano, and nitro.

In certain embodiments, the invention relates to any of the aforementioned methods, wherein A is

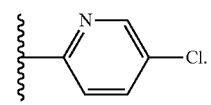

In certain embodiments, the invention relates to any of the aforementioned methods, wherein A is pyrimidin-2-yl, optionally substituted in the four position with a substituent selected from the group consisting of alkyl, halo, haloalkyl, fluoroalkyl, hydroxy, alkoxy, haloalkoxy, fluoroalkyloxy, amino, azido, cyano, and nitro.

In certain embodiments, the invention relates to any of the aforementioned methods, wherein A is

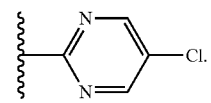

In certain embodiments, the invention relates to any of the aforementioned methods, wherein A is biaryl.

In certain embodiments, the invention relates to any of the aforementioned methods, wherein A is 4-(phenyl)phen-1-yl or 4-(2-pyridinyl)phen-1-yl, optionally substituted with 1, 2, 3, 4 or 5 substituents independently selected from the group consisting of alkyl, halo, haloalkyl, fluoroalkyl, hydroxy, alkoxy, haloalkoxy, fluoroalkyloxy, amino, azido, cyano, and nitro.

In certain embodiments, the invention relates to any of the aforementioned methods, wherein A is

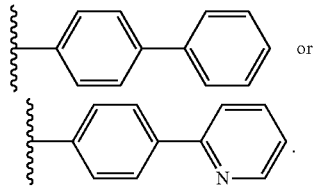 or

.

In certain embodiments, the invention relates to any of the aforementioned methods, wherein $R^1$ is hydrogen.

In certain embodiments, the invention relates to any of the aforementioned methods, wherein $R^1$ is alkyl.

In certain embodiments, the invention relates to any of the aforementioned methods, wherein $R^1$ is haloalkyl.

In certain embodiments, the invention relates to any of the aforementioned methods, wherein $R^1$ is fluoroalkyl.

In certain embodiments, the invention relates to any of the aforementioned methods, wherein $R^1$ is methyl.

In certain embodiments, the invention relates to any of the aforementioned methods, wherein $R^1$ is halomethyl.

In certain embodiments, the invention relates to any of the aforementioned methods, wherein $R^1$ is fluoromethyl.

In certain embodiments, the invention relates to any of the aforementioned methods, wherein $R^1$ is ethyl.

In certain embodiments, the invention relates to any of the aforementioned methods, wherein $R^1$ is haloethyl.

In certain embodiments, the invention relates to any of the aforementioned methods, wherein $R^1$ is fluoroethyl.

In certain embodiments, the invention relates to any of the aforementioned methods, wherein $R^2$ is hydrogen.

In certain embodiments, the invention relates to any of the aforementioned methods, wherein $R^2$ is alkyl.

In certain embodiments, the invention relates to any of the aforementioned methods, wherein $R^2$ is methyl.

In certain embodiments, the invention relates to any of the aforementioned methods, wherein $R^2$ is ethyl.

In certain embodiments, the invention relates to any of the aforementioned methods, wherein $R^1$ is hydrogen; and $R^2$ is hydrogen.

In certain embodiments, the invention relates to any of the aforementioned methods, wherein $R^1$ is alkyl; and $R^2$ is alkyl.

In certain embodiments, the invention relates to any of the aforementioned methods, wherein $R^1$ is methyl; and $R^2$ is methyl.

In certain embodiments, the invention relates to any of the aforementioned methods, wherein $R^1$ is ethyl; and $R^2$ is ethyl.

In certain embodiments, the invention relates to any of the aforementioned methods, wherein Z is $=C(R^8)-$; and $R^8$ is hydrogen.

In certain embodiments, the invention relates to any of the aforementioned methods, wherein Z is $=C(R^8)-$; and $R^8$ is alkyl.

In certain embodiments, the invention relates to any of the aforementioned methods, wherein Z is $=N-$.

In certain embodiments, the invention relates to any of the aforementioned methods, wherein X is

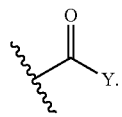

In certain embodiments, the invention relates to any of the aforementioned methods, wherein X is

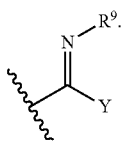

In certain embodiments, the invention relates to any of the aforementioned methods, wherein X is

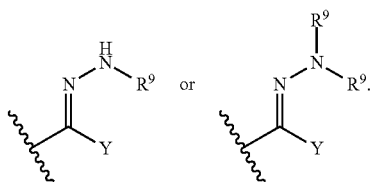

In certain embodiments, the invention relates to any of the aforementioned methods, wherein X is heteroaryl.

In certain embodiments, the invention relates to any of the aforementioned methods, wherein X is pyrrolo[1,2-a]pyrazin-3-yl.

In certain embodiments, the invention relates to any of the aforementioned methods, wherein $R^9$ is alkyl. In certain embodiments, the invention relates to any of the aforementioned compounds, wherein $R^9$ is methyl.

In certain embodiments, the invention relates to any of the aforementioned methods, wherein Y is $-CH_2NR^3R^4$.

In certain embodiments, the invention relates to any of the aforementioned methods, wherein Y is $-CH_2NR^3R^4$; and $R^3$ is hydrogen.

In certain embodiments, the invention relates to any of the aforementioned methods, wherein Y is $-CH_2NR^3R^4$; and $R^3$ is alkyl. In certain embodiments, the invention relates to any of the aforementioned compounds, wherein Y is $-CH_2NR^3R^4$; and $R^4$ is hydrogen.

In certain embodiments, the invention relates to any of the aforementioned methods, wherein Y is $-CH_2NR^3R^4$; and $R^4$ is alkyl.

In certain embodiments, the invention relates to any of the aforementioned methods, wherein Y is $-CH_2NR^3R^4$; and $R^4$ is alkoxyalkyl.

In certain embodiments, the invention relates to any of the aforementioned methods, wherein Y is $-CH_2NR^3R^4$; $R^3$ is hydrogen; and $R^4$ is alkyl.

In certain embodiments, the invention relates to any of the aforementioned methods, wherein Y is $-CH_2NR^3R^4$; $R^3$ is alkyl; and $R^4$ is alkyl.

In certain embodiments, the invention relates to any of the aforementioned methods, wherein Y is $-CH_2NR^3R^4$; $R^3$ is hydrogen; and $R^4$ is alkoxyalkyl.

In certain embodiments, the invention relates to any of the aforementioned methods, wherein Y is $-CH_2NR^3R^4$; $R^3$ is alkyl; and $R^4$ is alkoxyalkyl.

In certain embodiments, the invention relates to any of the aforementioned methods, wherein Y is

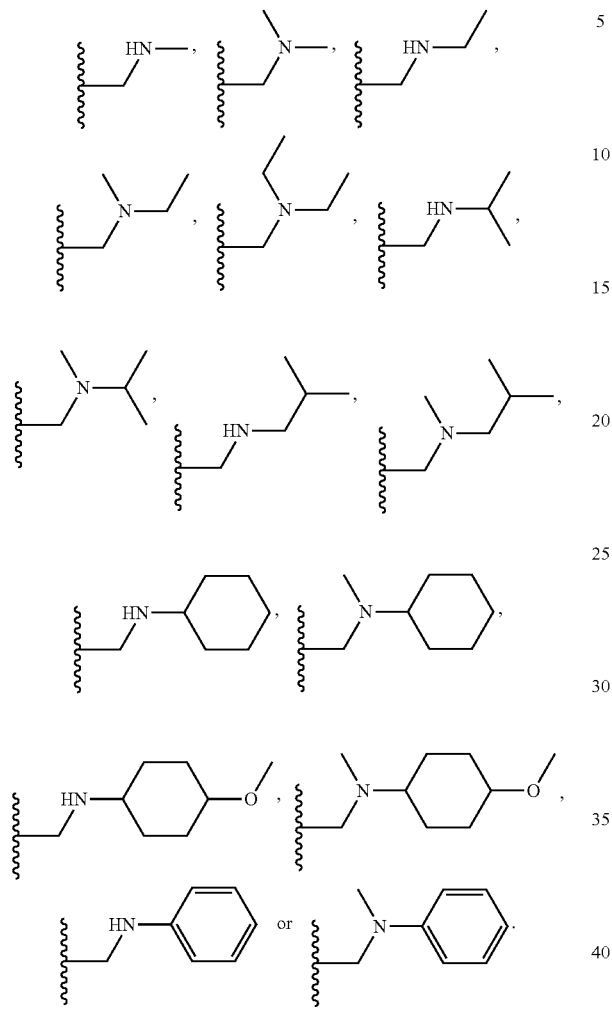

In certain embodiments, the invention relates to any of the aforementioned methods, wherein Y is —CH$_2$(N-heterocyclyl), which is optionally substituted with one, two, three, four or five substituents independently selected from the group consisting of alkyl, haloalkyl, fluoroalkyl, halo, hydroxyl, alkoxy, haloalkoxy, fluoroalkoxy, amino and nitro.

In certain embodiments, the invention relates to any of the aforementioned methods, wherein Y is —CH$_2$ (piperidin-1-yl), —CH$_2$ (piperazin-1-yl), —CH$_2$ (hexahydropyrimidin-1-yl), —CH$_2$(morpholi-1-yl) or —CH$_2$(1,3-oxazinan-3-yl), which is optionally substituted with one, two, three, four or five substituents independently selected from the group consisting of alkyl, haloalkyl, fluoroalkyl, halo, hydroxyl, alkoxy, haloalkoxy, fluoroalkoxy, amino and nitro.

In certain embodiments, the invention relates to any of the aforementioned methods, wherein Y is —CH$_2$(piperidin-1-yl) or —CH$_2$(piperazin-1-yl), which is optionally substituted with one, two, three, four or five substituents independently selected from the group consisting of alkyl, haloalkyl, fluoroalkyl, halo, hydroxyl, alkoxy, haloalkoxy, fluoroalkoxy, amino and nitro.

In certain embodiments, the invention relates to any of the aforementioned methods, wherein Y is

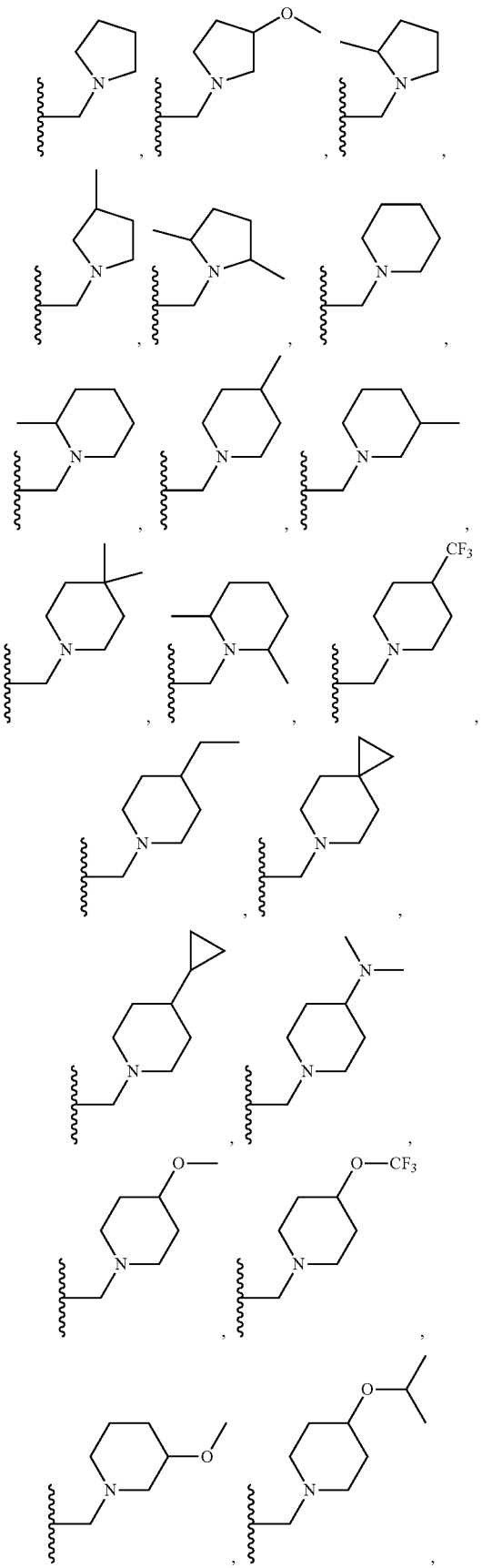

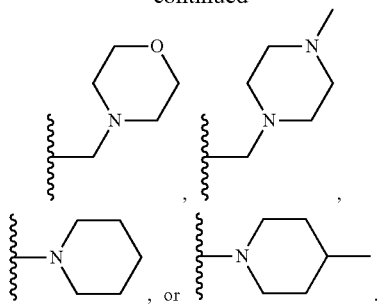
, or .

In certain embodiments, the invention relates to any of the aforementioned methods, wherein Y is —CH$_2$NH(CH$_2$)$_n$NH(alkyl), —CH$_2$NH(CH$_2$)$_n$N(alkyl)$_2$, —CH$_2$NH(CH$_2$)$_n$N(alkylene), —CH$_2$N(alkyl)(CH$_2$)$_n$NH(alkyl), —CH$_2$N(alkyl)(CH$_2$)$_n$N(alkyl)$_2$ or —CH$_2$N(alkyl)(CH$_2$)$_n$N(alkylene).

In certain embodiments, the invention relates to any of the aforementioned methods, wherein Y is —CH$_2$NH(CH$_2$)$_n$O(alkyl) or —CH$_2$N(alkyl)(CH$_2$)$_n$O(alkyl).

In certain embodiments, the invention relates to any of the aforementioned methods, wherein n is 1.

In certain embodiments, the invention relates to any of the aforementioned methods, wherein n is 2.

In certain embodiments, the invention relates to any of the aforementioned methods, wherein n is 3.

In certain embodiments, the invention relates to any of the aforementioned methods, wherein n is 4.

In certain embodiments, the invention relates to any of the aforementioned methods, wherein Y is

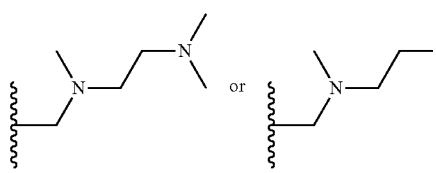
or .

In certain embodiments, the invention relates to any of the aforementioned methods, wherein Y is —NR$^3$R$^4$.

In certain embodiments, the invention relates to any of the aforementioned methods, wherein Y is —NR$^3$R$^4$; and R$^3$ is hydrogen.

In certain embodiments, the invention relates to any of the aforementioned methods, wherein Y is —NR$^3$R$^4$; and R$^3$ is alkyl.

In certain embodiments, the invention relates to any of the aforementioned methods, wherein Y is —NR$^3$R$^4$; and R$^4$ is hydrogen.

In certain embodiments, the invention relates to any of the aforementioned methods, wherein Y is —NR$^3$R$^4$; and R$^4$ is alkyl.

In certain embodiments, the invention relates to any of the aforementioned methods, wherein Y is —NR$^3$R$^4$; R$^3$ is hydrogen; and R$^4$ is alkyl.

In certain embodiments, the invention relates to any of the aforementioned methods, wherein Y is —NR$^3$R$^4$; R$^3$ is hydrogen; and R$^4$ is hydrogen. In certain embodiments, the invention relates to any of the aforementioned compounds, wherein Y is —NR$^3$R$^4$; R$^3$ is alkyl; and R$^4$ is alkyl.

In certain embodiments, the invention relates to any of the aforementioned methods, wherein Y is —NR$^5$NR$^6$R$^7$ or —NR$^5$(N-heterocyclyl).

In certain embodiments, the invention relates to any of the aforementioned methods, wherein Y is —NR$^5$NR$^6$R$^7$; and R$^5$ is hydrogen.

In certain embodiments, the invention relates to any of the aforementioned methods, wherein Y is —NR$^5$NR$^6$R$^7$; and R$^5$ is alkyl.

In certain embodiments, the invention relates to any of the aforementioned methods, wherein Y is —NR$^5$NR$^6$R$^7$; and R$^5$, R$^6$ and R$^7$ are, independently, hydrogen or alkyl.

In certain embodiments, the invention relates to any of the aforementioned methods, wherein Y is —NR$^5$(N-heterocyclyl); and R$^5$ is hydrogen.

In certain embodiments, the invention relates to any of the aforementioned methods, wherein Y is —NR$^5$(N-heterocyclyl); and R$^5$ is alkyl.

In certain embodiments, the invention relates to any of the aforementioned methods, wherein Y is

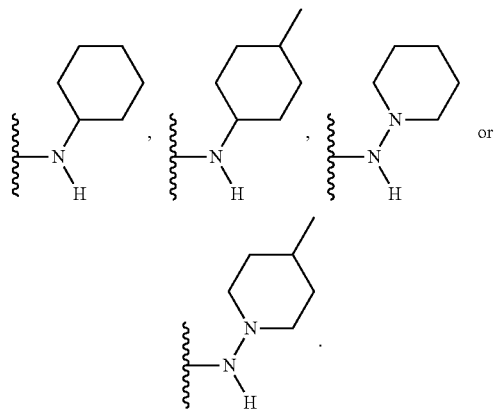

In certain embodiments, the invention relates to any of the aforementioned methods, wherein Z is =C(R$^2$)—; and the two R$^2$ taken together are

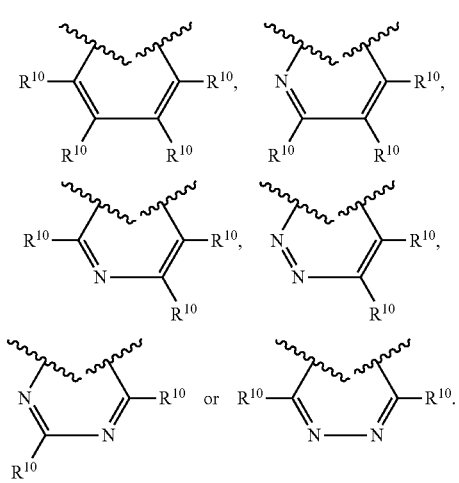

In certain embodiments, the invention relates to any of the aforementioned methods, wherein Z is =C(R$^2$)—; and the two R$^2$ taken together are

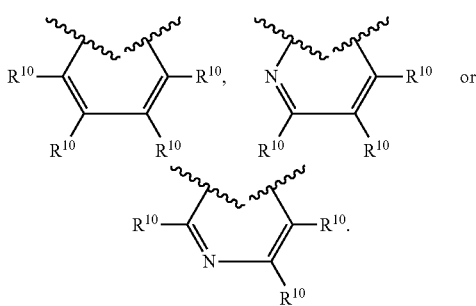

In certain embodiments, the invention relates to any of the aforementioned methods, wherein Z is =C(R$^2$)—; and the two R$^2$ taken together are

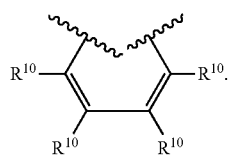

In certain embodiments, the invention relates to any of the aforementioned methods, wherein Z is =C(R$^2$)—; and the two R$^2$ taken together are

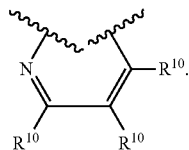

In certain embodiments, the invention relates to any of the aforementioned methods, wherein Z is =C(R$^2$)—; and the two R$^2$ taken together are

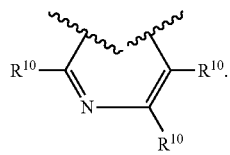

In certain embodiments, the invention relates to any of the aforementioned methods, wherein R$^{10}$ is hydrogen, alkyl, haloalkyl, fluoroalkyl, alkyoxy, alkoxyalkyl, halo or trifluoromethyl.

In certain embodiments, the invention relates to any of the aforementioned methods, wherein R$^{10}$ is hydrogen, amino, amido, N-heterocyclyl, aminoalkyl, amidoalkyl, or N-heterocyclylalkyl.

In certain embodiments, the invention relates to any of the aforementioned methods, wherein R$^{10}$ is hydrogen, halo or N-heterocyclyl.

In certain embodiments, the invention relates to any of the aforementioned methods, wherein R$^{10}$ is hydrogen, chloro or piperidin-1-yl.

In certain embodiments, the invention relates to any of the aforementioned methods, wherein R$^{10}$ is hydrogen or N-heterocyclylalkyl.

In certain embodiments, the invention relates to any of the aforementioned methods, wherein R$^{10}$ is hydrogen or piperidin-1-ylmethyl.

In certain embodiments, the invention relates to any of the aforementioned methods, wherein R$^{10}$ is hydrogen or alkyl.

In certain embodiments, the invention relates to any of the aforementioned methods, wherein R$^{10}$ is hydrogen.

In certain embodiments, the invention relates to any of the aforementioned methods, wherein R$^{11}$ is hydrogen or alkyl.

In certain embodiments, the invention relates to any of the aforementioned methods, wherein R$^{11}$ is hydrogen.

In certain embodiments, the invention relates to any of the aforementioned methods, wherein R$^{11}$ is methyl.

In certain embodiments, the invention relates to any of the aforementioned methods, wherein R$^{12}$ is hydrogen.

In certain embodiments, the invention relates to any of the aforementioned methods, wherein R$^{12}$ is methyl. In certain embodiments, the invention relates to any of the aforementioned methods, wherein R$^{13}$ is hydrogen.

In certain embodiments, the invention relates to any of the aforementioned methods, wherein exactly one R$^{13}$, and the carbon to which it is bound, is —N=.

In certain embodiments, the invention relates to any of the aforementioned methods, wherein R$^{14}$ is hydrogen.

In certain embodiments, the invention relates to any of the aforementioned methods, wherein R$^{14}$ is X. In certain embodiments, the invention relates to any of the aforementioned methods, wherein Z is =C(R$^2$)—; the two R$^2$ taken together are

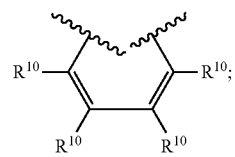

and R$^{10}$ is hydrogen, halo or N-heterocyclyl.

In certain embodiments, the invention relates to any of the aforementioned methods, wherein Z is =C(R$^2$)—; the two R$^2$ taken together are

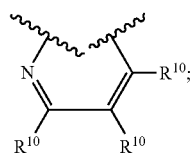

and R$^{10}$ is hydrogen or N-heterocyclylalkyl.

In certain embodiments, the invention relates to any of the aforementioned methods, wherein the compound is selected from the group consisting of

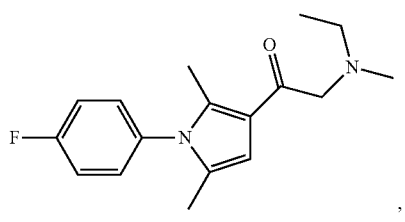

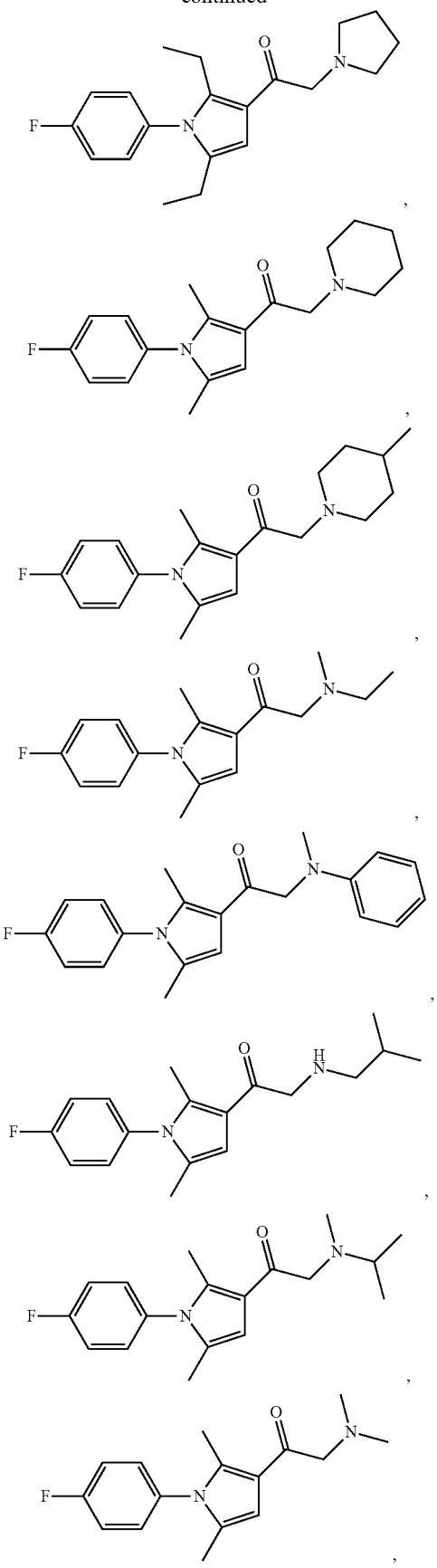
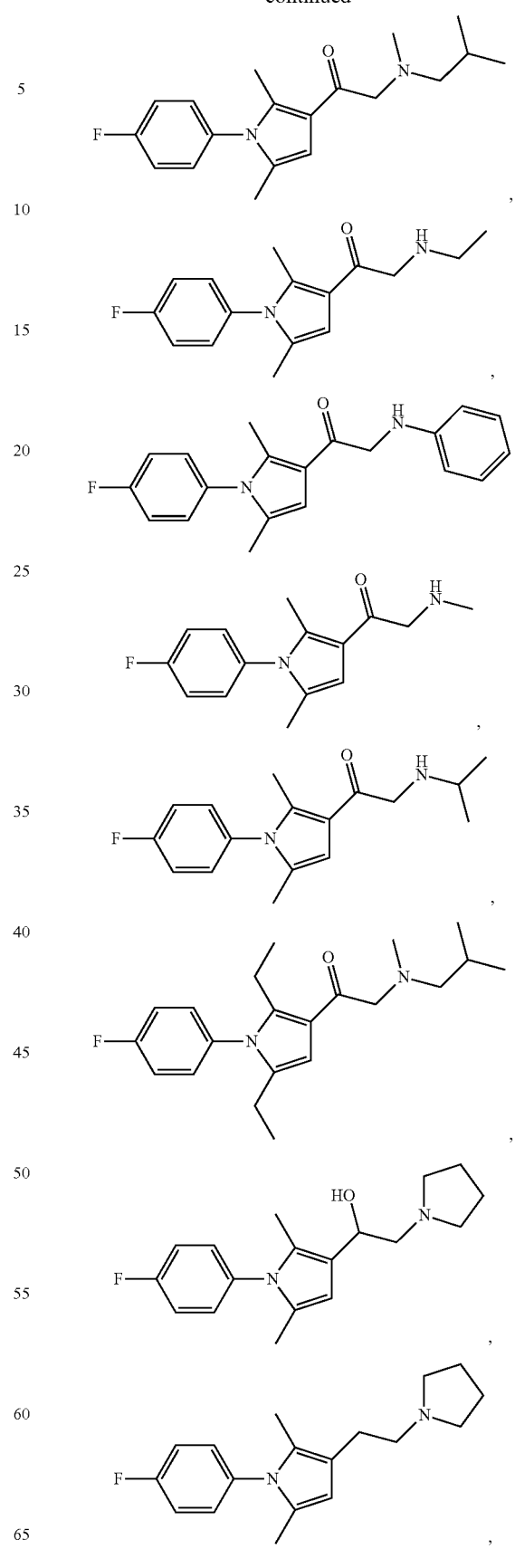

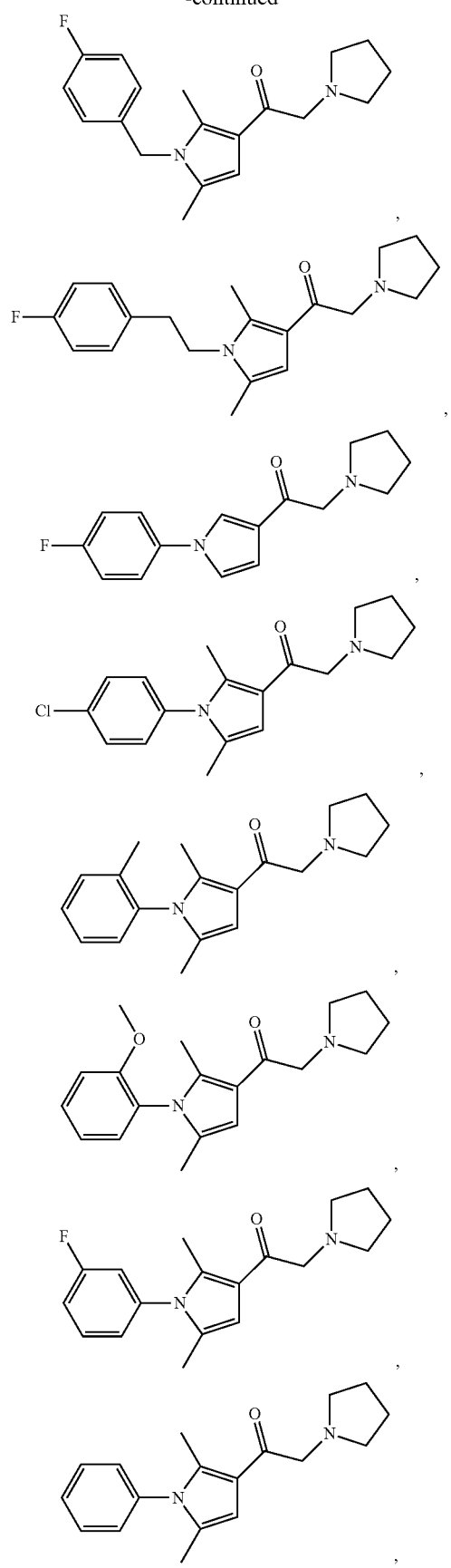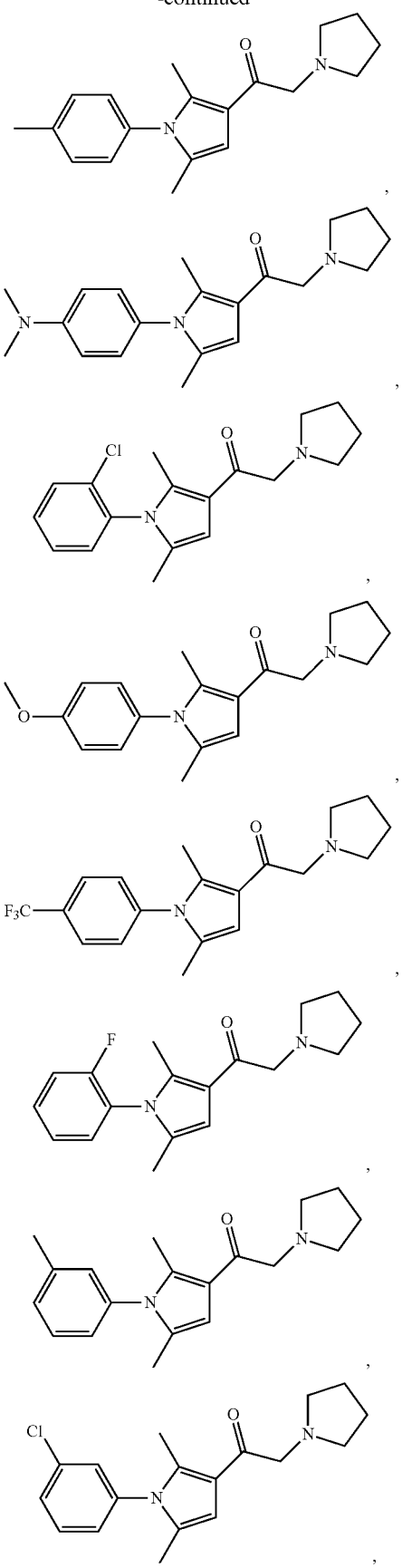

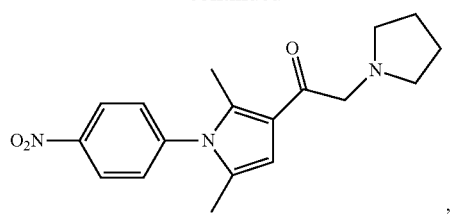

,

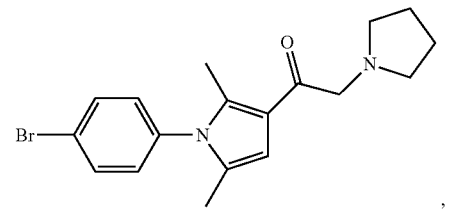

,

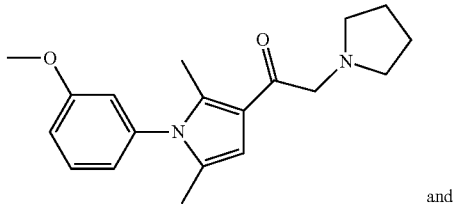

and

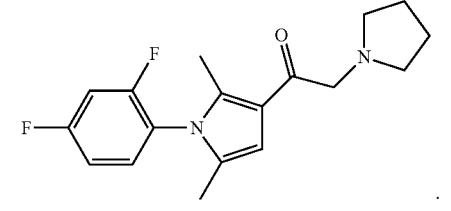

.

In certain embodiments, the invention relates to any of the aforementioned methods, wherein the compound is selected from the group consisting of

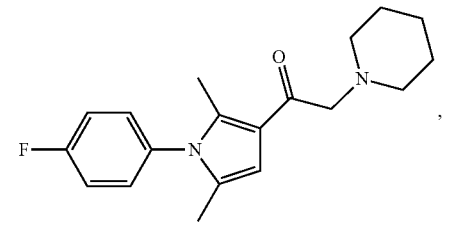

,

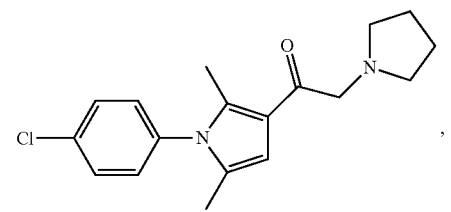

,

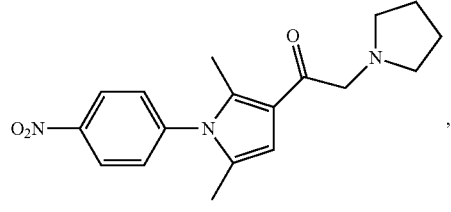

,

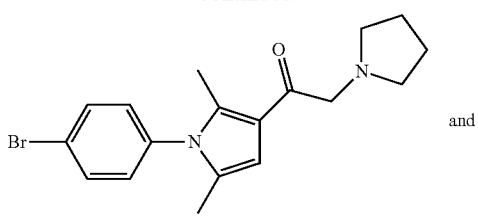

,

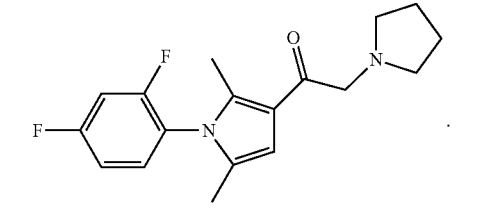

and

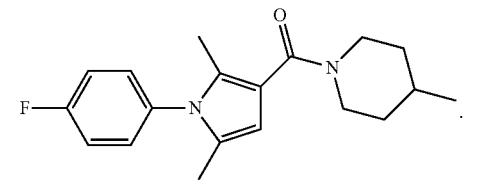 [SMILES: Cc1cc(C(=O)N2CCC(C)CC2)c(C)n1-c1ccc(F)cc1]

.

In certain embodiments, the invention relates to any of the aforementioned methods, wherein the compound is

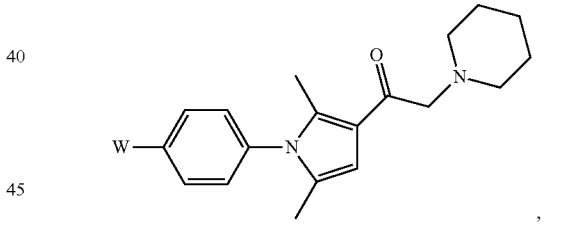

.

In certain embodiments, the invention relates to any of the aforementioned methods, wherein the compound is selected from the group consisting of

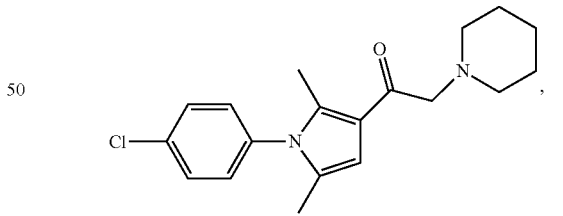

,

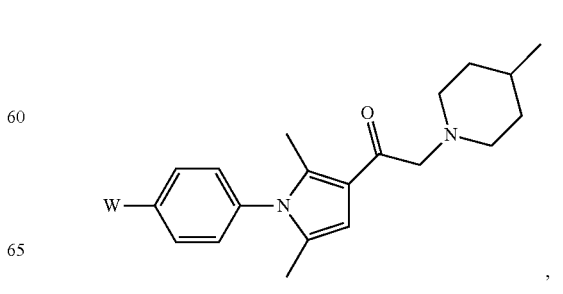

,

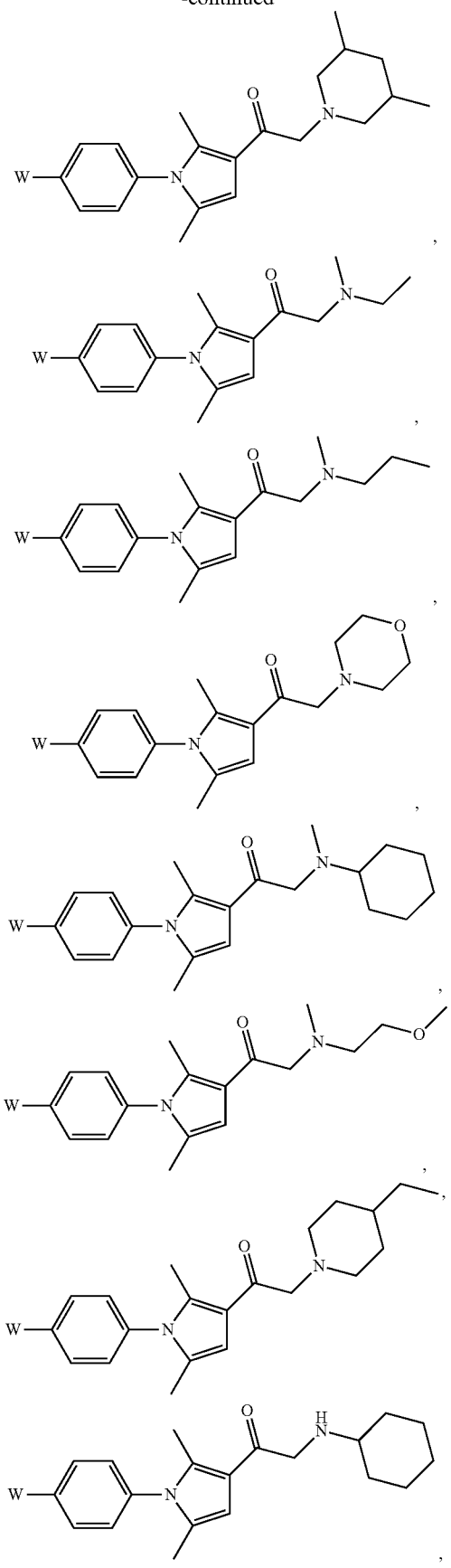
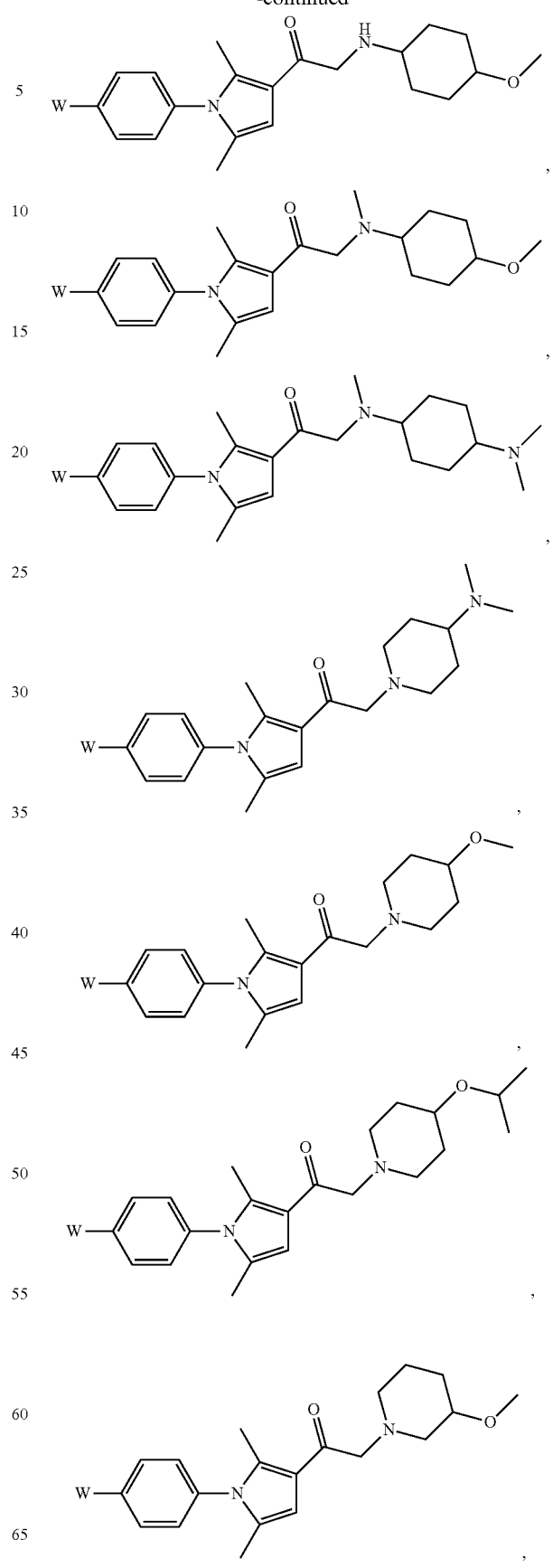

-continued

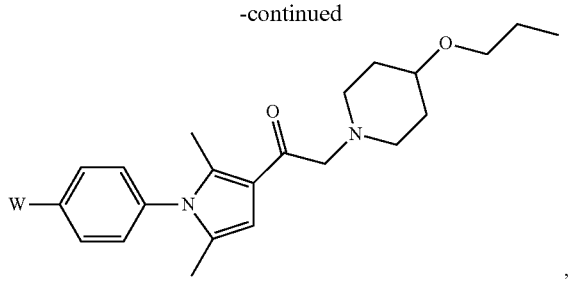

,

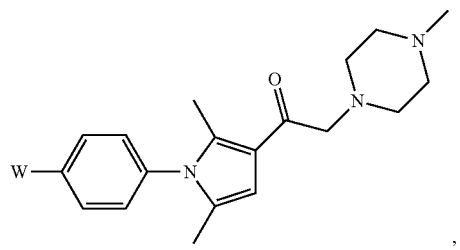

,

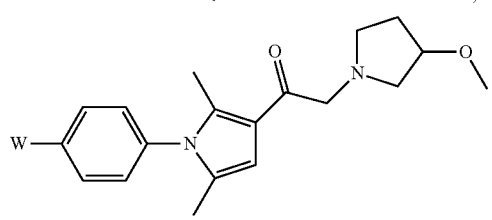

,

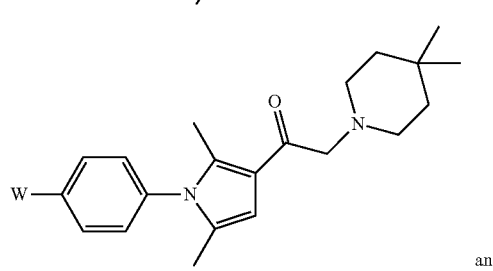

and

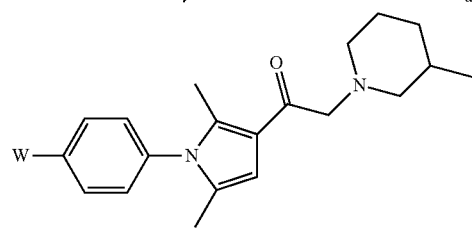

;

wherein W is methyl, fluoro, chloro, nitro, methoxy, ethoxy, —SO$_2$NH$_2$ or —C(=O)NH$_2$.

In certain embodiments, the invention relates to any of the aforementioned methods, wherein the compound is selected from the group consisting of

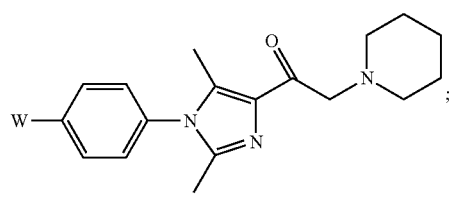

;

wherein W is alkyl, fluoro, chloro, nitro, methoxy, ethoxy, —SO$_2$NH$_2$ or —C(=O)NH$_2$.

In certain embodiments, the invention relates to any of the aforementioned methods, wherein W is methyl.

In certain embodiments, the invention relates to any of the aforementioned methods, wherein W is fluoro.

In certain embodiments, the invention relates to any of the aforementioned methods, wherein W is chloro.

In certain embodiments, the invention relates to any of the aforementioned methods, wherein W is nitro.

In certain embodiments, the invention relates to any of the aforementioned methods, wherein W is methoxy.

In certain embodiments, the invention relates to any of the aforementioned methods, wherein W is ethoxy.

In certain embodiments, the invention relates to any of the aforementioned methods, wherein W is —SO$_2$NH$_2$.

In certain embodiments, the invention relates to any of the aforementioned methods, wherein W is —C(=O)NH$_2$.

In certain embodiments, the invention relates to any of the aforementioned methods, wherein W is chloro.

In certain embodiments, the invention relates to any of the aforementioned methods, wherein the compound is selected from the group consisting of

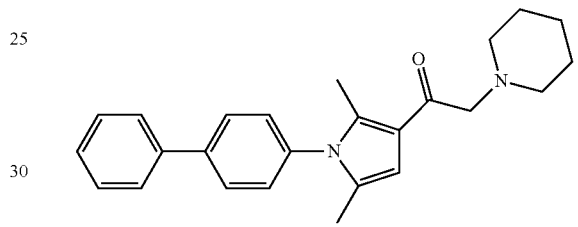

,

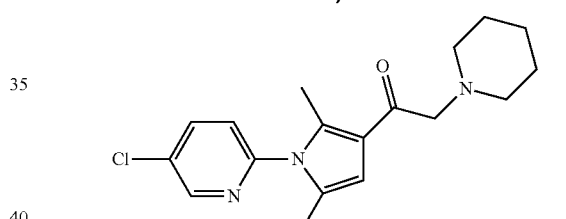

,

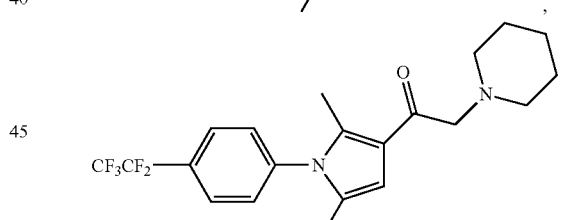

,

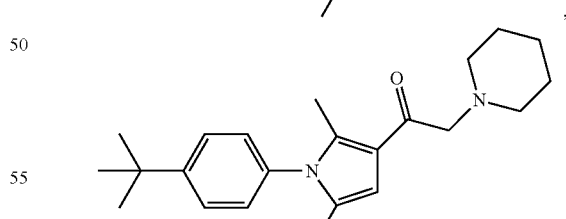

,

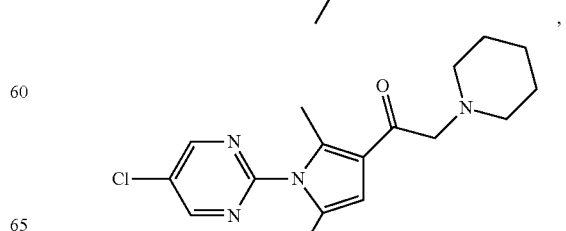

,

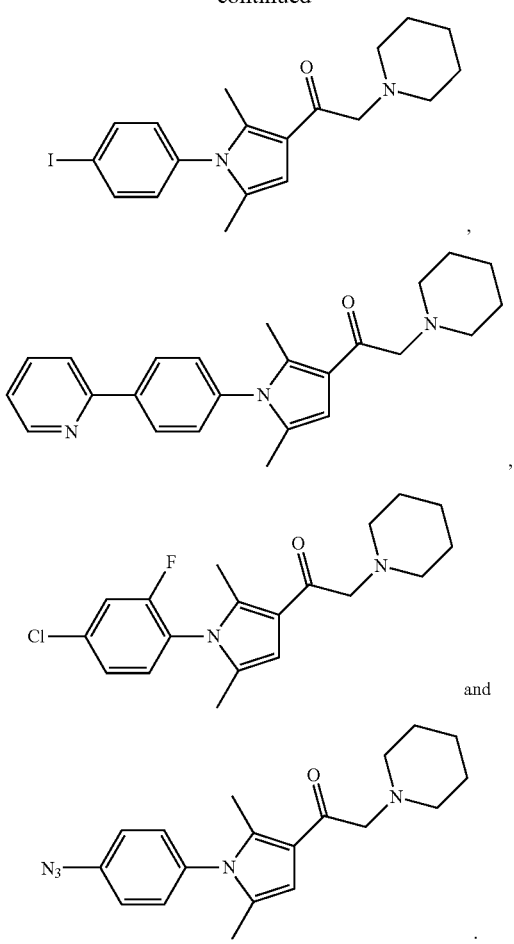

In certain embodiments, the invention relates to any of the aforementioned methods, wherein the compound is selected from the group consisting of

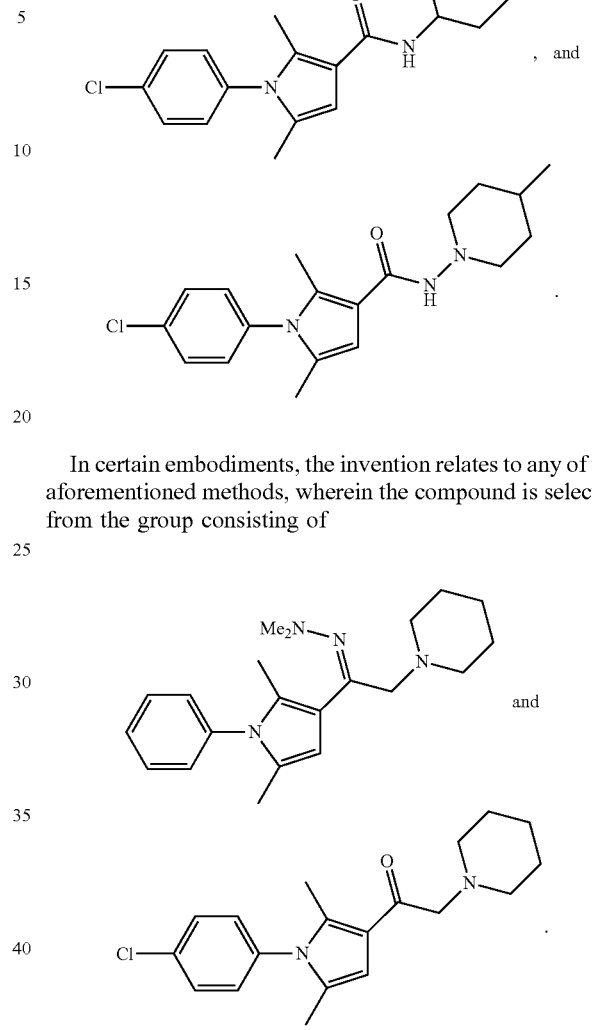

In certain embodiments, the invention relates to any of the aforementioned methods, wherein the compound is selected from the group consisting of

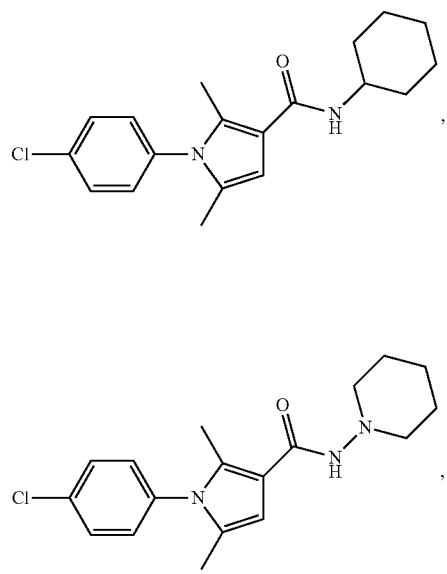

In certain embodiments, the invention relates to any of the aforementioned methods, wherein the compound is selected from the group consisting of

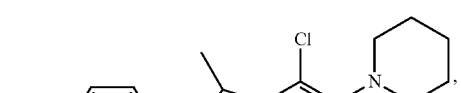

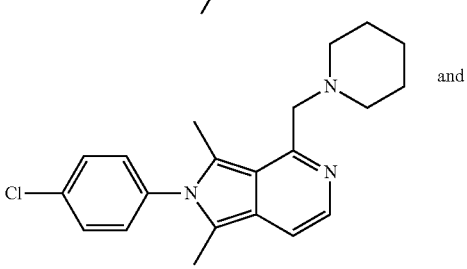

-continued

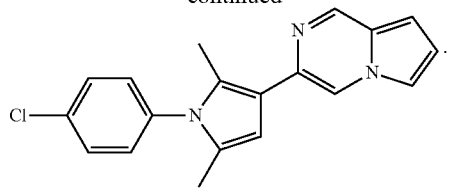

Many of the compounds used in the methods of the invention may be provided as salts with pharmaceutically compatible counterions (i.e., pharmaceutically acceptable salts). A "pharmaceutically acceptable salt" means any non-toxic salt that, upon administration to a recipient, is capable of providing, either directly or indirectly, a compound or a prodrug of a compound of this invention. A "pharmaceutically acceptable counterion" is an ionic portion of a salt that is not toxic when released from the salt upon administration to a recipient. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

Acids commonly employed to form pharmaceutically acceptable salts include inorganic acids such as hydrogen bisulfide, hydrochloric, hydrobromic, hydroiodic, sulfuric and phosphoric acid, as well as organic acids such as para-toluenesulfonic, salicylic, tartaric, bitartaric, ascorbic, maleic, besylic, fumaric, gluconic, glucuronic, formic, glutamic, methanesulfonic, ethanesulfonic, benzenesulfonic, lactic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, .beta.-hydroxybutyrate, glycolate, maleate, tartrate, methanesulfonate, propanesulfonate, naphthalene-1-sulfonate, naphthalene-2-sulfonate, mandelate and the like salts. Pharmaceutically acceptable acid addition salts include those formed with mineral acids such as hydrochloric acid and hydrobromic acid, and those formed with organic acids such as maleic acid.

Suitable bases for forming pharmaceutically acceptable salts with acidic functional groups include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl, N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N-dilower alkyl-N-(hydroxyl lower alkyl)-amines, such as N,N-dimethyl-N-(2-hydroxyethyl)amine, or tri-(2-hydroxyethyl) amine; N-methyl-D-glucamine; and amino acids such as arginine, lysine, and the like.

Certain compounds used in methods of the invention and their salts may exist in more than one crystal form and the invention includes each crystal form and mixtures thereof.

Certain compounds used in methods of the invention and their salts may also exist in the form of solvates, for example hydrates, and the invention includes each solvate and mixtures thereof.

Certain compounds used in methods of the invention may contain one or more chiral centers, and exist in different optically active forms. When compounds of the invention contain one chiral center, the compounds exist in two enantiomeric forms and the invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step may be used to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound used in the methods of the invention contains more than one chiral center, it may exist in diastereoisomeric forms. The diastereoisomeric compounds may be separated by methods known to those skilled in the art, for example chromatography or crystallization and the individual enantiomers may be separated as described above. The invention includes each diastereoisomer of compounds of the invention and mixtures thereof.

Certain compounds used in methods of the invention may exist in different tautomeric forms or as different geometric isomers, and the invention includes each tautomer and/or geometric isomer of compounds of the invention and mixtures thereof.

Certain compounds used in methods of the invention may exist in different stable conformational forms which may be separable. Torsional asymmetry due to restricted rotation about an asymmetric single bond, for example because of steric hindrance or ring strain, may permit separation of different conformers. The invention includes each conformational isomer of compounds of the invention and mixtures thereof.

Certain compounds used in methods of the invention may exist in zwitterionic form and the invention includes each zwitterionic form of compounds of the invention and mixtures thereof.

The invention also includes methods of using pro-drugs. As used herein the term "pro-drug" refers to an agent which is converted into the parent drug in vivo by some physiological chemical process (e.g., a prodrug on being brought to the physiological pH is converted to the desired drug form). Pro-drugs are often useful because, in some situations, they may be easier to administer than the parent drug. They may, for instance, be bioavailable by oral administration whereas the parent drug is not. The prodrug may also have improved solubility in pharmacological compositions over the parent drug. An example, without limitation, of a pro-drug would be a compound of the invention wherein it is administered as an ester (the "pro-drug") to facilitate transmittal across a cell membrane where water solubility is not beneficial, but then it is metabolically hydrolyzed to the carboxylic acid once inside the cell where water solubility is beneficial. Pro-drugs have many useful properties. For example, a pro-drug may be more water soluble than the ultimate drug, thereby facilitating intravenous administration of the drug. A pro-drug may also have a higher level of oral bioavailability than the ultimate drug. After administration, the prodrug is enzymatically or chemically cleaved to deliver the ultimate drug in the blood or tissue.

Exemplary pro-drugs upon cleavage release the corresponding free acid, and such hydrolyzable ester-forming residues of the compounds of this invention include but are not limited to carboxylic acid substituents (e.g., —C(O)$_2$H or a moiety that contains a carboxylic acid) wherein the free hydrogen is replaced by ($C_1$-$C_4$)alkyl, ($C_2$-$C_{12}$)alkanoyloxymethyl, ($C_4$-$C_9$)1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N-($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl($C_1$-$C_2$)alkyl and piperidino-, pyrrolidino-or morpholino($C_2$-$C_3$)alkyl.

Other exemplary pro-drugs release an alcohol or amine of a compound of the invention wherein the free hydrogen of a hydroxyl or amine substituent is replaced by ($C_1$-$C_6$) alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyl-oxymethyl, N-($C_1$-$C_6$)alkoxycarbonylamino-methyl, succinoyl, ($C_1$-$C_6$)alkanoyl, α-amino($C_1$-$C_4$)alkanoyl, arylactyl and α-aminoacyl, or α-aminoacyl-α-aminoacyl wherein said α-aminoacyl moieties are independently any of the naturally occurring L-amino acids found in proteins, —P(O)(OH)$_2$, —P(O)(O($C_1$-$C_6$)alkyl)$_2$ or glycosyl (the radical resulting from detachment of the hydroxyl of the hemiacetal of a carbohydrate).

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991). Protected forms of the inventive compounds are included within the scope of this invention.

The term "chemically protected form," as used herein, pertains to a compound in which one or more reactive functional groups are protected from undesirable chemical reactions, that is, are in the form of a protected or protecting group (also known as a masked or masking group). It may be convenient or desirable to prepare, purify, and/or handle the active compound in a chemically protected form.

By protecting a reactive functional group, reactions involving other unprotected reactive functional groups can be performed, without affecting the protected group; the protecting group may be removed, usually in a subsequent step, without substantially affecting the remainder of the molecule. See, for example, Protective Groups in Organic Synthesis (T. Green and P. Wuts, Wiley, 1991), and Protective Groups in Organic Synthesis (T. Green and P. Wuts; 3rd Edition; John Wiley and Sons, 1999).

For example, a hydroxy group may be protected as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(=O)CH$_3$—OAc).

For example, an aldehyde or ketone group may be protected as an acetal or ketal, respectively, in which the carbonyl group (C(=O)) is converted to a diether (C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRC(=O)R) or a urethane (—NRC(=O)OR), for example, as: a methyl amide (—NHC(=O)CH$_3$); a benzyloxy amide (—NHC(=O) OCH$_2$C$_6$H$_5$NHCbz); as a t-butoxy amide (—NHC(=O)OC (CH$_3$)$_3$—NHBoc); a 2-biphenyl-2-propoxy amide (—NHC (=O)OC(CH$_3$)$_2$C$_6$H$_4$C$_6$H$_5$NHBoc), as a 9-fluorenylmethoxy amide (—NHFmoc), as a 6-nitroveratryloxy amide (—NHNvoc), as a 2-trimethylsilylethyloxy amide (—NHTeoc), as a 2,2,2-trichloroethyloxy amide (—NHTroc), as an allyloxy amide (—NHAlloc), as a 2-(phenylsulfonyl)ethyloxy amide (—NHPsec); or, in suitable cases (e.g., cyclic amines), as a nitroxide radical.

For example, a carboxylic acid group may be protected as an ester or an amide, for example, as: a benzyl ester; a t-butyl ester; a methyl ester; or a methyl amide.

For example, a thiol group may be protected as a thioether (—SR), for example, as: a benzyl thioether; or an acetamidomethyl ether (—SCH$_2$NHC(=O)CH$_3$).

Combination Therapy

In certain embodiments, the invention relates to a method of co-administering a compound of Formula I and at least one other therapeutic agent. The compound and other therapeutic agent may be administered simultaneously or sequentially. When the other therapeutic agents are administered simultaneously they can be administered in the same or separate formulations, but are administered at the same time. The other therapeutic agents are administered sequentially with one another and with the compounds, when the administration of the other therapeutic agents and the compounds is temporally separated. The separation in time between the administration of these compounds may be a matter of minutes or it may be longer. Other therapeutic agents include but are not limited to anti-viral vaccines and anti-viral agents. In some instances the inhibitors are administered with multiple therapeutic agents, i.e., 2, 3, 4 or even more different anti-viral agents.

An anti-viral vaccine is a formulation composed of one or more viral antigens and one or more adjuvants. The viral antigens include proteins or fragments thereof as well as whole killed virus. Adjuvants are well known to those of skill in the art.

Antiviral agents are compounds that prevent infection of cells by viruses or replication of the virus within the cell. There are many fewer antiviral drugs than antibacterial drugs because viruses are more dependent on host cell factors than bacteria. There are several stages within the process of viral infection which can be blocked or inhibited by antiviral agents. These stages include, attachment of the virus to the host cell (immunoglobulin or binding peptides), membrane penetration inhibitors, e.g. T-20, uncoating of the virus (e.g. amantadine), synthesis or translation of viral mRNA (e.g. interferon), replication of viral RNA or DNA (e.g. nucleotide analogues), maturation of new virus proteins (e.g. protease inhibitors), and budding and release of the virus.

Nucleotide analogues are synthetic compounds that are similar to nucleotides, but which have an incomplete or abnormal deoxyribose or ribose group. Once the nucleotide analogues are in the cell, they are phosphorylated, producing the triphosphate formed which competes with normal nucleotides for incorporation into the viral DNA or RNA. Once the triphosphate form of the nucleotide analogue is incorporated into the growing nucleic acid chain, it causes irreversible association with the viral polymerase and thus chain termination. Nucleotide analogues include, but are not limited to, acyclovir (used for the treatment of herpes simplex virus and varicella-zoster virus), gancyclovir (useful for the treatment of cytomegalovirus), idoxuridine, ribavirin (useful for the treatment of respiratory syncitial virus), dideoxyinosine, dideoxycytidine, zidovudine (azidothymidine), imiquimod, and resimiquimod.

The interferons are cytokines that are secreted by virus-infected cells as well as immune cells. The interferons function by binding to specific receptors on cells adjacent to the infected cells, causing the change in the cell which protects it from infection by the virus. α-and β-interferon also induce the expression of Class I and Class II MHC molecules on the surface of infected cells, resulting in increased antigen presentation for host immune cell recognition. α-and β-interferons are available as recombinant forms and have been used for the treatment of chronic hepatitis B and C infection. At the dosages which are effective for anti-viral therapy, interferons have severe side effects such as fever, malaise and weight loss.

Anti-viral agents that may be useful in the methods of the invention include but are not limited to immunoglobulins, amantadine, interferons, nucleotide analogues, and other protease inhibitors (other than the papain-like cysteine protease inhibitors-although combinations of papain-like cysteine protease inhibitors are also useful). Specific examples of anti-viral agents include but are not limited to Acemannan; Acyclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscarnet Sodium; Fosfonet Sodium; Ganciclovir; Ganciclovir Sodium; Idoxuridine; Kethoxal; Lamivudine; Lobucavir; Memotine Hydrochloride; Methisazone; Nevirapine; Penciclovir; Pirodavir; Ribavirin; Rimantadine Hydrochloride; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; and Zinviroxime.

Immunoglobulin therapy is used for the prevention of viral infection. Immunoglobulin therapy for viral infections is different than bacterial infections, because rather than being antigen-specific, the immunoglobulin therapy functions by binding to extracellular virions and preventing them from attaching to and entering cells which are susceptible to the viral infection. The therapy is useful for the prevention of viral infection for the period of time that the antibodies are present in the host. In general there are two types of immunoglobulin therapies, normal immunoglobulin therapy and hyper-immunoglobulin therapy. Normal immune globulin therapy utilizes a antibody product which is prepared from the serum of normal blood donors and pooled. This pooled product contains low titers of antibody to a wide range of human viruses, such as hepatitis A, parvovirus, enterovirus (especially in neonates). Hyper-immune globulin therapy utilizes antibodies which are prepared from the serum of individuals who have high titers of an antibody to a particular virus. Those antibodies are then used against a specific virus. Another type of immunoglobulin therapy is active immunization. This involves the administration of antibodies or antibody fragments to viral surface proteins.

Pharmaceutical Compositions

The invention provides pharmaceutical compositions for use in treating or preventing viral infections in vitro or in vivo, wherein the composition comprises inhibitors of Usp14. In one aspect, the invention provides pharmaceutically acceptable compositions which comprise a therapeutically-effective amount of one or more of the compounds described above, formulated together with one or more pharmaceutically acceptable carriers (additives) and/or diluents. In another aspect, the agents of the invention can be administered as such, or administered in mixtures with pharmaceutically acceptable carriers and can also be administered in conjunction with other agents. Conjunctive therapy thus includes sequential, simultaneous and separate, or co-administration of one or more compound of the invention, wherein the therapeutic effects of the first administered has not entirely disappeared when the subsequent compound is administered.

As described in detail below, the pharmaceutical compositions of the invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

As set out above, in certain embodiments, agents of the invention may be compounds containing a basic functional group, such as amino or alkylamino, and are, thus, capable of forming pharmaceutically-acceptable salts with pharmaceutically-acceptable acids. These salts can be prepared in situ in the administration vehicle or the dosage form manufacturing process, or through a separate reaction of a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (see, for example, Berge et al. (1977) "Pharmaceutical Salts", J. Pharm. Sci. 66:1-19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the invention may be compounds containing one or more acidic functional groups and, thus, are capable of forming pharmaceutically-acceptable salts with pharmaceutically-acceptable bases. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

The formulations of the compounds of the invention may be presented in unit dosage form and may be prepared by any methods well known in the art of pharmacy. The amount of active ingredient which can be combined with a carrier material to produce a single dosage form will vary depending upon the host being treated and the particular mode of administration. The amount of active ingredient which can be combined with a carrier material to produce a single dosage form will generally be that amount of the agent which produces a therapeutic effect.

In certain embodiments, a formulation of the invention comprises an excipient, including, but not limited to, cyclodextrins, liposomes, micelle forming agents, e.g., bile acids, and polymeric carriers, e.g., polyesters and polyanhydrides; and an agent of the invention. In certain embodiments, an aforementioned formulation renders orally bioavailable a agent of the invention.

Methods of preparing these formulations or compositions may include the step of bringing into association a compound of the invention with the carrier and, optionally, one or more accessory ingredients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the invention as an active ingredient. A compound of the invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol, glycerol monostearate, and non-ionic surfactants; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. Compositions of the invention may also be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

Exemplary formulations comprising agents of the invention are determined based on various properties including, but not limited to, chemical stability at body temperature, functional efficiency time of release, toxicity and optimal dose.

The preparations of the invention may be given orally, parenterally, topically, or rectally. They are of course given in forms suitable for each administration route. For example, they are administered in tablets or capsule form, by injection, inhalation, eye lotion, ointment, suppository, administration by injection, infusion or inhalation; topical by lotion or ointment; and rectal by suppositories.

Regardless of the route of administration selected, the compounds of the invention, which may be used in a suitable hydrated form, and/or the pharmaceutical compositions of the invention, are formulated into pharmaceutically-acceptable dosage forms by conventional methods known to those of skill in the art.

EXAMPLES

The invention now being generally described, it will be more readily understood by reference to the following, which is included merely for purposes of illustration of certain aspects and embodiments of the invention, and is not intended to limit the invention.

Example 1

Inhibition of DENV2 Replication by IU1

To determine the effect of USP14 inhibition on viral replication, $2\times10^5$ HEK293T cells that were preincubated with various concentrations of IU1 (ENAMINE Ltd., Kiev, Ukraine) were infected for 4 h, with DENV2 (New Guinea C strain) at 0.1 moi. After 70 h at 37° C., supernatant was collected and the viral titer was determined by plaque assay on Vero cells. The viral yield was reduced by 20 fold in the presence of 75 µM IU1, with a half maximal effective concentration ($EC_{50}$) of 40 µM (FIG. 1A). No plaques were observed with 100 µM IU1 in our plaque assay. These results suggest that enhanced protein degradation inhibits DENV2 replication.

Cell viability was also evaluated to make sure that the titer reduction was not due to compound cytotoxicity. Cell viability was measured using the cell proliferation based MTT [3-(4,5-dimethylthiazol-2-yl)-2,5-diphenyl tetrazolium bromide] assay. Cell viability assays were carried out for both HEK293 T and HeLa cells. Each well of a 96-well plate was seeded with $2\times10^4$ cells in 100 µl DMEM. After overnight incubation, media were removed and replaced with 100 µl of fresh media containing either DMSO or various concentrations (0-1000 µM) of IU1 in DMSO. Cell viability was determined after 48 h at 37° C. using a MTT cell-proliferation kit from ATCC, following the manufacturer's protocol. The half maximal inhibitory concentrations ($IC_{50}$) for HEK293 T and HeLa cells were 300 and 259 µM, respectively (FIG. 1B). IU1-mediated inhibition of DENV2 replication was not specific for HEK293 T cells; a similar result was obtained in HeLa cells (data not shown). This is the first observation that enhanced protein degradation inhibits viral replication. The results are unexpected, because inhibition of the UPS reduces the viral yield.

Example 2

Inhibition of DENV2 by IU1 Post-Entry

Viruses have been shown to manipulate the UPS to facilitate their replication at various stages of their life cycle, including entry, trafficking, translation, genome replication, maturation, and release. To determine whether IU1 inhibits viral entry or a later stage of viral replication, IU1 was added immediately after infection, and then assayed for DENV2 production as described above. Post-infection addition of IU1 reduced the titer to 37% and 0.5% of maximum with 75 and 100 µM IU1, respectively (FIG. 1A). However, the reduction in viral titer was less than that observed when HEK293 T cells were preincubated with IU1. Differences in titers between preinfection and post-infection addition of IU1 at 75 and 100 µM concentrations are statistically significant (p=0.029 and 0.004, respectively), but not significant at 0-50 µM IU1 concentrations (p>0.05). This result suggests that an effective intracellular concentration must be reached before IU1 can exercise its effect. UPS inhibitors exert their effect on WNV replication at a post-entry step, indicating that UPS is necessary for either viral genome replication or at a later stage of the viral replication. This suggests that, similarly to UPS inhibitors, IU1 inhibits DENV2 replication at a post-entry stage of the viral life cycle.

Example 3

Effect of IU1 on Flaviviridae Viruses

Figure 2:
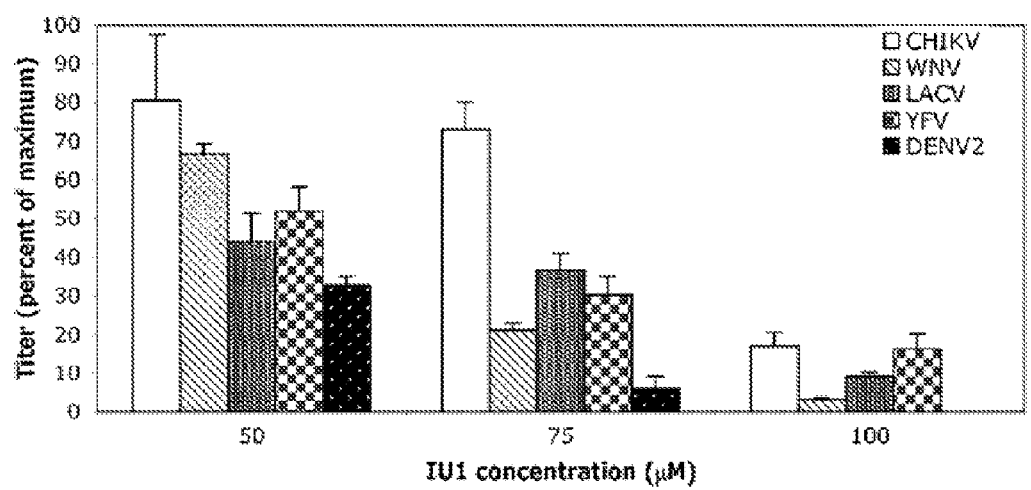
FIG. 2 depicts titer reductions in the presence of various concentrations of IU1. Titer reductions at 50, 75, and 100 μM IU1 concentrations are shown. The effect of IU1 was not evident below 50 μM of IU1, and above 100 μM cell death contributes significantly to titer reductions. Error bars represent standard deviations. p values are for WNV, 0.0002 at 50 μM, <0.0001 at 75 and 100 μM; DENV2, 0.037 at 50 μM, 0.014 at 75 μM; CHIKV, 0.33 at 50 μM, 0.15 at 75 μM, 0.005 at 100 μM; LACV, 0.005 at 50 μM, 0.002 at 75 μM, 0.0006 at 100 μM, and for YFV, 0.01 at 50 μM, 0.002 at 75 μM, and 0.001 at 100 μM.
Figure 3:
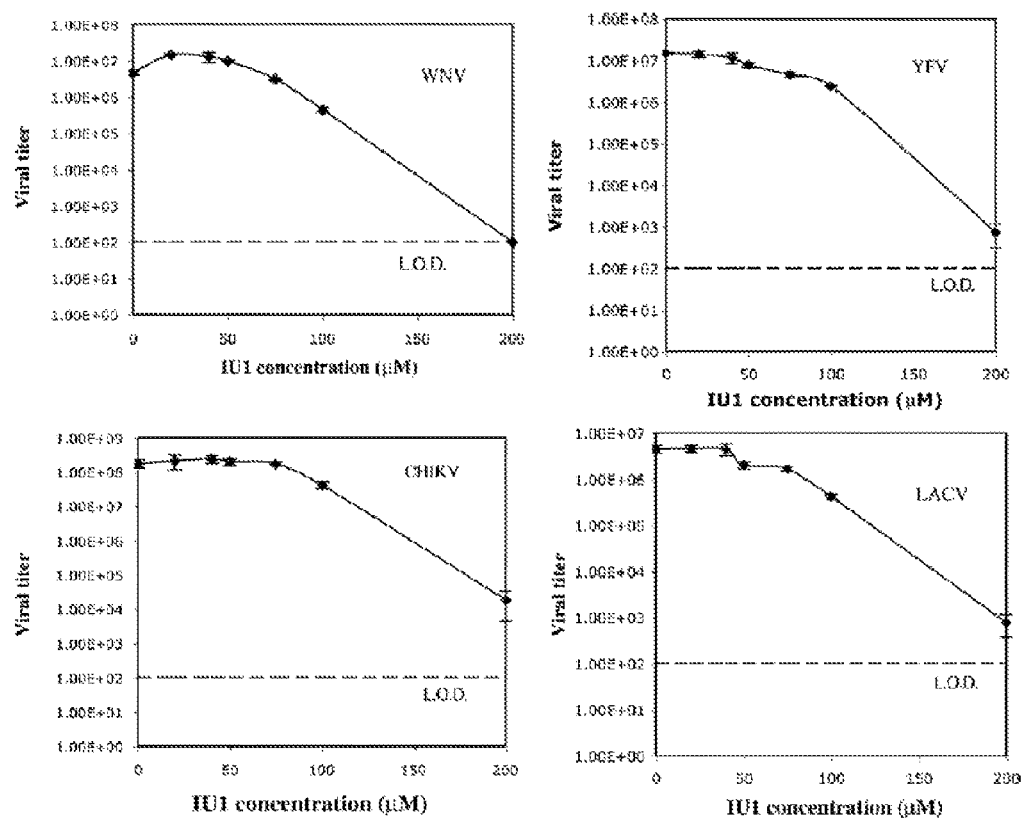
FIG. 3 depicts the antiviral activity of IU1 against WNV, YFV, LACV, and CHIKV. Cells were preincubated with IU1 for 4 h before infection. Results of three replicates are shown. Error bars represent standard deviations. For WNV, no plaques were observed with 200 μM IU1. The dotted lines represent the limit of detection of the plaque assay.
Figure 4:
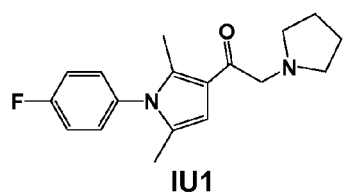
FIG. 4 depicts the structure of IU1.

IU1 exhibits a modest effect on WNV, yellow fever virus (YFV), and La Crosse virus (LACV) replication, but Chikungunya virus (CHIKV) replication is insensitive to the presence of IU1 Inhibition of yellow fever virus (YFV, 17D vaccine strain) and WNV (WNO2-1956) by IU1 was evaluated to determine whether this compound interferes with replication of other flaviviruses. DENV, WNV, and YFV represent three different serogroups within the Flaviviridae family (12). Since WNV generated a small number of infectious particles in HEK293 T cells in these studies, HeLa cells were used for WNV and the HEK293 T cells for YFV. As shown in FIGS. 2 and 3, both viruses had modest reductions in viral yield in the presence of IU1. WNV and YFV titers were reduced by 3-5 fold with 75 µM IU1. The WNV titer with 20 µM IU1 was significantly higher (p<0.001) than that without the drug (FIG. 3). One possible explanation for this result is that low concentrations of IU1 may cause enhanced degradation of certain viral growth inhibitory factors (e.g., those involved in innate immune response) without significant reduction in the level of factors essential for viral replication, resulting in an increased viral titer. At higher concentrations of IU1, a reduction of viral titers is seen, possibly due to increased degradation of factors essential for viral replication.

Example 4

Effect of IU1 on Other Viruses

It was also determined whether IU1 interferes with replication of viruses from other families, including LACV [(LAC74-32813); Bunyaviridae] that contains negative-strand RNAs as its genetic material, and CHIKV [(LR2006-OPY1); Togaviridae], which like the flaviviruses contains a positive-sense single-stranded RNA genome. HEK293 T cells were used for these experiments. While the effect of IU1 on CHIKV is negligible or non-existent at sub-lethal concentrations of IU1, replication of LACV was reduced by 3 fold with 75 µM of IU1 (FIGS. 2 and 3), suggesting that LACV replication is similarly affected by enhanced protein degradation.

EQUIVALENTS

While specific embodiments of the subject invention have been discussed, the above specification is illustrative and not restrictive. Many variations of the invention will become apparent to those skilled in the art upon review of this specification. The appended claims are not intended to claim all such embodiments and variations, and the full scope of the invention should be determined by reference to the claims, along with their full scope of equivalents, and the specification, along with such variations.

All publications and patents mentioned herein are hereby incorporated by reference in their entirety as if each individual publication or patent was specifically and individually indicated to be incorporated by reference. In case of conflict, the present application, including any definitions herein, will control.

We claim:

1. A method of treating or preventing a viral infection in a subject comprising administering to the subject an effective amount of a compound, or a pharmaceutically acceptable salt, solvate, hydrate, prodrug, chemically-protected form, enantiomer or stereoisomer thereof, wherein the compound is represented by Formula I

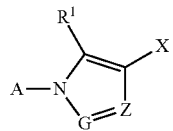

wherein, independently for each occurrence,
A is aryl, heteroaryl, carbocyclyl, heterocyclyl, or biaryl;
$R^1$ is hydrogen, alkyl, haloalkyl, fluoroalkyl, lower alkoxy, halo or trifluoromethyl;
G is —N= or —C($R^2$)=;
Z is =C($R^8$)—, =C($R^2$)— or =N—;
$R^2$ is hydrogen, alkyl, haloalkyl, fluoroalkyl, lower alkoxy, halo or trifluoromethyl; or, when G is —C($R^2$)= and Z is =C($R^2$)—, the two $R^2$ taken together are

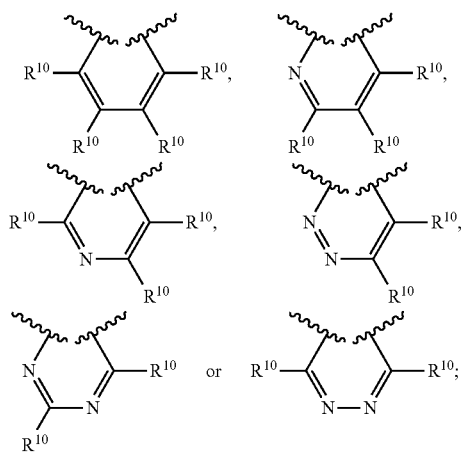

X is

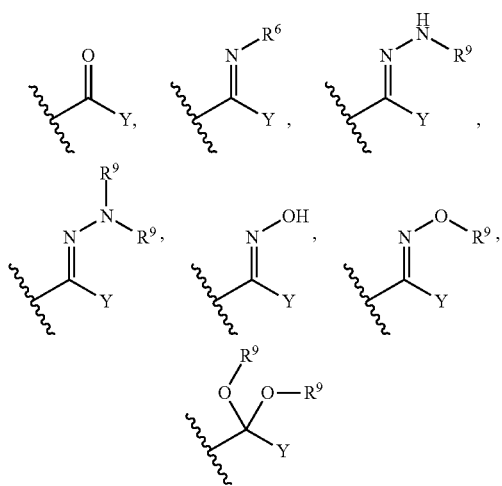

or heteroaryl;
Y is —$CH_2NR^3R^4$, —$CH_2$(N-heterocyclyl), —$CH_2NH(CH_2)_nNH(alkyl)$, —$CH_2NH(CH_2)_nN(alkyl)_2$, —$CH_2NH(CH_2)_n$(N-heterocyclyl), —$CH_2N(alkyl)(CH_2)_nNH(alkyl)$, —$CH_2N(alkyl)(CH_2)_nN(alkyl)_2$, —$CH_2N(alkyl)(CH_2)_n$(N-heterocyclyl), —$CH_2NH(CH_2)_nO(alkyl)$, —$CH_2N(alkyl)(CH_2)_nO(alkyl)$, —$NR^3R^4$, —$NR^5NR^6R^7$, —$NR^5$(N-heterocyclyl), or —N-heterocyclyl;
n is 1, 2, 3 or 4;
$R^3$ is hydrogen, alkyl, substituted alkyl, alkoxyalkyl, haloalkyl, fluoroalkyl, aryl, aralkyl, heteroaryl, or heteroaralkyl;
$R^4$ is hydrogen, alkyl, substituted alkyl, alkoxyalkyl, haloalkyl, fluoroalkyl, aryl, aralkyl, heteroaryl, or heteroaralkyl;
$R^5$ is hydrogen, alkyl, substituted alkyl, alkoxyalkyl, haloalkyl, fluoroalkyl, aryl, aralkyl, heteroaryl, or heteroaralkyl;
$R^6$ is hydrogen, alkyl, substituted alkyl, alkoxyalkyl, haloalkyl, fluoroalkyl, aryl, aralkyl, heteroaryl, or heteroaralkyl;
$R^7$ is hydrogen, alkyl, substituted alkyl, alkoxyalkyl, haloalkyl, fluoroalkyl, aryl, aralkyl, heteroaryl, or heteroaralkyl;
$R^8$ is hydrogen, alkyl, substituted alkyl, alkoxyalkyl, haloalkyl, fluoroalkyl, aryl, aralkyl, heteroaryl, or heteroaralkyl;
$R^9$ is alkyl; or two $R^9$ taken together with the nitrogen to which they are bound are an N-heterocyclyl group; and
$R^{10}$ is hydrogen, alkyl, haloalkyl, fluoroalkyl, alkoxy, alkoxyalkyl, halo, trifluoromethyl, sulfoxymethyl, sulfonamido, amino, amido, N-heterocyclyl, aminoalkyl, amidoalkyl, or N-heterocyclylalkyl.

2. The method of claim 1, wherein the viral infection is a result of a virus of family Flaviviridae.

3. The method of claim 1, wherein the viral infection is a result of a virus of genus Flavivirus, Pestivirus, or Hepacivirus.

4. The method of claim 1, wherein the viral infection is a result of a virus of genus Flavivirus.

5. The method of claim 1, wherein the viral infection is selected from the group consisting of: Dengue fever, Japanese encephalitis, Kyasanur Forest disease, Murray Valley encephalitis, St. Louis encephalitis, Tick-borne encephalitis, West Nile encephalitis, Yellow fever, and Hepatitis C.

6. A method of inhibiting replication of a virus in a host cell comprising contacting the host cell with an effective amount of a compound, or a pharmaceutically acceptable salt, solvate, hydrate, prodrug, chemically-protected form, enantiomer or stereoisomer thereof, wherein the compound is represented by Formula I

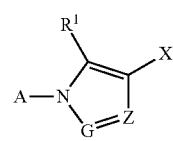

wherein, independently for each occurrence,
A is aryl, heteroaryl, carbocyclyl, heterocyclyl, or biaryl;
$R^1$ is hydrogen, alkyl, haloalkyl, fluoroalkyl, lower alkoxy, halo or trifluoromethyl;

G is —N= or —C($R^2$)=;
Z is =C($R^8$)—, =C($R^2$)— or =N—;
$R^2$ is hydrogen, alkyl, haloalkyl, fluoroalkyl, lower alkoxy, halo or trifluoromethyl; or, when G is —C($R^2$)= and Z is =C($R^2$)—, the two $R^2$ taken together are

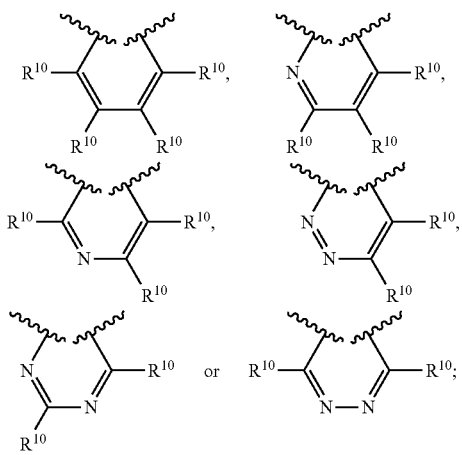

X is

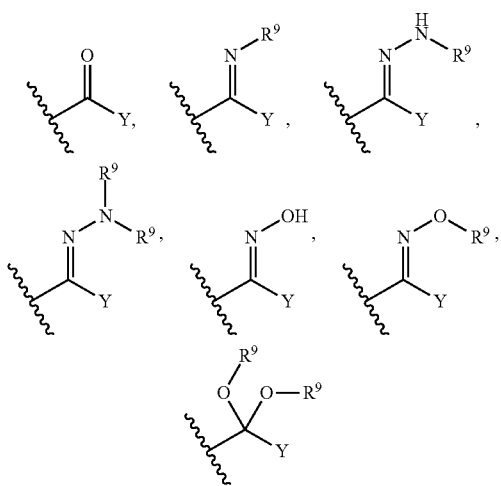

or heteroaryl;
Y is —$CH_2NR^3R^4$, —$CH_2$(N-heterocyclyl), —$CH_2NH(CH_2)_nNH$(alkyl), —$CH_2NH(CH_2)_nN$(alkyl)$_2$, —$CH_2NH(CH_2)_n$(N-heterocyclyl), —$CH_2N$(alkyl)$(CH_2)_nNH$(alkyl), —$CH_2N$(alkyl)$(CH_2)_nN$(alkyl)$_2$, —$CH_2N$(alkyl)$(CH_2)_n$(N-heterocyclyl), —$CH_2NH(CH_2)_nO$(alkyl), —$CH_2N$(alkyl)$(CH_2)_nO$(alkyl), —$NR^3R^4$, —$NR^5NR^6R^7$, —$NR^5$(N-heterocyclyl), or —N-heterocyclyl;
n is 1, 2, 3 or 4;
$R^3$ is hydrogen, alkyl, substituted alkyl, alkoxyalkyl, haloalkyl, fluoroalkyl, aryl, aralkyl, heteroaryl, or heteroaralkyl;
$R^4$ is hydrogen, alkyl, substituted alkyl, alkoxyalkyl, haloalkyl, fluoroalkyl, aryl, aralkyl, heteroaryl, or heteroaralkyl;
$R^5$ is hydrogen, alkyl, substituted alkyl, alkoxyalkyl, haloalkyl, fluoroalkyl, aryl, aralkyl, heteroaryl, or heteroaralkyl;
$R^6$ is hydrogen, alkyl, substituted alkyl, alkoxyalkyl, haloalkyl, fluoroalkyl, aryl, aralkyl, heteroaryl, or heteroaralkyl;
$R^7$ is hydrogen, alkyl, substituted alkyl, alkoxyalkyl, haloalkyl, fluoroalkyl, aryl, aralkyl, heteroaryl, or heteroaralkyl;
$R^8$ is hydrogen, alkyl, substituted alkyl, alkoxyalkyl, haloalkyl, fluoroalkyl, aryl, aralkyl, heteroaryl, or heteroaralkyl;
$R^9$ is alkyl; or two $R^9$ taken together with the nitrogen to which they are bound are an N-heterocyclyl group; and
$R^{10}$ is hydrogen, alkyl, haloalkyl, fluoroalkyl, alkoxy, alkoxyalkyl, halo, trifluoromethyl, sulfoxymethyl, sulfonamido, amino, amido, N-heterocyclyl, aminoalkyl, amidoalkyl, or N-heterocyclylalkyl.

7. The method of claim 6, wherein the host cell is contacted with the compound before exposure to the virus.

8. The method of claim 6, wherein the host cell is contacted with the compound after exposure to the virus.

9. The method of claim 6, wherein the virus is of family *Flaviviridae*.

10. The method of claim 6, wherein the virus is of genus *Flavivirus, Pestivirus,* or *Hepacivirus*.

11. The method of claim 6, wherein the virus is of genus *Flavivirus*.

12. The method of claim 1, wherein the compound is represented by Formula II:

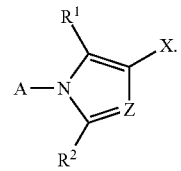

II

13. The method of claim 1, wherein the compound is

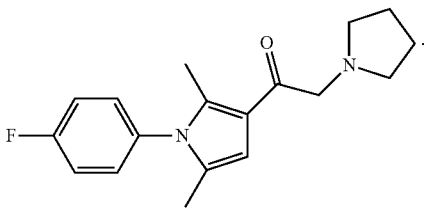 [SMILES: Cc1cc(C(=O)CN2CCCC2)c(C)n1-c1ccc(F)cc1]

14. The method of claim 1, wherein the compound is selected from the group consisting of

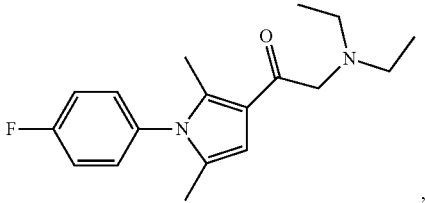

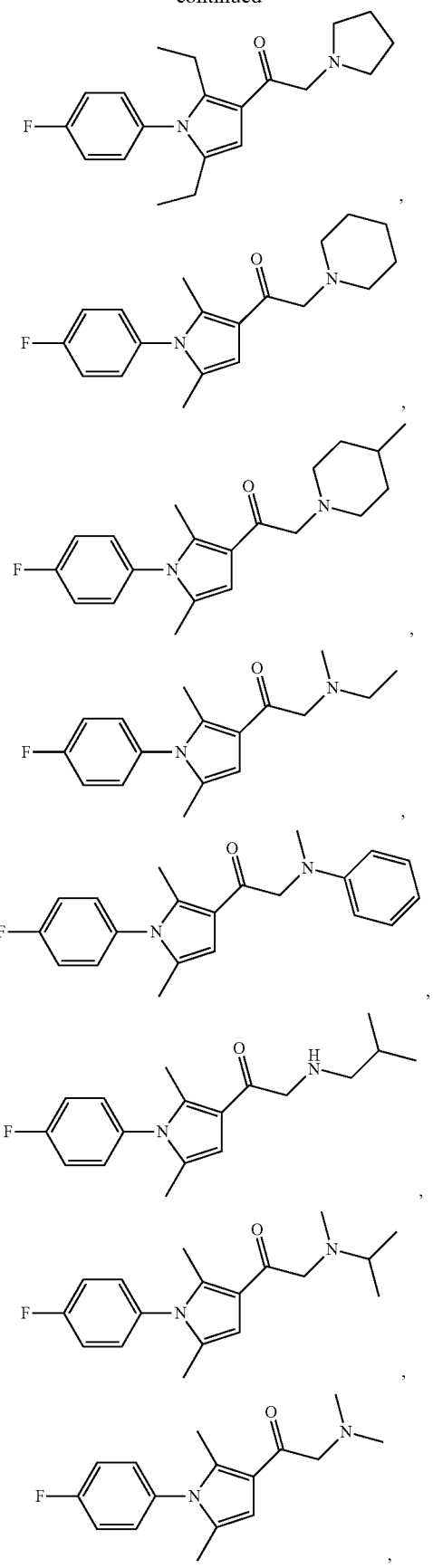
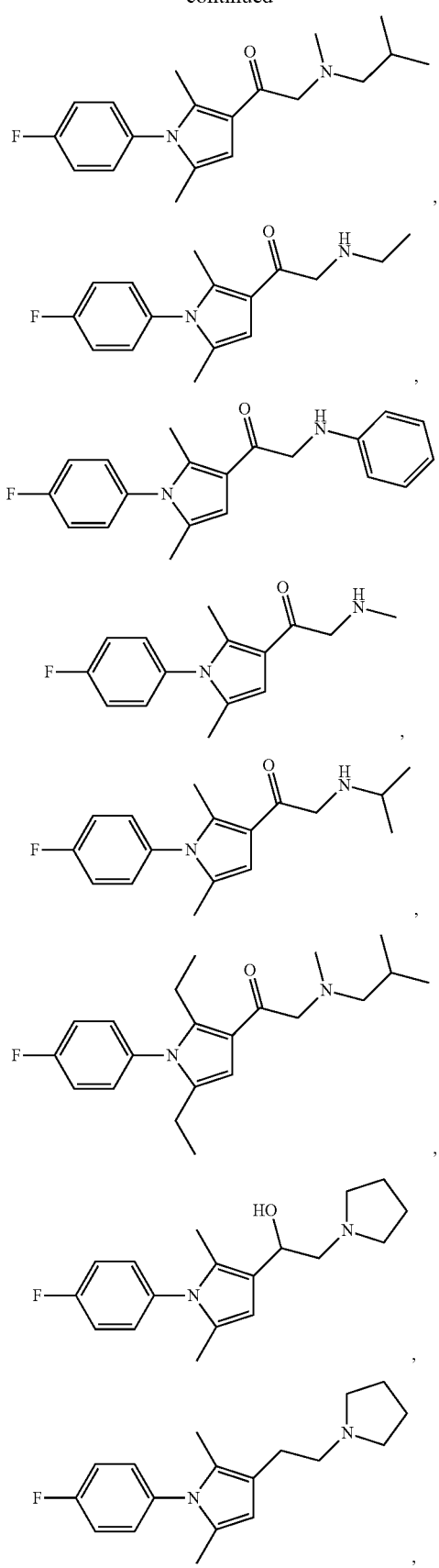

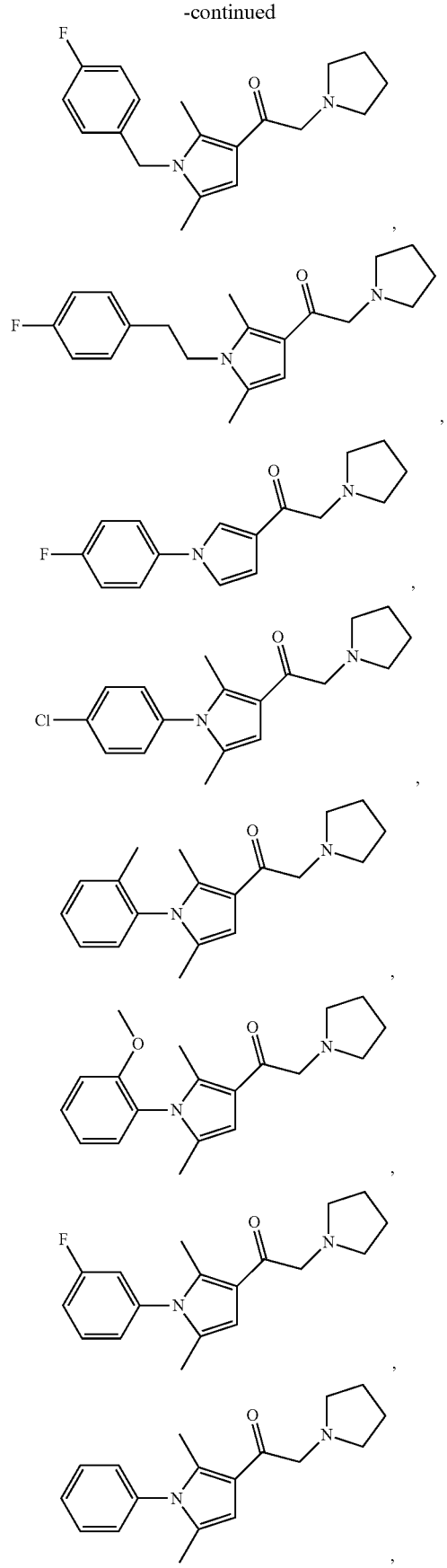
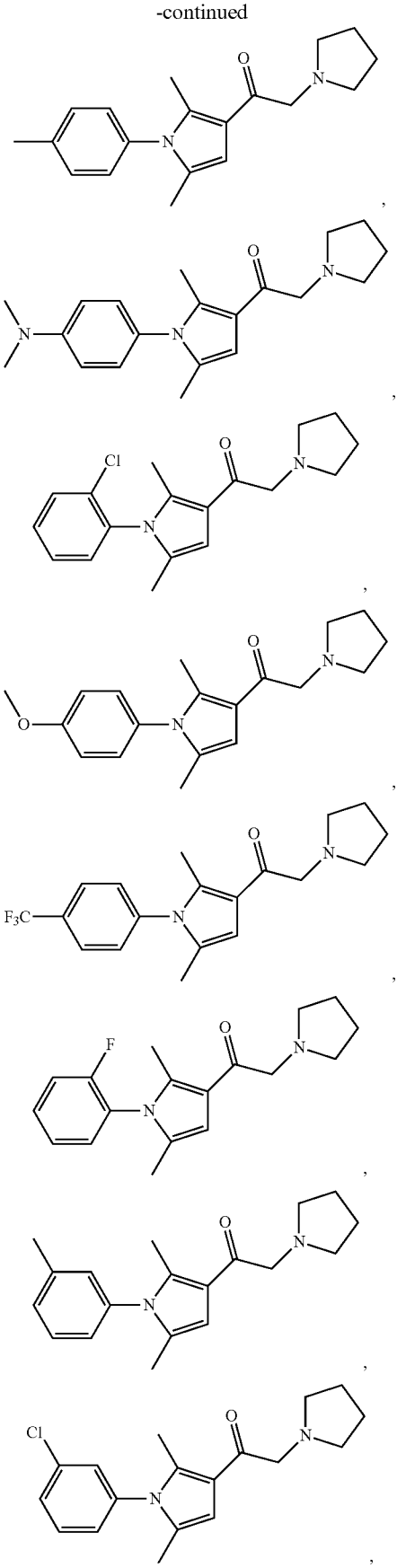

-continued
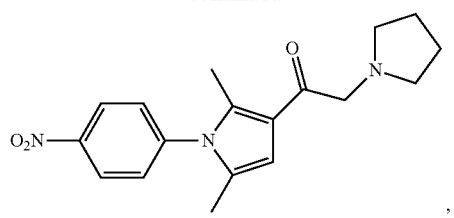
,
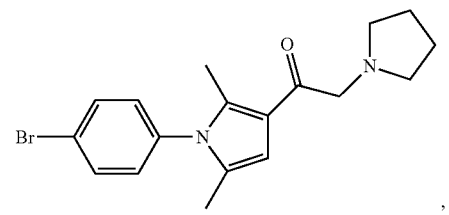
,
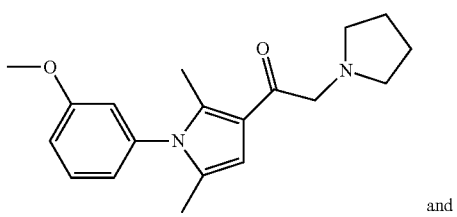
and
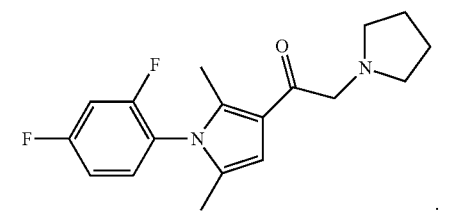
.
15. The method of claim 1, wherein the compound is selected from the group consisting of
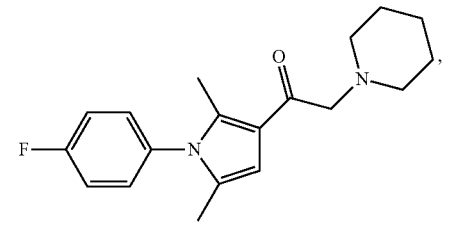
,
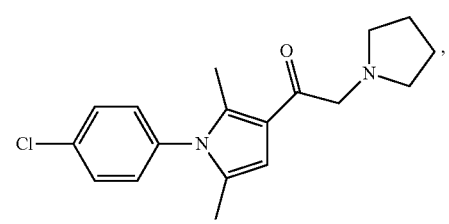
,
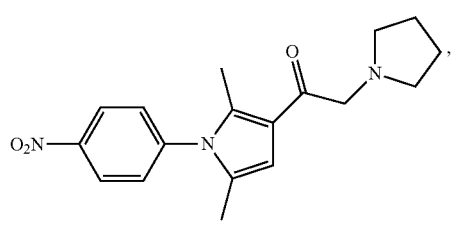
,
-continued
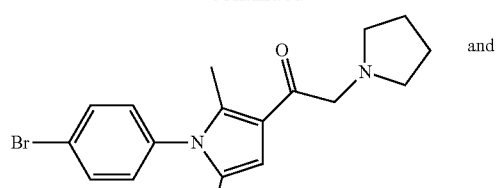
and
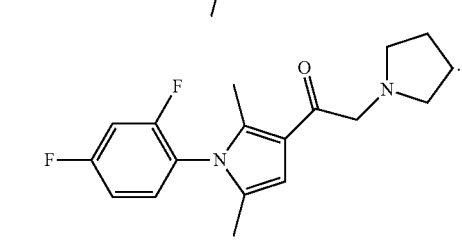
.
16. The method of claim 1, wherein the compound is
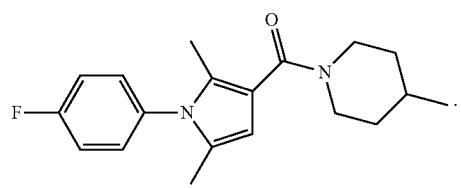
.
17. The method of claim 1, wherein the compound is selected from the group consisting of
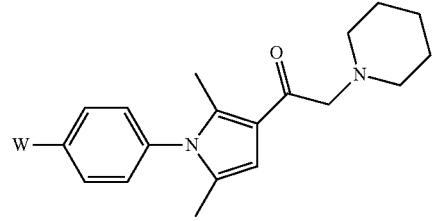
,
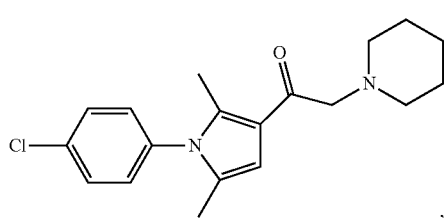
,
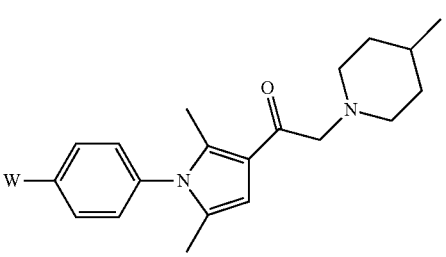
,

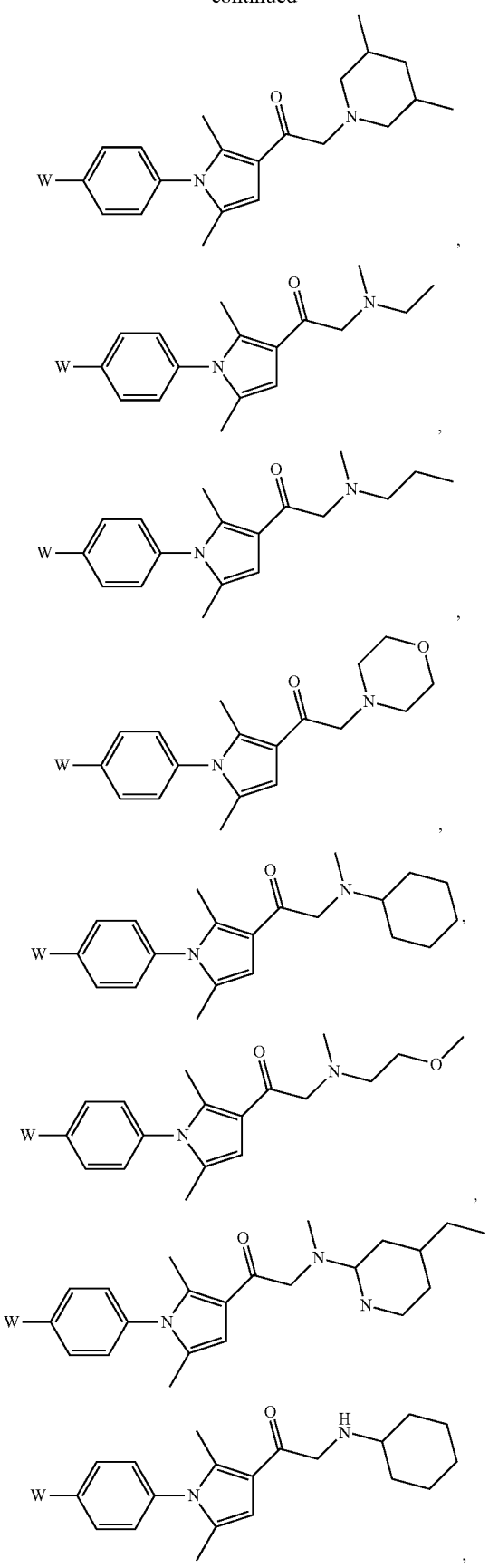
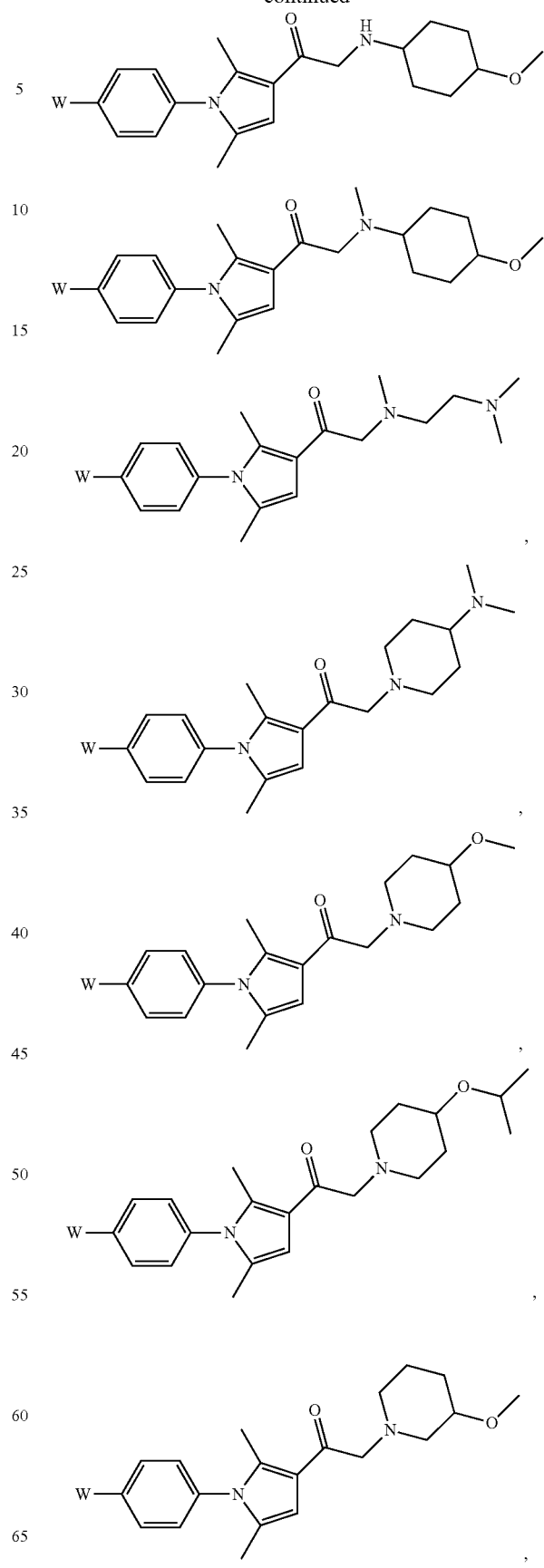

-continued
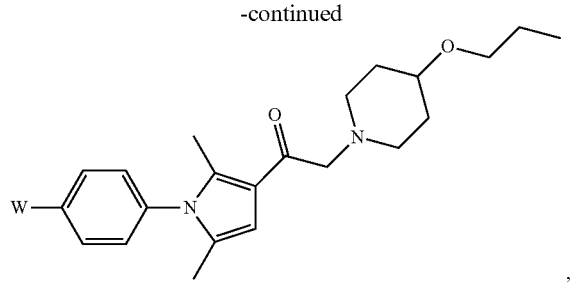
,
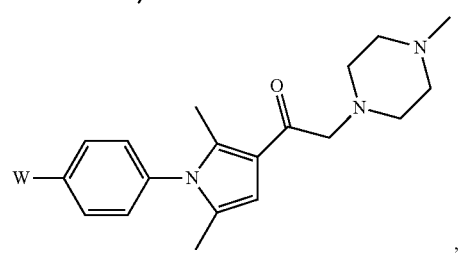
,
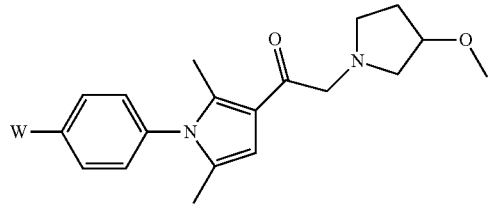
,
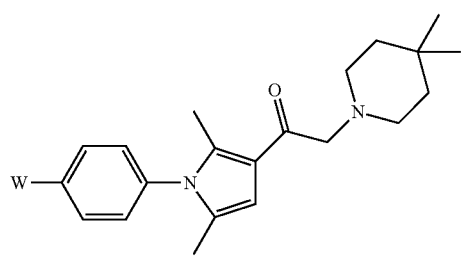
and
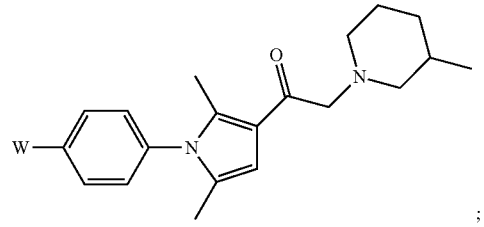
;
wherein W is methyl, fluoro, chloro, nitro, methoxy, ethoxy, —SO$_2$NH$_2$ or —C(=O)NH$_2$.
18. The method of claim 1, wherein the compound is selected from the group consisting of
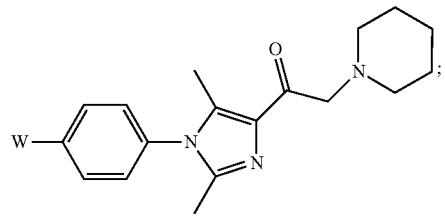
;
wherein W is alkyl, fluoro, chloro, nitro, methoxy, ethoxy, —SO$_2$NH$_2$ or —C(=O)NH$_2$.
19. The method of claim 1, wherein the compound is selected from the group consisting of
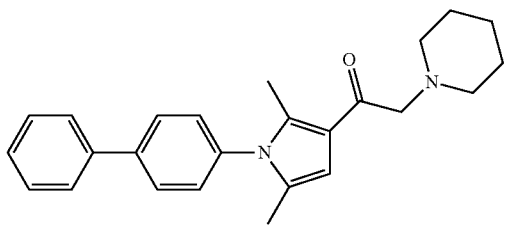
,
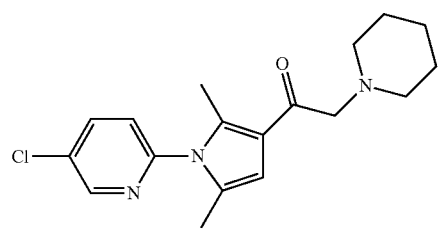
,
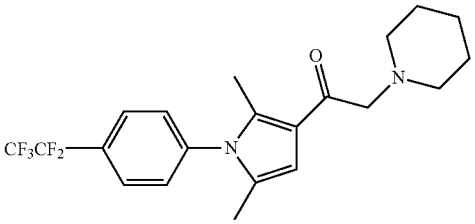
,
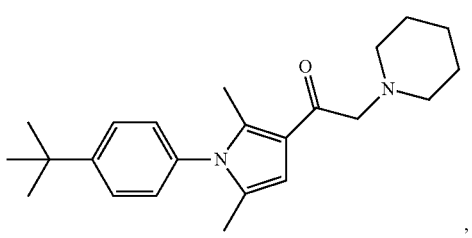
,
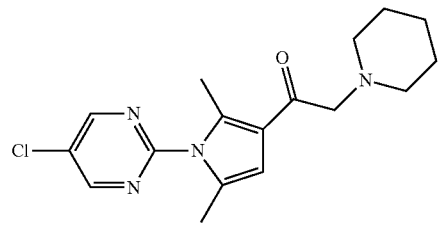
,
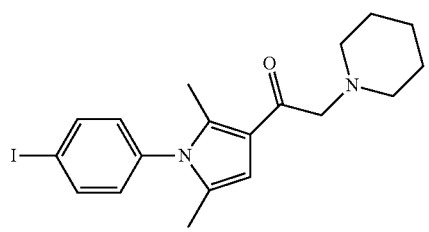
,
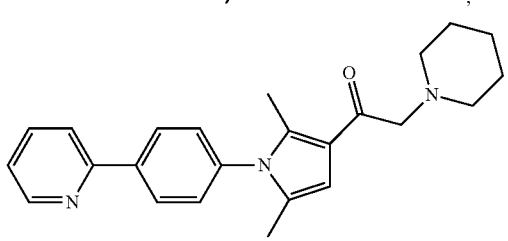
, -continued
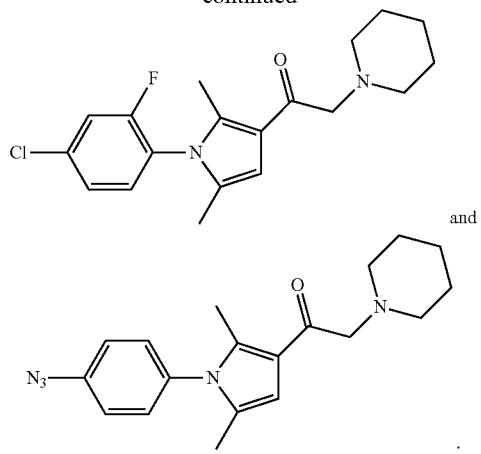
20. The method of claim 1, wherein the compound is selected from the group consisting of
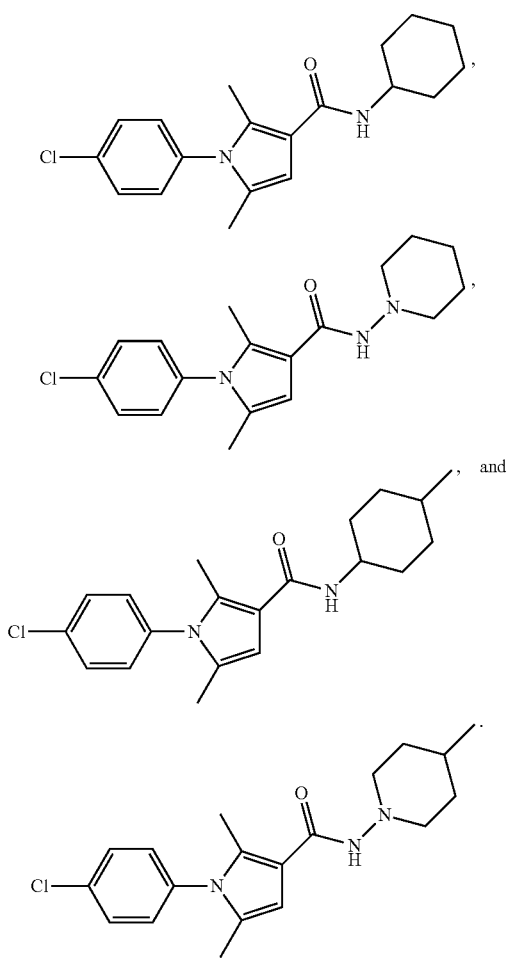
21. The method of claim 1, wherein the compound is selected from the group consisting of
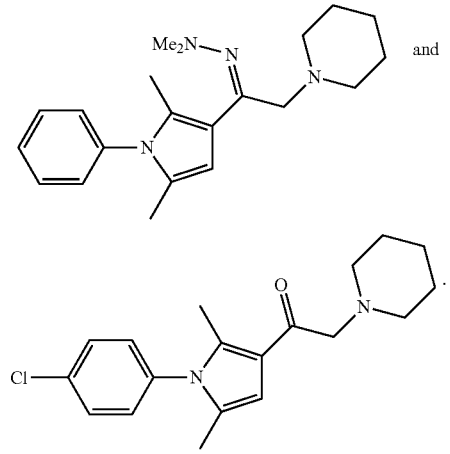
22. The method of claim 1, wherein the compound is selected from the group consisting of
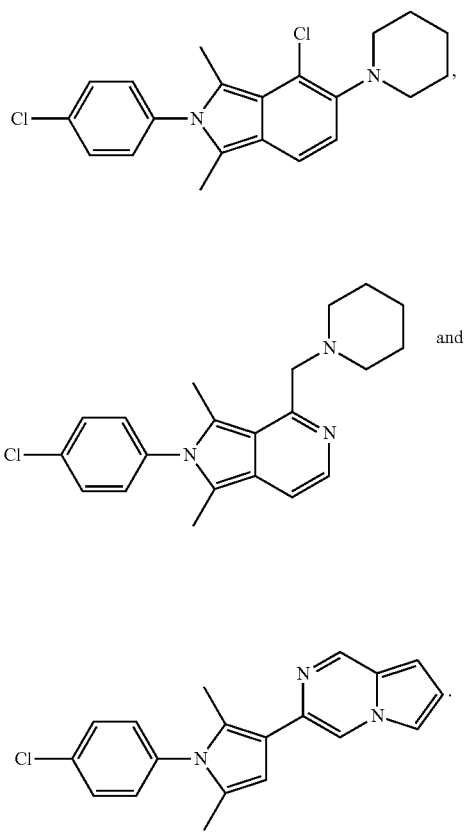
* * * * *